(12) United States Patent
Bray et al.

(10) Patent No.: US 9,750,757 B2
(45) Date of Patent: Sep. 5, 2017

(54) METHODS OF PREVENTION OR TREATMENT FOR PATHOLOGIC THROMBOSIS OR INFLAMMATION

(71) Applicant: THOMAS JEFFERSON UNIVERSITY, Philadelphia, PA (US)

(72) Inventors: Paul F. Bray, Penn Valley, PA (US); Michael Holinstat, Wallingford, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 0 days.

(21) Appl. No.: 15/032,790

(22) PCT Filed: Oct. 27, 2014

(86) PCT No.: PCT/US2014/062336
§ 371 (c)(1),
(2) Date: Apr. 28, 2016

(87) PCT Pub. No.: WO2015/065876
PCT Pub. Date: May 7, 2015

(65) Prior Publication Data
US 2016/0271150 A1    Sep. 22, 2016

Related U.S. Application Data
(60) Provisional application No. 61/896,928, filed on Oct. 29, 2013.

(51) Int. Cl.
| | | |
|---|---|---|
| *A61K 31/655* | (2006.01) | |
| *A61K 31/635* | (2006.01) | |
| *A61K 31/44* | (2006.01) | |
| *A61K 31/505* | (2006.01) | |
| *A61K 31/53* | (2006.01) | |
| *A61K 45/06* | (2006.01) | |

(52) U.S. Cl.
CPC .......... *A61K 31/635* (2013.01); *A61K 31/44* (2013.01); *A61K 31/505* (2013.01); *A61K 31/53* (2013.01); *A61K 45/06* (2013.01)

(58) Field of Classification Search
CPC ................................................. A61K 31/635
USPC ......................................................... 514/157
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,342,958 A | 8/1994 | Wellinga et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 6,365,185 B1 | 4/2002 | Ritschel et al. | |
| 2004/0167131 A1 | 8/2004 | Bolton et al. | |
| 2012/0264756 A1* | 10/2012 | Cohen ................... | A61K 31/44 514/238.2 |

OTHER PUBLICATIONS

Candia, Thrombosis Research 129 (2012) 250-256.*
Baez, J.M., et al., "Decreased lipid efflux and increased susceptibility to cholesterol-induced apoptosis in macrophages lacking phosphatidylcholine transfer protein", Biochem. J., vol. 388, pp. 57-63, 2005.
Bartel, D.P., "MicroRNAs: Genomics, Biogenesis, Mechanism, and Function", Cell, vol. 116, pp. 281-297, 2004.
Benetatos, L., et al., "The microRNAs within the DLK1-DIO3 genomic region: involvement in disease pathogenesis", Cellular and Molecular Life Sciences, vol. 70, Issue 5, pp. 795-814, 2012.
Benjamini, Y., et al., "Controlling the False Discovery Rate: A Practical and Powerful Approach to Multiple Testing", Journal of the Royal Statistical Society, vol. 57, No. 1, pp. 289-300, 1995.
Berge, S.M., et al., "Pharmaceutical Salts", J. Pharm. Sci., vol. 66, No. 1, pp. 1-19, 1977.
Berry, J.D., et al., "Lifetime Risks of Cardiovascular Disease", N. Engl. J. Med., vol. 366, pp. 321-329, 2012.
Bonaca, M.P., et al., "Vorapaxar in Patients with Peripheral Artery Disease Results from TRA2°P-TIMI 50", Circulation, vol. 127, pp. 1522-1529, 2013.
Bray, P.F., et al., "Heritability of platelet function in families with premature coronary artery disease", Journal of Thrombosis and Haemostasis, vol. 5, pp. 1617-1623, 2007.
Chahrour, M., et al., "MeCP2, a Key Contributor to Neurological Disease, Activates and Represses Transcription", Science, vol. 320, No. 5880, pp. 1224-1229, 2008.
Cho, J.H., et al., "Increased Calcium Stores in Platelets from African Americans", Hypertension, vol. 25, pp. 377-383, 1995.
Edelstein, L.C., et al., "MicroRNAs in platelet production and activation", Blood, vol. 117, No. 20, pp. 5289-5296, 2011.
Edelstein, L.C., et al. "Racial Differences in Human Platelet PAR4 Reactivity Reflects Expression of PCTP and miR-376c", Nature Medicine, vol. 19, No. 12, pp. 1609-1616, Nov. 2013.
Eisen, M.B., et al., "Cluster analysis and display of genome-wide expression patterns", PNAS, vol. 95, pp. 14863-14868, 1998.
Exton, J., "Signaling through Phosphatidylcholine Breakdown", The Journal of Biological Chemistry, vol. 265, No. 1, pp. 1-4, 1990.
Fryer, J.D., et al., "Exercise and Genetic Rescue of SCA1 via the Transcriptional Repressor Capicua", Science, vol. 334, No. 6056, pp. 690-693, 2011.

(Continued)

*Primary Examiner* — Nizal Chandrakumar
(74) *Attorney, Agent, or Firm* — Cozen O'Connor

(57) ABSTRACT

The present disclosure relates to methods of affecting platelet activation by the use of a PC-TP inhibitor. The PC-TP inhibitor can be administered to a subject in need thereof in order to prevent or treat pathologic thrombosis, or to treat a disorder treatable by a PAR4 inhibitor.

6 Claims, 21 Drawing Sheets

(56) References Cited

OTHER PUBLICATIONS

Geijtenbeek, T.B.H., et al., "cDNA Cloning and Tissue-Specific Expression of the Phosphatidylcholine Transfer Protein Gene", Biochem J., vol. 316, Pt. 1, pp. 49-55, 1996.
Geiss, G.K., et al., "Direct multiplexed measurement of gene expression with color-coded probe pairs", Nature Biotechnology, vol. 26, No. 3, pp. 317-325, 2008.
Goodall, A.H., et al., "Transcription profiling in human platelets reveals LRRFIP1 as a novel protein regulating platelet function", Blood, vol. 116, No. 22, pp. 4646-4656, 2010.
Guo, L., et al., "Mammalian microRNAs predominantly act to decrease target mRNA levels", Nature, vol. 466, No. 7308, pp. 835-840, 2010.
Henriksen, R.A., et al., "PAR-4 Agonist AYPGKF Stimulates Thromboxane Production by Human Platelets", Arterioscler Thromb Vasc Biol., vol. 22, pp. 861-866, 2002.
Hochberg, Y., et al., "More powerful procedures for multiple significance testing", Statistics in Medicine, vol. 9, Issue 7, pp. 811-818, 1990.
Holinstat, M., et al., "PAR4, but Not PAR1, Signals Human Platelet Aggregation via Ca2+ Mobilization and Synergistic P2Y12 Receptor Activation", The Journal of Biological Chemistry, vol. 281, No. 36, pp. 26665-26674, 2006.
Ihaka, R., et al., "R: A Language for Data Analysis and Graphics", Journal of Computational and Statistical Graphics, vol. 5, No. 3, pp. 299-314, 1996.
International Search Report issued in International Application No. PCT/US2014/062336, filed Oct. 27, 2014, on Feb. 10, 2015.
Jing, F., et al., "Thrombosis Therapy: Focus on Antiplatelet Agents", International Journal of Genomic Medicine, vol. 1, Issue 1, 1000103, 2013.
Kang, H.W., et al., "Regulation of Lipid and Glucose Metabolism by Phosphatidylcholine Transfer Protein", Trends Endocrinol Metab., vol. 21, No. 7, pp. 449-456, 2010.
Kondkar, A.A., et al., "VAMP8/endobrevin is overexpressed in hyperreactive human platelets: suggested role for platelet microRNA", The Journal of Thrombosis and Haemostasis, vol. 8, pp. 369-378, 2010.
Leger A.J., et al., "Protease-Activated Receptors in Cardiovascular Diseases", Circulation, vol. 114, pp. 1070-1077, 2006.
Lev, S., "Non-vesicular lipid transport by lipid-transfer proteins and beyond", Nature Reviews Molecular Cell Biology, vol. 11, pp. 739-750, 2010.
Lova, P., et al., "Contribution of Protease-activated Receptors 1 and 4 and Glycoprotein Ib-IX-V in the Gi-independent Activation of Platelet Rap1B by Thrombin", The Journal of Biological Chemistry, vol. 279, No. 24, Issue of Jun. 11, pp. 25299-25306, 2004.
MacFarlane, S., et al., "Proteinase-Activated Receptors", Pharmacological Reviews, vol. 53, No. 2, pp. 245-282, 2001.
Mahadevappa, V.G., et al., "Relative Degradation of Different Molecular Species of Phosphatidylcholine in Thrombin-stimulated Human Platelets", The Journal of Biological Chemistry, vol. 259, No. 15, pp. 9369-9373, 1984.
Michelson, A.D., "Advances in Antiplatelet Therapy", American Society of Hematology, pp. 62-69, 2011.
Morrow, D.A., et al., "Vorapaxar in the Secondary Prevention of Atherothrombotic Events", The New England Journal of Medicine, vol. 366, pp. 1404-1413.
Mountain, J.L., et al., "Multilocus Genotypes, a Tree of Individuals, and Human Evolutionary History", Am. J. Hum. Genet., vol. 61, pp. 705-718, 1997.
Nagalla, S., et al., "Platelet microRNA-mRNA coexpression profiles correlate with platelet reactivity", Blood, vol. 117, No. 19, pp. 5189-5197, 2011.
O'Donnell, C.J., et al., "Genetic and Environmental Contributions to Platelet Aggregation, The Framingham Heart Study", Circulation, vol. 103, pp. 3051-3056, 2001.
Ozaki, Y., et al., "Thrombin-induced calcium oscillation in human platelets and MEG-01, a megakaryoblastic leukemia cell line", Biochemical and Biophysical Research Communications, vol. 183, No. 2, pp. 864-871, 1992.
Patel, S.R., et al., "The biogenesis of platelets from megakaryocyte proplatelets", J. Clin. Invest., vol. 115, No. 12, pp. 3348-3354, 2005.
Phimister, E.G., "Medicine and the Racial Divide", N. Engl. J. Med., vol. 348, pp. 1081-1082, 2003.
Price, A.L., et al., "Principal components analysis corrects for stratification in genome-wide association studies", Nature Genetics, vol. 38, No. 8, pp. 904-909, 2006.
Quinton, T.M., et al., "Plasmin-mediated Activation of Platelets Occurs by Cleavage of Protease-activated Receptor 4", The Journal of Biological Chemistry, vol. 279, No. 18, Issue of Apr. 30, pp. 18434-18439, 2004.
Risch, N., et al., "Categorization of humans in biomedical research: genes, race and disease", Genome Biology, vol. 3, No. 7, comment2007.1-2007.12, 2002.
Rosenberg, N.A., et al., "Genetric Structure of Human Populations", Science, vol. 298, pp. 2381-2385, 2002.
Rowley, J.W., et al., "Genome-wide RNA-seq analysis of human and mouse platelet transcriptomes", Blood, vol. 118, No. 14, pp. e101-e111, 2011.
Schrick, K., et al., "START lipid/sterol-binding domains are amplified in plants and are predominantly associated with homeodomain transcription factors", Genome Biology, vol. 5, Issue 6, Article R41, 2004.
Scirica, B.M., et al., "Vorapaxar for secondary prevention of thrombotic events for patients with previous myocardial infarction: a prespecified subgroup analysis of the TRA 2°P-TIMI 50 trial", Lancet, vol. 380, No. 9850, pp. 1317-1324, 2012.
Shishova, E.Y., et al. "Genetic Ablation or Chemical Inhibition of Phosphatidylcholine Transfer Protein Attenuates Diet-Induced Hepatic Glucose Production", Hepatology, vol. 54, No. 2, pp. 664-674, 2011.
Strande, J.L., et al. "Thrombin Increases Inflammatory Cytokine and Angiogenic Growth Factor Secretion in Human Adipose Cells in vitro", Journal of Inflammation, vol. 6. No. 4, pp. 1-10, 2009.
Tang, H., et al., "Genetic Structure, Self-Identified Race/Ethnicity, and Confounding in Case-Control Association Studies", Am. J. Hum. Genet., vol. 76, Issue 2, pp. 268-275, 2005.
Thomas, K.L., et al., "Racial Differences in Long-term Survival among Patients with Coronary Artery Disease", American Heart Journal, vol. 160, No. 4, pp. 744-751, 2010.
Tishkoff, S.A., et al., "The Genetic Structure and History of Africans and African Americans", Science, vol. 324, No. 5930, pp. 1035-1044, 2009.
Van Helvoort, A., et al., "Mice without phosphatidylcholine transfer protein have no defects in the secretion of phosphatidylcholine into bile or into lung airspaces", PNAS, vol. 96, pp. 11501-11506, 1999.
Vergnolle, N., "Protease-activated receptors as drug targets in inflammation and pain", Pharmacology & Therapeutics, vol. 123, pp. 292-309, 2009.
Wagel, N., et al., "Small Molecule Inhibitors of Phosphatidylcholine Transfer Protein/StarD2 Identified by High Throughput Screening", Anal Biochem., vol. 383, No. 1, pp. 85-92, 2008.
Xu, Q., et al., "Investigation of Variation in Gene Expression Profiling of Human Blood by Extended Principle Component Analysis", PLoS One, vol. 6, No. 10, e26905, 2011.
Yee, D.L., et al., "Aggregometry detects platelet hyperreactivity in healthy individuals", Blood, vol. 106, No. 8, pp. 2723-2729, 2005.
Yeung, J., et al., "Protein Kinase C Regulation of 12-Lipoxygenase-Mediated Human Platelet Activation", Molecular Pharmacology, vol. 81, No. 3, pp. 420-430, 2012.
Zhang, W., et al., "Evaluation of Genetic Variation Contributing to Differences in Gene Expression between Populations", The American Journal of Human Genetics, vol. 82, pp. 631-640, 2008.
The 1000 Genomes Project Consortium: A map of human genome variation from population scale sequencing, Nature, vol. 467, No. 7319, pp. 1061-1073, 2010. Europe PMC Funders Author Manuscripts.

* cited by examiner

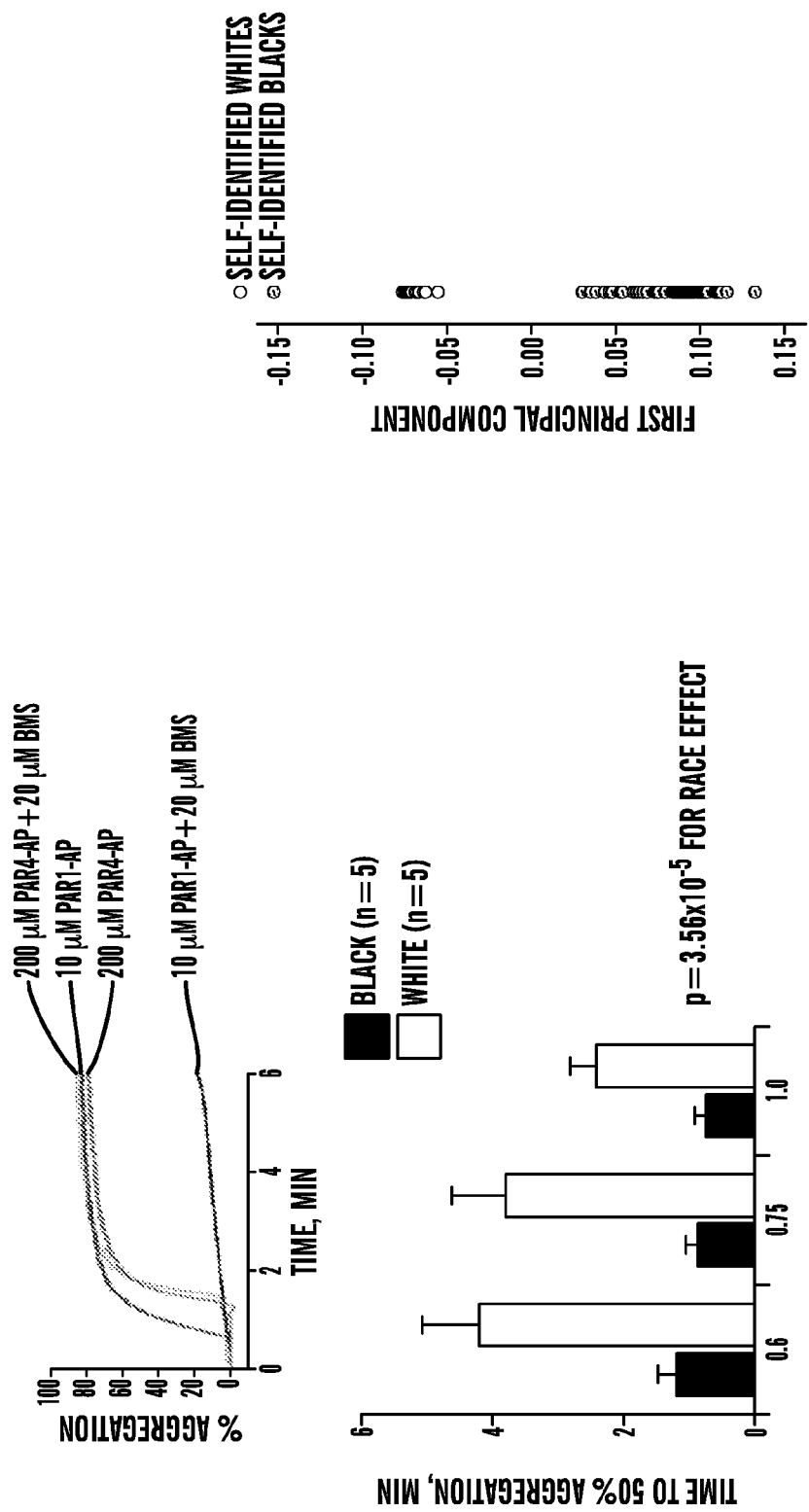

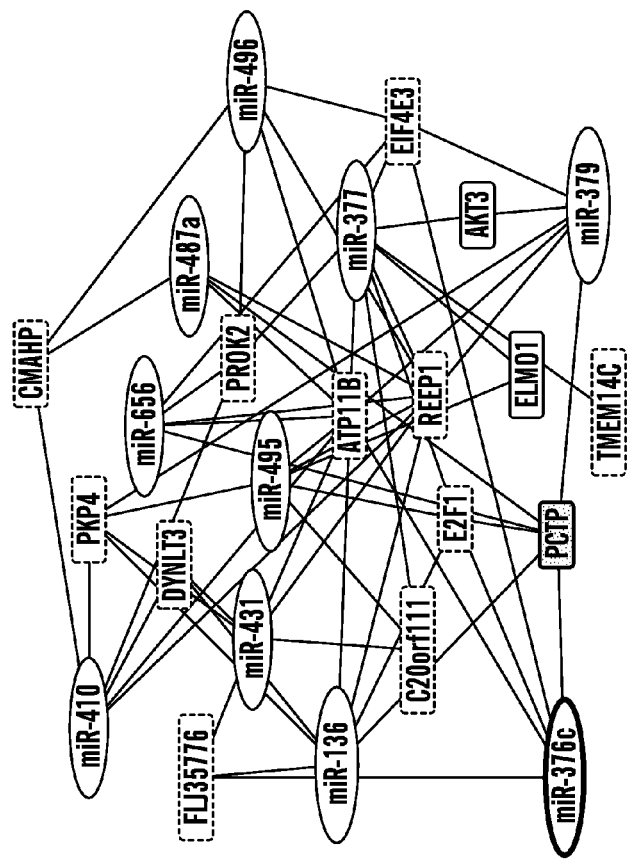
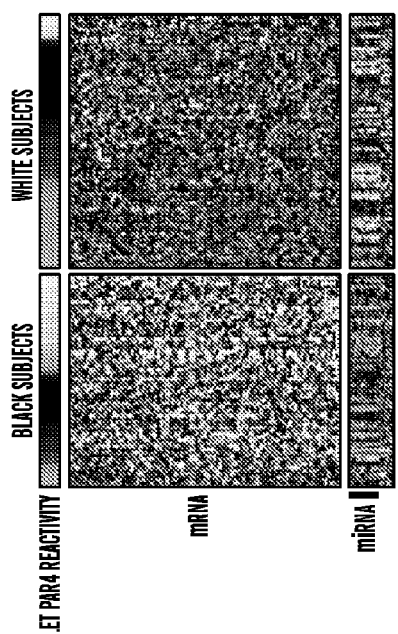
FIG. 3A
FIG. 3B
FIG. 3C

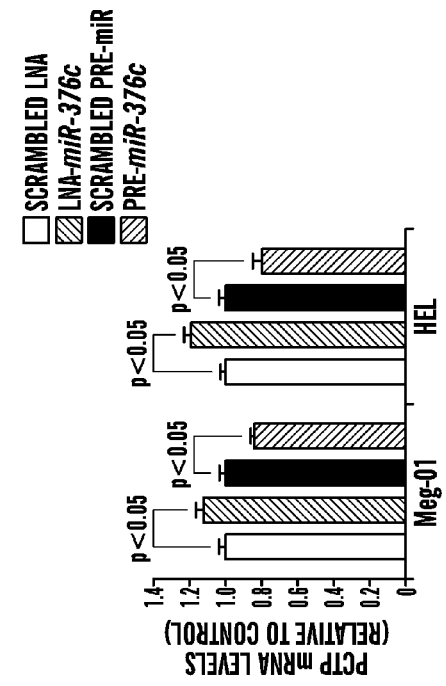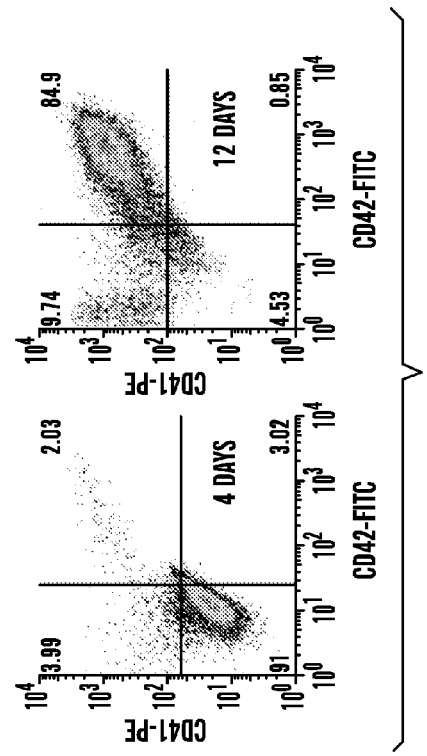
FIG. 4A
FIG. 4B
FIG. 4C
FIG. 4D

METHODS OF PREVENTION OR TREATMENT FOR PATHOLOGIC THROMBOSIS OR INFLAMMATION

CROSS-REFERENCE TO RELATED APPLICATION

This application claims benefit under 35 U.S.C. §119(e) of U.S. Provisional Application No. 61/896,928 filed Oct. 29, 2013, the contents of which are incorporated herein by reference in its entirety.

GOVERNMENT SUPPORT

This invention was made with government support under grant no. R01 HL102482 awarded by NIH and NHLBI. The government has certain rights in the invention.

SEQUENCE LISTING

The instant application contains a Sequence Listing which has been submitted electronically in ASCII format and is hereby incorporated by reference in its entirety. Said ASCII copy, created on Oct. 16, 2014, is named 003252-079421-PCT_SL.txt and is 758 bytes in size.

TECHNICAL FIELD

The present disclosure relates generally to methods of preventing pathologic thrombosis, treating pathologic thrombosis, or treating a disorder treatable by a PAR4 inhibitor in a patient in need thereof.

BACKGROUND

Platelets are essential in normal hemostasis to prevent hemorrhage. However, pathologic thrombosis occurs when circulating platelets become activated and aggregate into a platelet plug at the site of vessel injury, leading to vascular occlusion and life-threatening conditions such as myocardial infarction and stroke. According to the Centers for Disease Control and Prevention, about 715,000 people each year in the United States suffer from a heart attack and many more from strokes.

Several FDA-approved drugs exist in the market to prevent or treat pathologic thrombosis by targeting key pathways of platelet activation such as thromboxane $A_2$ synthesis, ADP-mediated signaling and integrin $\alpha IIb\beta 3$. These drugs include aspirin, ticlopidine, clopidogrel, prasugrel, abciximab, eptifibatide, tirofiban, dipyridamole, cilostazol, and ticagrelor. However, each of these drugs has its own limitations, including weak therapeutic effects (e.g., aspirin), multiple side effects (e.g., ticlopidine, cilostazol, prasugrel), patient-to-patient variability in response and slow onset of action (e.g., clopidogrel), and intravenous injection only (e.g., abciximab, eptifibatide, tirofiban) (Michelson, Hematology 2011, 62-69). Accordingly, there is a strong need to develop and identify new compounds and/or methods for prevention or treatment of pathologic thrombosis.

SUMMARY

Protease-activated receptors (PARs, e.g., PAR1 and PAR4) play important roles in platelet activation. Highly expressed in platelets, PARs are a subfamily of related G protein-coupled receptors that are activated by the amino terminus of their extracellular domain. Platelet activation can be more sustained through PAR4 than PAR1, therefore, the inhibition of PAR4 activation may provide enhanced therapeutic effect than the inhibition of PAR1 activation. However, there are no current therapies in the market that inhibit platelet activation through PAR4.

The inventor has discovered, inter alia, that phosphatidylcholine transfer protein (PC-TP) is involved in the signaling downstream of protease-activated receptor-4 (PAR4). And thus the inhibition of PC-TP can inhibit PAR4 activation. The ability to inhibit PAR4 activation by a PC-TP inhibitor is novel and unexpected.

Accordingly, one aspect of the invention relates to a method of preventing pathologic thrombosis, treating pathologic thrombosis, or treating a disorder treatable by a protease-activated receptor-4 (PAR4) inhibitor in a subject in need thereof, comprising administering a phosphatidylcholine transfer protein (PC-TP) inhibitor to the subject.

Another aspect of the invention relates to a method of inhibiting platelet activation, the method comprising contacting a platelet with a PC-TP inhibitor.

In some embodiments of all aspects of the invention, the PC-TP inhibitor inhibits PAR4 activation.

In some embodiments of all aspects of the invention, the PC-TP inhibitor is selected from compounds of Formula I:

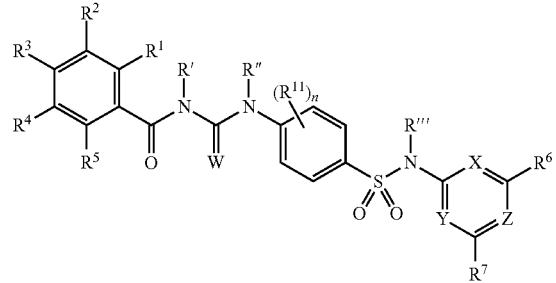

Formula I or a pharmaceutically acceptable salt thereof; wherein:
X is N or $CR^8$;
Y is N or $CR^9$;
Z is N or $CR^{10}$;
W is O;
R', R'', and R''' are each independently selected from H and $C_{1-4}$ alkyl; wherein said $C_{1-4}$ alkyl is optionally substituted by di-$C_{1-6}$-alkylamino;
$R^1$, $R^2$, $R^3$, $R^4$, and $R^5$ are each independently selected from H, halogen, cyano, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{a'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{a''}$ groups;

or $R^1$ and $R^2$, together with the carbon atoms to which they are attached, form a phenyl or $C_{1-6}$ heteroaryl ring, which is optionally substituted with 1, 2, 3, or 4 independently selected $R^{a''}$ groups;

or $R^2$ and $R^3$, together with the carbon atoms to which they are attached, form a phenyl or $C_{1-6}$ heteroaryl ring, which is optionally substituted with 1, 2, 3, or 4 independently selected $R^{a''}$ groups;

or $R^3$ and $R^4$, together with the carbon atoms to which they are attached, form a phenyl or $C_{1-6}$ heteroaryl ring, which is optionally substituted with 1, 2, 3, or 4 independently selected $R^{a''}$ groups;

$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{b'}$ groups;

and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{b''}$ groups;

or $R^6$ and $R^8$, together with the carbon atoms to which they are attached, form a phenyl or $C_{1-6}$ heteroaryl ring, which is optionally substituted with 1, 2, 3, or 4 independently selected $R^{b''}$ groups;

or $R^6$ and $R^{10}$, together with the carbon atoms to which they are attached, form a phenyl or $C_{1-6}$ heteroaryl ring, which is optionally substituted with 1, 2, 3, or 4 independently selected $R^{b''}$ groups;

or $R^7$ and $R^9$, together with the carbon atoms to which they are attached, form a phenyl or $C_{1-6}$ heteroaryl ring, which is optionally substituted with 1, 2, 3, or 4 independently selected $R^{b''}$ groups;

or $R^7$ and $R^{10}$, together with the carbon atoms to which they are attached, form a phenyl or $C_{1-6}$ heteroaryl ring, which is optionally substituted with 1, 2, 3, or 4 independently selected $R^{b''}$ groups;

each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

each $R^{a'}$ and $R^{b'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino;

each $R^{a''}$ and $R^{b''}$ is independently selected from halogen, cyano, nitro, hydroxyl, carboxyl, amino, $C_{1-4}$ alkyl, $C_{1-4}$ haloalkyl, $C_{1-4}$ alkoxy, $C_{1-4}$ haloalkoxy, $C_{1-4}$ alkylamino, and di-$C_{1-4}$-alkylamino; and n is an integer selected from 0, 1, 2, 3, and 4;

provided that:

(1) when the compound has Formula I, W is O, Z is CH, n is 0, $R^1$, $R^2$, $R^4$, $R^5$, $R^6$ and $R^7$ are each H, and either X is N and Y is CH, or X is CH and Y is N, then $R^3$ is other than chloro; and (2) when the compound has Formula I, W is O, X is N, Y is N, and Z is $CR^{10}$, then the following provisos apply: (a) when $R^6$ and $R^7$ are each methyl or each H, $R^{10}$ is H, and $R^1$, $R^2$, $R^4$, and $R^5$ are H, then $R^3$ is not methoxy or chloro; and (b) when $R^6$ and $R^7$ are each methyl or each H and $R^{10}$ is H, then at least one of $R^1$, $R^2$, $R^3$, $R^4$, and $R^5$ is other than H.

In some embodiments of all aspects of the invention, the PC-TP inhibitor is selected from: 2,4-dichloro-N-(4-(N-(4,6-dimethylpyrimidin-2-yl)sulfamoyl)phenylcarbamoyl)-benzamide (LDN-193,188); 2-chloro-N-(4-(N-(4,6-dimethylpyrimidin-2-yl)sulfamoyl)phenylcarbamoyl)benzamide; 2,4-dichloro-N-(4-(N-(4,6-dimethylpyridin-2-yl)sulfamoyl)phenylcarbamoyl)benzamide; 2,3-dichloro-N-(4-(N-(4,6-dimethylpyrimidin-2-yl)sulfamoyl)phenylcarbamoyl)-benzamide; 3,4-dichloro-N-(4-(N-(4,6-dimethylpyrimidin-2-yl)sulfamoyl)phenylcarbamoyl)-benzamide; 2,4-dichloro-N-((4-(N-(4,6-dimethylpyrimidin-2-yl)sulfamoyl)phenyl)(methyl)carba-moyl)benzamide; 2,4-dichloro-N-(4-(N-(4,6-dimethylpyrimidin-2-yl)-N-methylsulfamoyl)phenylcarbamoyl)benzamide; 2,4-dichloro-N-(4-(N-(2,6-dimethylpyrimidin-4-yl)sulfa-moyl)phenylcarbamoyl)-benzamide; 2,4-dichloro-N-(4-(N-(3,5-dimethylphenyl)sulfamoyl)phenylcarbamoyl)benzamide; and 2,4-dichloro-N-(4-(N-(4,6-dimethylpyrimidin-2-yl)sulfa-moyl)phenylcarbamoyl)-N-methylbenzamide; or a pharmaceutically acceptable salt thereof.

In some embodiments of all aspects of the invention, the PC-TP inhibitor is 2,4-dichloro-N-(4-(N-(4,6-dimethylpyrimidin-2-yl)sulfamoyl)phenylcarbamoyl)-benzamide (LDN-193,188), or a pharmaceutically acceptable salt thereof.

In some embodiments of all aspects of the invention, the disorder treatable by a PAR4 inhibitor is selected from hepatitis, primary sclerosing cholangitis, sarcoidosis, inflammatory bowel disease, pancreatitis, thyroiditis, and fetal development disorders caused by placental dysfunction.

In some embodiments of all aspects of the invention, the subject is a mammal.

In some embodiments of all aspects of the invention, the mammal is a human.

In some embodiments of all aspects of the invention, the method further comprises administering a PAR1 inhibitor.

In some embodiments of some aspects of the invention, the contacting is in vitro.

In some embodiments of some aspects of the invention, the contacting is in vivo.

In some embodiments of some aspects of the invention, the in vivo contacting is in a subject in need of prevention or treatment for pathologic thrombosis, or treatment for a disorder treatable by a PAR4 inhibitor.

BRIEF DESCRIPTION OF THE DRAWINGS

FIGS. 1A-1C show racial difference in PAR4-mediated platelet aggregation.

FIG. 1A is a plot where 70 black and 84 white PRP samples were assayed by light transmission aggregometry following stimulation with 500 g/ml arachidonic acid (AA), 4 M ADP, anti-CD9 (500, 750 or 2000 ng/ml), collagen-related peptide (CRP, 10 or 20 ng/ml), PAR1-AP (1.0 or 2.5 µM), or PAR4-AP (50 or 75 µM PAR4-AP). Data are mean+/−SEM of maximal % aggregation. Race had no significant association with any agonist except PAR4-AP. *, p<0.0001, 2-sided Mann-Whitney for maximal % aggregation.

FIG. 1B is a plot showing that thrombin activation through PAR4. PAR1 was inhibited with 20 µM BMS-200261 (BMS, PAR1-specific antagonist) and platelet aggregation measured using washed platelets from black (n=5) and white (n=5) donors. Times to 50% aggregation are shown. $p=3.56\times10^{-5}$, partial F statistic for race effect using 2-way ANOVA (concentration, race). The insert demonstrates ability of 20 µM BMS to block maximally stimulated PAR1- but not PAR4-induced platelet aggregation.

FIG. 1C is a plot showing that PCA of 2 million genome wide genotype markers demonstrated two groups of PRAX1 subjects that strongly correlated with self-identified race and ethnicity.

FIG. 2A is a plot showing that mean PC-TP mRNA levels are higher in 70 blacks than 84 whites ($p=1\times10^{-23}$, 2-sided t-test).

FIG. 2B is a plot of PCR validation of PC-TP mRNA. Correlation between microarray and qRT-PCR data using linear regression (SPSS15.0 software). The regression line with its 95% confidence intervals is shown (p<0.0001, Pearson correlation, Fisher's z transform).

FIG. 2C is an image of Representative western blots showing higher PC-TP levels in platelets from 8 blacks than 8 whites. PC-TP and GAPDH antibodies probed filters that were transferred from the same gel.

FIG. 2D is a plot summary of western blot quantification of platelet PC-TP from 70 blacks and 82 whites ($p=3.8\times10^{-6}$, 2 sided t-test).

FIG. 2E is an image of Western blot of mouse platelet PC-TP with controls.

FIG. 2F is a plot showing that PC-TP inhibitor LDN-193, 188 does not block platelet aggregation to PAR1-AP.

FIG. 2G is a plot showing PC-TP inhibitor LDN-193,188 does block PAR4-AP-induced aggregation. The indicated concentrations of LDN-193,188 were incubated for 30 min with washed platelets and stimulated with sub-threshold concentrations of activating PAR peptides.

FIG. 2H is a bar graph summarizes studies from 3 subjects (2W, 1 B). In all 3 cases, LDN-193,188 blocked platelet aggregation to PAR4-AP but not PAR1-AP (p=0.016, 2-sided t-test). Color key for FIGS. 2F-2H shown in FIG. 2F.

FIGS. 2I-2J show calcium mobilization in the megakaryocytic cell line, Meg-01. Cells were transfected with a control siRNA or an siRNA against PC-TP, loaded with Fluo-4-AM and assessed for calcium mobilization after no agonist or stimulation with PAR1-AP (FIG. 2I) or PAR4-AP (FIG. 2J). Data are expressed as change in fluorescence. Curves represent mean±SEM (dark and light lines respectively) of three separate experiments for PAR1-AP and four different experiments for PAR4-4P. No differences were detected with PAR1-AP. *, (p=0.013, 2-sided t-test) for the maximum fold change between siRNA-PC-TP vs. si-control.

FIG. 2K is an image of Western immunoblot of Meg-01 cells transfected with non-targeting siRNA control (si-ctrl) or human PC-TP siRNA-SMART pool (si-PC-TP).

FIG. 2L is a plot showing the effect of race on PAR4-AP-mediated platelet calcium mobilization (p=0.02, 2-way ANOVA).

FIGS. 3A-3C show relationships among racial differences in PAR4 phenotype and transcripts.

FIG. 3A is a set of images showing racial differences between 70 blacks and 84 whites for PAR4 reactivity, mRNAs and miRNAs are presented in 3 heatmaps. Each column represents data from the same individual. Rows represent 93 mRNAs (in middle panel) and 18 miRNAs (lower panel) that are DE by race and correlated with PAR4 reactivity. Vertical bar on the side indicates strongly correlated DLK1-DIO3 region miRNAs. RNAs were analyzed for association with PAR4 reactivity by linear regression and corresponding p-values were determined; the Benjamini-Hochberg FDR method was used to compute q-values.

FIG. 3B shows the network of miRNA-mRNA pairs that are differentially expressed by race and PAR4-mediated platelet aggregation.

FIG. 3C is a table of miR-376c levels quantified by qRT-PCR and correlated against PC-TP mRNA levels, PC-TP protein levels, and PAR4 reactivity in all 154 PRAX samples. Correlations were calculated using a Pearson's Correlation.

FIGS. 4A-4G show regulation of PC-TP expression in megakaryocytes by MiR-376c.

FIG. 4A is a plot showing that transfection of miR-376c diminishes PC-TP protein expression in Dicer-low HCT cells. *, P<0.05.

FIG. 4B is a plot showing that transfection of miR-376c diminishes PC-TP protein expression in the megakaryocytic cell line, Meg-01.

FIG. 4C is a plot showing that transfection of miR-376c locked nucleic acid (LNA) inhibitor increased PC-TP mRNA levels, while overexpression of the miR-376c precursor decreased PC-TP mRNA in megakaryocytic cell lines, Meg-01 and HEL cells. P-value calculation is T-test relative to appropriate scrambled control. Levels were normalized to 13-actin.

FIG. 4D is a set of plot of demonstration of human CD34+ hematopoietic stem cell derived megakaryocytes. Flow cytometric analysis of CD34+ cells cultured for 4 and 12 days and stained for megakaryocyte-specific markers CD41 and CD42.

FIG. 4E is an image of Day 14 megakaryocytes showing proplatelet formation with DNA (DAPI, visualized as purple-blue), α-tubulin (visualized as green) and actin (visualized as red) staining.

FIG. 4F is a plot in which CD61+ day 14 megakaryocytes were isolated, transfected with miR-376c locked nucleic acid (LNA) inhibitor or pre-miR-376c and PC-TP mRNA levels quantified by qRT-PCR. Levels were normalized to 13-actin.

FIG. 4G is a plot in which the 3'UTR of PC-TP was cloned into a luciferase reporter with the wild type (WT) miR-376c target site or a mutated (PC-TP). When co-transfected with miR-376 precursor, only the WT construct was knocked down. Levels were normalized with a 13-gal control.

FIG. 5A is a heatmap of Pearson's correlation coefficients amongst all combinations of pairs of the 178 commonly expressed platelet miRNAs.

FIG. 5B shows the approximate locations of the 54 miRNAs in the DLK1-DIO3 region. Color coding indicates which miRNA genes had at least one mature miRNA product detected above or below the arbitrary threshold of commonly expressed miRNAs and the 4 miRNA genes that were not queried. Figure not to scale.

FIG. 5C is a plot in which each dot represents the average expression of one of the 24 DLK1-DIO3 region miRNAs above cutoff. Using a binomial model, the chance that all 24 of the expressed DLK1-DIO3 miRNAs would be higher in whites is $1.2 \times 10^{-24}$ based on a genome-wide (excluding the DLK1-DIO3 region) rate of 51.4% of DE miRNAs higher in whites.

(FIGS. 7C, 7D) Cumulative quantitative results of (FIG. 7A) and (FIG. 7B) Time to both 20% (FIG. 7C) and 50% (FIG. 7D) aggregation was faster in black subjects than in white at low doses. Statistical tests: (FIG. 7C) 2-way ANOVA, (FIG. 7D) 2-sided t-test. (FIG. 7E) Representative LTA demonstrating BMS-200261 inhibits PAR1 activation peptide (PAR1-AP), but not PAR4 activation peptide (PAR4-AP) mediated platelet aggregation using standard agonist concentrations to elicit maximal aggregation.

FIG. 9A is a plot showing probe-level intensities for the probeset annotated to PC-TP. The data in FIG. 9A demonstrate that probes containing racially dimorphic SNVs show a similar level of racial difference compared to what is observed for almost all of the other probes that are not racially dimorphic. Similar results were obtained for the other 160 probesets that were DE by PAR4.

FIG. 9B is a plot showing probe-level intensities for the probeset annotated to TPSD1 (based on Affymetrix). Data for all black and white subjects for each individual oligo probe are shown in side-by-side boxplots. Oligo probes that harbor a racially dimorphic SNV are contained within the grey rectangles in the plot. FIG. 9B shows an example probeset not differentially expressed between races but containing multiple racially dimorphic SNVs with no differential intensities between any of the probes. Thus the differences in racially dimorphic SNV variation do not drive the gene-level racial difference observed.

DETAILED DESCRIPTION

Figure 1A:
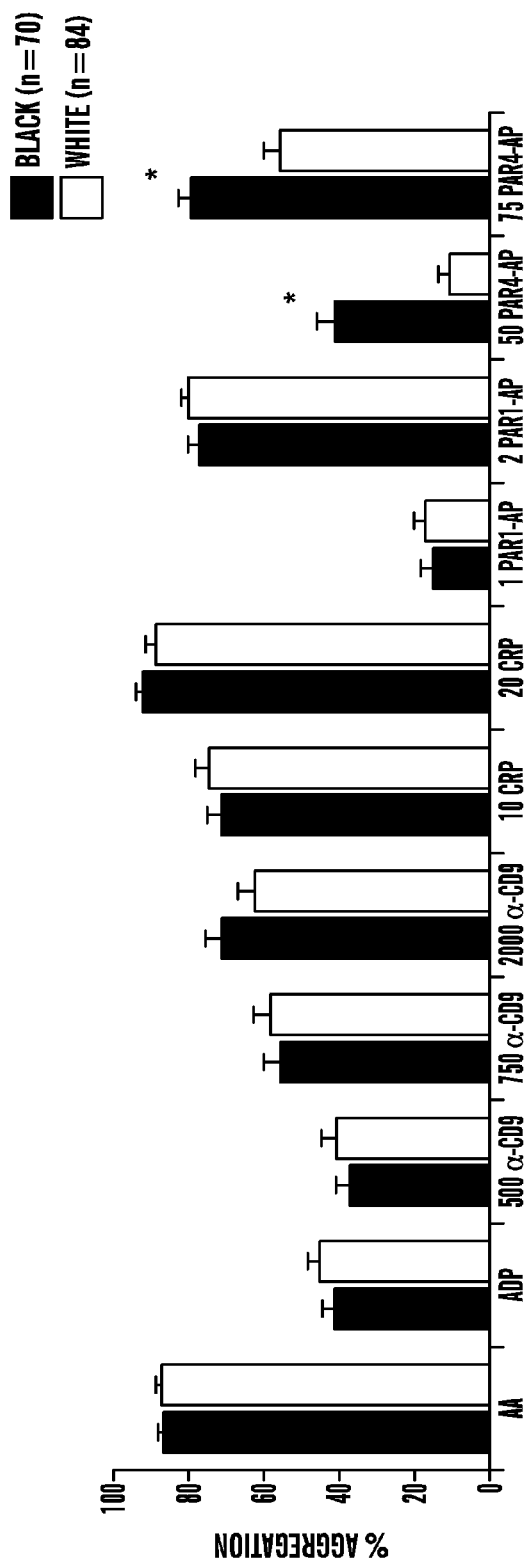

The invention is based, in part, on the inventor's discovery that phosphatidylcholine transfer protein (PC-TP) is involved in the signaling downstream of protease-activated receptor-4 (PAR4). The inventor has discovered, surprisingly, that mRNAs differentially expressed by PAR4 activity are positively enriched in genes with phospholipid transfer activity. Therefore, PC-TP inhibition has implications in PAR4 activation, and this relationship so far has not been appreciated or expected by those skilled in the art. A PC-TP inhibitor can also affect PAR4 activation. In some embodiments, a PC-TP inhibitor is also a PAR4 inhibitor. As used herein, the term "inhibitor" refers to a compound or a mixture of compounds, either synthetic or naturally occurring, has the capability to directly or indirectly affect the function or activity of a protein, whether by binding or not to said protein. An inhibitor can reduce or decrease the activity of the protein by at least 5%, at least 10%, at least 20%, at least 30%, at least 40%, at least 50%, at least 60%, at least 70%, at least 80%, at least 90%, or at least 95%, as compared to before the administration of the inhibitor.

Thrombin is an especially potent physiologic agonist mediating in vivo platelet activation, and human platelets express two thrombin receptors, protease activated receptors 1 and 4, referred to as PAR1 and PAR4 (Leger et al., Circulation 2006, 114, 1070-1077), both of which mediate thrombin signaling in platelet activation. During thrombin-induced platelet activation these receptors couple to specific G proteins, leading to activation of phospholipases and protein kinases, hydrolysis of phosphoinositides and increased cytoplasmic calcium (Abrams et al., Hemostasis and thrombosis: basic principles and clinical practice, 617-629). Numerous differences in platelet activation have been characterized following stimulation of PAR1 or PAR4 (Macfarlane et al., Pharmacol. Rev. 2001, 53, 245-282; Lova et al., J. Biol. Chem. 2004, 279, 25299-25306; Henriksen et al., Arterioscler. Thromb. Vasc. Biol. 2002, 22, 861-866; Holinstat et al., J. Biol. Chem. 2006, 281, 26665-26674). For example, compared to PAR1, PAR4 induces a more sustained rise in $[Ca^{2+}]$ (Holinstat et al., J. Biol. Chem. 2006, 281, 26665-26674) and is responsible for the majority of intracellular calcium flux. Without wishing to be bound by theory, these observations suggest different kinetics or signaling pathways through platelet PAR1 and PAR4.

PC-TP belongs to the steroidogenic acute regulatory transfer protein-related transfer (START) domain superfamily, which constitutes a functionally diverse group of proteins that share a unique START domain for binding lipids (Schrick et al., Genome Biol. 2004, 5, R41). PC-TP has been presumed to be expressed primarily in the liver, kidneys, and testis. PC-TP protein was not known to be present or function in platelets (Geijtenbeek et al., Biochem. J. 1996, 316 Pt 1, 49-55).

PAR4 activation can lead to platelet activation and subsequent platelet aggregation. Thus one aspect of the invention provides a method of affecting platelet activation, the method comprising contacting one or more platelets with a PC-TP inhibitor. In some embodiments, the PC-TP inhibitor inhibits platelet activation. In some embodiments, the contacting is in vitro. In alternative embodiments, the contacting is in vivo.

Accordingly, one aspect provided herein relates to a method for prevention or treatment of pathologic thrombosis in a subject in need thereof, the method comprising administering a PC-TP inhibitor to said subject. As used herein, the term "pathologic thrombosis" refers to a condition wherein a blood clot forms inside a blood vessel, obstructing the flow of blood through the circulatory system. Pathologic thrombosis can include, but is not limited to, venous thrombosis, deep vein thrombosis, portal vein thrombosis, renal vein thrombosis, Budd-Chiari syndrome, Paget-Schroetter disease, Cerebral venous sinus thrombosis, arterial thrombosis, stroke, myocardial infarction, and hepatic artery thrombosis.

Specific PC-TP inhibitors have been disclosed in the art, and these inhibitors can be used in accordance with some embodiments of the invention. By way of examples only, see US20120264756, the contents of which are incorporated by reference in their entirety.

In some embodiments, the PC-TP inhibitor is selected from compounds of Formula I.

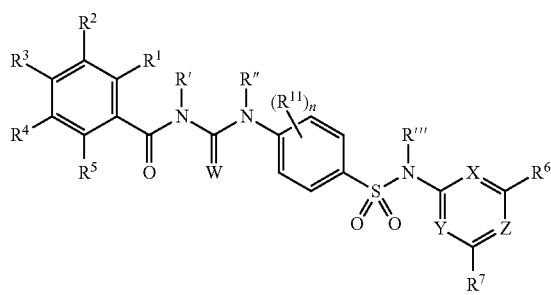

Formula I or a pharmaceutically acceptable salt thereof; wherein:
X is N or $CR^8$;
Y is N or $CR^9$;
Z is N or $CR^{10}$;
W is O;
R', R'', and R''' are each independently selected from H and $C_{1-4}$ alkyl; wherein said $C_{1-4}$ alkyl is optionally substituted by di-$C_{1-6}$-alkylamino;
$R^1$, $R^2$, $R^3$, $R^4$, and $R^5$ are each independently selected from H, halogen, cyano, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{a'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{a''}$ groups;
or $R^1$ and $R^2$, together with the carbon atoms to which they are attached, form a phenyl or $C_{1-6}$ heteroaryl ring, which is optionally substituted with 1, 2, 3, or 4 independently selected $R^{a''}$ groups;
or $R^2$ and $R^3$, together with the carbon atoms to which they are attached, form a phenyl or $C_{1-6}$ heteroaryl ring, which is optionally substituted with 1, 2, 3, or 4 independently selected $R^{a''}$ groups;
or $R^3$ and $R^4$, together with the carbon atoms to which they are attached, form a phenyl or $C_{1-6}$ heteroaryl ring, which is optionally substituted with 1, 2, 3, or 4 independently selected $R^{a''}$ groups;
$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{b'}$ groups;
and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{b''}$ groups;
or $R^6$ and $R^8$, together with the carbon atoms to which they are attached, form a phenyl or $C_{1-6}$ heteroaryl ring, which is optionally substituted with 1, 2, 3, or 4 independently selected $R^{b''}$ groups;
or $R^6$ and $R^{10}$, together with the carbon atoms to which they are attached, form a phenyl or $C_{1-6}$ heteroaryl ring, which is optionally substituted with 1, 2, 3, or 4 independently selected $R^{b''}$ groups;
or $R^7$ and $R^9$, together with the carbon atoms to which they are attached, form a phenyl or $C_{1-6}$ heteroaryl ring, which is optionally substituted with 1, 2, 3, or 4 independently selected $R^{b''}$ groups;
or $R^7$ and $R^{10}$, together with the carbon atoms to which they are attached, form a phenyl or $C_{1-6}$ heteroaryl ring, which is optionally substituted with 1, 2, 3, or 4 independently selected $R^{b''}$ groups;
each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;
each $R^{a'}$ and $R^{b'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino;
each $R^{a''}$ and $R^{b''}$ is independently selected from halogen, cyano, nitro, hydroxyl, carboxyl, amino, $C_{1-4}$ alkyl, $C_{1-4}$ haloalkyl, $C_{1-4}$ alkoxy, $C_{1-4}$ haloalkoxy, $C_{1-4}$ alkylamino, and di-$C_1$-4-alkylamino; and n is an integer selected from 0, 1, 2, 3, and 4;

provided that:

(1) when the compound has Formula I, W is O, Z is CH, n is 0, $R^1$, $R^2$, $R^4$, $R^5$, $R^6$ and $R^7$ are each H, and either X is N and Y is CH, or X is CH and Y is N, then $R^3$ is other than chloro; and (2) when the compound has Formula I, W is O, X is N, Y is N, and Z is $CR^{10}$, then the following provisos apply: (a) when $R^6$ and $R^7$ are each methyl or each H, $R^{10}$ is H, and $R^1$, $R^2$, $R^4$, and $R^5$ are H, then $R^3$ is not methoxy or chloro; and (b) when $R^6$ and $R^7$ are each methyl or each H and $R^{10}$ is H, then at least one of $R^1$, $R^2$, $R^3$, $R^4$, and $R^5$ is other than H.

In some embodiments, the PC-TP inhibitor is selected from the following compounds or pharmaceutically acceptable salts thereof: 2,4-dichloro-N-(4-(N-(4,6-dimethylpyrimidin-2-yl)sulfamoyl)phenylcarbamoyl)-benzamide (LDN-193,188); 2-chloro-N-(4-(N-(4,6-dimethylpyrimidin-2-yl)sulfamoyl)phenylcarbamoyl)benzamide; 2,4-dichloro-N-(4-(N-(4,6-dimethylpyridin-2-yl)sulfamoyl)phenylcarbamoyl)benzamide; 2,3-dichloro-N-(4-(N-(4,6-dimethylpyrimidin-2-yl)sulfamoyl)phenylcarbamoyl)-benzamide; 3,4-dichloro-N-(4-(N-(4,6-dimethylpyrimidin-2-yl)sulfamoyl)phenylcarbamoyl)-benzamide; 2,4-dichloro-N-((4-(N-(4,6-dimethylpyrimidin-2-yl)sulfamoyl)phenyl)(methyl)carba-moyl)benzamide; 2,4-dichloro-N-(4-(N-(4,6-dimethylpyrimidin-2-yl)-N-methylsulfamoyl)phenylcarbamoyl)benzamide; 2,4-dichloro-N-(4-(N-(2,6-dimethylpyrimidin-4-yl)sulfa-moyl)phenylcarbamoyl)-benzamide; 2,4-dichloro-N-(4-(N-(3,5-dimethylphenyl)sulfamoyl)phenylcarbamoyl)benzamide; and 2,4-dichloro-N-(4-(N-(4,6-dimethylpyrimidin-2-yl)sulfa-moyl)phenylcarbamoyl)-N-methylbenzamide.

In some preferred embodiments, the PC-TP inhibitor is 2,4-dichloro-N-(4-(N-(4,6-dimethylpyrimidin-2-yl)sulfamoyl)phenylcarbamoyl)-benzamide (LDN-193,188) or a pharmaceutically acceptable salt thereof.

In some embodiments, the method comprises administering a PC-TP inhibitor in combination with one or more other anti-platelet drugs including, but are not limited to, aspirin, ticlopidine, clopidogrel, prasugrel, abciximab, eptifibatide, tirofiban, dipyridamole, cilostazol, and ticagrelor. In some embodiments, a PC-TP inhibitor is administered before the administration of one or more other anti-platelet drugs. In some embodiments, a PC-TP inhibitor is administered at the same time as the administration of one or more other anti-platelet drugs. In some embodiments, a PC-TP inhibitor is administered after the administration of one or more other anti-platelet drugs.

In some embodiments, the invention relates to a method for prevention or treatment of pathologic thrombosis, the method comprising administering a PC-TP inhibitor in combination with a PAR1 inhibitor. PAR1 inhibitors can include, but are not limited to, vorapaxar, atopaxar, SCH205831, and SCH602539 (Jing & Zhang, International Journal of Genomic Medicine 2013, 1, 1000103). In some embodiments, a PC-TP inhibitor is administered before the administration of a PAR1 inhibitor. In some embodiments, a PC-TP inhibitor is administered at the same time as the administration of a PAR1 inhibitor. In some embodiments, a PC-TP inhibitor is administered after the administration of a PAR1 inhibitor.

PAR4 is expressed at high levels in the liver, lung, small intestine, pancreas, thyroid and placenta. Accordingly, another aspect of the invention relates to a method of treatment for a disorder treatable by a PAR4 inhibitor in a subject in need thereof, the method comprising administering a PC-TP inhibitor to said subject. The disorders can include, but are not limited to, inflammatory disorders of the liver (e.g., hepatitis or primary sclerosing cholangitis), inflammatory disorders of the lung (e.g., sarcoidosis), inflammatory disorders of the bowel (e.g., inflammatory bowel disease), inflammatory disorders of the pancreas (e.g., pancreatitis), thyroiditis, and fetal development disorders caused by placental dysfunction.

In some aspects of all the embodiments, the subject is a non-human mammal.

In some aspects of all the embodiments, the subject is a human.

In some aspects of all the embodiments, the subject is a human who has been previously diagnosed with or identified as suffering from or having a condition in need of treatment (e.g. pathologic thrombosis, hepatitis, primary sclerosing cholangitis, sarcoidosis, inflammatory bowel disease, pancreatitis, thyroiditis, or fetal development disorders caused by placental dysfunction) or one or more complications related to such a condition, and optionally, have already undergone treatment for the condition. Alternatively, a subject can also be one who has not been previously diagnosed as having a condition in need of treatment (e.g. pathologic thrombosis, hepatitis, primary sclerosing cholangitis, sarcoidosis, inflammatory bowel disease, pancreatitis, thyroiditis, or fetal development disorders caused by placental dysfunction) or one or more complications related to such a condition. For example, a subject can be one who exhibits one or more risk factors for pathologic thrombosis or one or more complications related to pathologic thrombosis or a subject who does not exhibit risk factors.

A "subject in need" of treatment for pathologic thrombosis or a disorder treatable by a PAR4 inhibitor can be a subject having pathologic thrombosis or a disorder treatable by a PAR4 inhibitor, diagnosed as having pathologic thrombosis or a disorder treatable by a PAR4 inhibitor, or at risk of developing for pathologic thrombosis or a disorder treatable by a PAR4 inhibitor.

In some aspects, the methods described herein comprise administering an effective amount of a PC-TP inhibitor described herein to a subject in order to alleviate a symptom or reducing a risk factor associated with the disease or condition to be treated. As used herein, the terms "disease", "disorder" and "condition" have the same meaning and are used interchangeably. The term "effective amount" as used herein, in various contexts, would include an amount sufficient to alleviate at least one or more symptoms of the disease, delay the development of a symptom of the disease, alter the course of the development of a symptom of the disease, reduce the risk of death from the disease, or reduce the frequency of a condition occurring. For any given case, an appropriate "effective amount" can be determined by one of ordinary skill in the art using routine experimentation.

It should be noted that the form of the pharmaceutical compositions, the route of administration, the dosage, and the regimen depend upon the condition to be treated, the severity of the condition, the age, weight, sex and race of the patient, etc.

In some embodiments, the PC-TP inhibitors described herein can be administered together with a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g., PC-TP inhibitors as described herein. The carriers may include agents that cause slow release of the compositions to extend the effect of the composition.

A variety of means for administering the compositions described herein to subjects are known to those of skill in the art. In some aspects of all the embodiments of the invention, the compositions are administered through routes, including ocular, oral, parenteral, intravenous, intramuscular, subcutaneous, transdermal, airway (aerosol), pulmonary, cutaneous, topical, or injection administration. Administration can be local or systemic.

The dosage as described herein can be determined by a physician and adjusted, as necessary, to suit observed effects of the treatment to the specific subject. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary depending on a number of clinical factors, such as the subject's sensitivity to a PC-TP inhibitor that is administered. The desired dose or amount can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. The dosage should not be so large as to cause adverse side effects.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. See Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

There is reproducible variation in platelet reactivity among different individuals—a variation that likely contributes to thrombotic risk. The inter-individual variation in platelet reactivity is heritable (O'Donnell et al., Circulation 2001, 103, 3051-3056), and this heritability is greater in blacks than in whites (Bray et al., J. Thromb. Haemost. 2007, 5, 1617-1623), but there is limited understanding of the genetic mechanisms responsible for this variability. Race is an independent predictor of survival in coronary heart disease even when demographic, socioeconomic, and clinical factors are considered (Thomas et al., Am. Heart J. 2010, 160, 744-751; Berry et al., N. Eng. J. Med. 2012, 366, 321-329) suggesting there are yet-to-be identified factors accounting for this racial disparity.

Unexpectedly, the inventor has discovered that black patients exhibit greater platelet activity than white patients in response to PAR4 activation. Due to the greater platelet activity in black patients, the PC-TP inhibitors as described herein may have a more enhanced effect in black patients than in white patients for the prevention or treatment of pathologic thrombosis. Accordingly, when a PC-TP inhibitor is administered to a patient for the prevention or treatment of pathologic thrombosis or a disorder more common in blacks (e.g., sarcoidosis) and treatable by a PAR4 inhibitor, consideration regarding dosage and the regimen should be given based on the race of the patient in order to maximize the therapeutic effect for each patient.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 as determined in cell culture, or in an appropriate animal model. Levels in plasma can be measured, for example, by high performance liquid chromatography. The effects of any particular dosage can be monitored by a suitable bioassay specific for the disease. The dosage can be determined by a physician and adjusted, as necessary, to suit observed effects of the treatment.

Some embodiments of the invention are listed in the following paragraphs:

Paragraph 1. A method of preventing pathologic thrombosis, treating pathologic thrombosis, or treating a disorder treatable by a protease-activated receptor-4 (PAR4) inhibitor in a subject in need thereof, comprising administering a phosphatidylcholine transfer protein (PC-TP) inhibitor to said subject.

Paragraph 2. The method of paragraph 1, wherein the PC-TP inhibitor inhibits PAR4 activation.

Paragraph 3. The method of paragraph 1 or 2, wherein the PC-TP inhibitor is selected from compounds of Formula I:

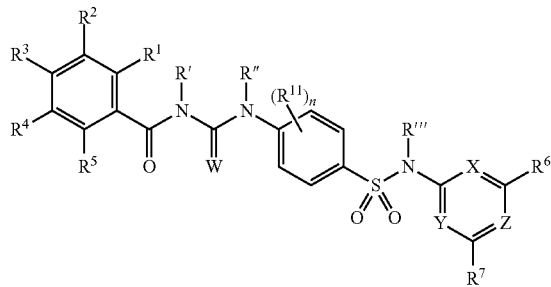

Formula I or a pharmaceutically acceptable salt thereof; wherein:
X is N or $CR^8$;
Y is N or $CR^9$;
Z is N or $CR^{10}$;
W is O;
R', R'', and R''' are each independently selected from H and $C_{1-4}$ alkyl; wherein said $C_{1-4}$ alkyl is optionally substituted by di-$C_{1-6}$-alkylamino;
$R^1$, $R^2$, $R^3$, $R^4$, and $R^5$ are each independently selected from H, halogen, cyano, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{a'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{a''}$ groups;
or $R^1$ and $R^2$, together with the carbon atoms to which they are attached, form a phenyl or $C_{1-6}$ heteroaryl ring, which is optionally substituted with 1, 2, 3, or 4 independently selected $R^{a''}$ groups;
or $R^2$ and $R^3$, together with the carbon atoms to which they are attached, form a phenyl or $C_{1-6}$ heteroaryl ring, which is optionally substituted with 1, 2, 3, or 4 independently selected $R^{a''}$ groups;
or $R^3$ and $R^4$, together with the carbon atoms to which they are attached, form a phenyl or $C_{1-6}$ heteroaryl ring, which is optionally substituted with 1, 2, 3, or 4 independently selected $R^{a''}$ groups;
$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{b'}$ groups;
and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$- alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{b''}$ groups;

or $R^6$ and $R^8$, together with the carbon atoms to which they are attached, form a phenyl or $C_{1-6}$ heteroaryl ring, which is optionally substituted with 1, 2, 3, or 4 independently selected $R^{b''}$ groups;

or $R^6$ and $R^{10}$, together with the carbon atoms to which they are attached, form a phenyl or $C_{1-6}$ heteroaryl ring, which is optionally substituted with 1, 2, 3, or 4 independently selected $R^{b''}$ groups;

or $R^7$ and $R^9$, together with the carbon atoms to which they are attached, form a phenyl or $C_{1-6}$ heteroaryl ring, which is optionally substituted with 1, 2, 3, or 4 independently selected $R^{b''}$ groups;

or $R^7$ and $R^{10}$, together with the carbon atoms to which they are attached, form a phenyl or $C_{1-6}$ heteroaryl ring, which is optionally substituted with 1, 2, 3, or 4 independently selected $R^{b''}$ groups;

each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

each $R^{a'}$ and $R^{b'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino;

each $R^{a''}$ and $R^{b''}$ is independently selected from halogen, cyano, nitro, hydroxyl, carboxyl, amino, $C_{1-4}$ alkyl, $C_{1-4}$ haloalkyl, $C_{1-4}$ alkoxy, $C_{1-4}$ haloalkoxy, $C_{1-4}$ alkylamino, and di-$C_{1-4}$-alkylamino; and n is an integer selected from 0, 1, 2, 3, and 4;

provided that:
(1) when the compound has Formula I, W is O, Z is CH, n is 0, $R^1$, $R^2$, $R^4$, $R^5$, $R^6$ and $R^7$ are each H, and either X is N and Y is CH, or X is CH and Y is N, then $R^3$ is other than chloro; and
(2) when the compound has Formula I, W is O, X is N, Y is N, and Z is $CR^{10}$, then the following provisos apply:
(a) when $R^6$ and $R^7$ are each methyl or each H, $R^{10}$ is H, and $R^1$, $R^2$, $R^4$, and $R^5$ are H, then $R^3$ is not methoxy or chloro; and (b) when $R^6$ and $R^7$ are each methyl or each H and $R^{10}$ is H, then at least one of $R^1$, $R^2$, $R^3$, $R^4$, and $R^5$ is other than H.

Paragraph 4. The method of paragraph 3, wherein the PC-TP inhibitor is selected from:
2,4-dichloro-N-(4-(N-(4,6-dimethylpyrimidin-2-yl)sulfamoyl)phenylcarbamoyl)-benzamide (LDN-193,188);
2-chloro-N-(4-(N-(4,6-dimethylpyrimidin-2-yl)sulfamoyl)phenylcarbamoyl)benzamide;
2,4-dichloro-N-(4-(N-(4,6-dimethylpyridin-2-yl)sulfamoyl)phenylcarbamoyl)benzamide;
2,3-dichloro-N-(4-(N-(4,6-dimethylpyrimidin-2-yl)sulfamoyl)phenylcarbamoyl)-benzamide;
3,4-dichloro-N-(4-(N-(4,6-dimethylpyrimidin-2-yl)sulfamoyl)phenylcarbamoyl)-benzamide;
2,4-dichloro-N-(4-(N-(4,6-dimethylpyrimidin-2-yl)sulfamoyl)phenyl)(methyl)carba-moyl)benzamide;
2,4-dichloro-N-(4-(N-(4,6-dimethylpyrimidin-2-yl)-N-methylsulfamoyl)phenyl-carbamoyl)benzamide;
2,4-dichloro-N-(4-(N-(2,6-dimethylpyrimidin-4-yl)sulfamoyl)phenylcarbamoyl)-benzamide;
2,4-dichloro-N-(4-(N-(3,5-dimethylphenyl)sulfamoyl)phenylcarbamoyl)benzamide;
and 2,4-dichloro-N-(4-(N-(4,6-dimethylpyrimidin-2-yl)sulfa-moyl)phenylcarbamoyl)-N-methylbenzamide;
or a pharmaceutically acceptable salt thereof.

Paragraph 5. The method of paragraph 4, wherein the PC-TP inhibitor is 2,4-dichloro-N-(4-(N-(4,6-dimethylpyrimidin-2-yl)sulfamoyl)phenylcarbamoyl)-benzamide (LDN-193, 188), or a pharmaceutically acceptable salt thereof.

Paragraph 6. The method of any of paragraphs 1 to 5, wherein the disorder treatable by a PAR4 inhibitor is selected from hepatitis, primary sclerosing cholangitis, sarcoidosis, inflammatory bowel disease, pancreatitis, thyroiditis, and fetal development disorders caused by placental dysfunction.

Paragraph 7. The method of any of paragraphs 1 to 6, wherein said subject is a mammal.

Paragraph 8. The method of paragraph 7, wherein said mammal is a human.

Paragraph 9. The method of any of paragraphs 1 to 8, further comprising administering a PAR1 inhibitor.

Paragraph 10. A method of inhibiting platelet activation, the method comprising contacting a platelet with a PC-TP inhibitor.

Paragraph 11. The method of paragraph 10, wherein the PC-TP inhibitor inhibits PAR4 activation.

Paragraph 12. The method of paragraph 10 or 11, wherein the PC-TP inhibitor is selected from compounds of Formula I:

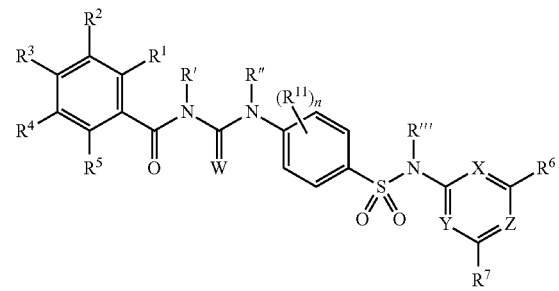

Formula I or a pharmaceutically acceptable salt thereof; wherein:
X is N or $CR^8$;
Y is N or $CR^9$;
Z is N or $CR^{10}$;
W is O;
R', R'', and R''' are each independently selected from H and $C_{1-4}$ alkyl; wherein said $C_{1-4}$ alkyl is optionally substituted by di-$C_{1-6}$-alkylamino;
$R^1$, $R^2$, $R^3$, $R^4$, and $R^5$ are each independently selected from H, halogen, cyano, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{a'}$ groups; and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{a''}$ groups;

or $R^1$ and $R^2$, together with the carbon atoms to which they are attached, form a phenyl or $C_{1-6}$ heteroaryl ring, which is optionally substituted with 1, 2, 3, or 4 independently selected $R^{a''}$ groups;

or $R^2$ and $R^3$, together with the carbon atoms to which they are attached, form a phenyl or $C_{1-6}$ heteroaryl ring, which is optionally substituted with 1, 2, 3, or 4 independently selected $R^{a''}$ groups;

or $R^3$ and $R^4$, together with the carbon atoms to which they are attached, form a phenyl or $C_{1-6}$ heteroaryl ring, which is optionally substituted with 1, 2, 3, or 4 independently selected $R^{a''}$ groups;

$R^6$, $R^7$, $R^8$, $R^9$, and $R^{10}$ are each independently selected from H, halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, $C_{1-6}$ alkylsulfonyl, $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl; wherein $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl are each optionally substituted by 1, 2, 3, or 4 independently selected $R^{b'}$ groups;

and wherein $C_{3-7}$ cycloalkyl, $C_{3-7}$ cycloalkyl-$C_{1-4}$-alkyl, $C_{2-14}$ heterocycloalkyl, $C_{2-7}$ heterocycloalkyl-$C_{1-4}$-alkyl, phenyl, phenyl-$C_{1-4}$-alkyl, $C_{1-6}$ heteroaryl, and $C_{1-6}$ heteroaryl-$C_{1-4}$-alkyl are each optionally substituted by 1, 2, 3, or 4 independently selected $R^{b''}$ groups;

or $R^6$ and $R^8$, together with the carbon atoms to which they are attached, form a phenyl or $C_{1-6}$ heteroaryl ring, which is optionally substituted with 1, 2, 3, or 4 independently selected $R^{b''}$ groups;

or $R^6$ and $R^{10}$, together with the carbon atoms to which they are attached, form a phenyl or $C_{1-6}$ heteroaryl ring, which is optionally substituted with 1, 2, 3, or 4 independently selected $R^{b''}$ groups;

or $R^7$ and $R^9$, together with the carbon atoms to which they are attached, form a phenyl or $C_{1-6}$ heteroaryl ring, which is optionally substituted with 1, 2, 3, or 4 independently selected $R^{b''}$ groups;

or $R^7$ and $R^{10}$, together with the carbon atoms to which they are attached, form a phenyl or $C_{1-6}$ heteroaryl ring, which is optionally substituted with 1, 2, 3, or 4 independently selected $R^{b''}$ groups;

each $R^{11}$ is independently selected from halogen, cyano, nitro, hydroxyl, carboxyl, carbamyl, amino, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ alkylamino, di-$C_{1-6}$-alkylamino, $C_{1-6}$ alkylcarbamyl, di-$C_{1-6}$ alkylcarbamyl, $C_{1-6}$ alkoxycarbonyl, $C_{1-6}$ alkylcarbonyl, $C_{1-6}$ alkylcarbonylamino, di-$C_{1-6}$ alkylcarbonylamino, $C_{1-6}$ alkylthio, $C_{1-6}$ alkylsulfinyl, and $C_{1-6}$ alkylsulfonyl;

each $R^{a'}$ and $R^{b'}$ is independently selected from halogen, cyano, nitro, hydroxyl, carboxyl, amino, $C_{1-4}$ alkoxy, $C_{1-4}$ haloalkoxy, $C_{1-4}$ alkylamino, and di-$C_{1-4}$-alkylamino;

each $R^{a''}$ and $R^{b''}$ is independently selected from halogen, cyano, nitro, hydroxyl, carboxyl, amino, $C_{1-4}$ alkyl, $C_{1-4}$ haloalkyl, $C_{1-4}$ alkoxy, $C_{1-4}$ haloalkoxy, $C_{1-4}$ alkylamino, and di-$C_{1-4}$-alkylamino; and n is an integer selected from 0, 1, 2, 3, and 4;

provided that:

(1) when the compound has Formula I, W is O, Z is CH, n is 0, $R^1$, $R^2$, $R^4$, $R^5$, $R^6$ and $R^7$ are each H, and either X is N and Y is CH, or X is CH and Y is N, then $R^3$ is other than chloro; and (2) when the compound has Formula I, W is O, X is N, Y is N, and Z is $CR^{10}$, then the following provisos apply: (a) when $R^6$ and $R^7$ are each methyl or each H, $R^{10}$ is H, and $R^1$, $R^2$, $R^4$, and $R^5$ are H, then $R^3$ is not methoxy or chloro; and (b) when $R^6$ and $R^7$ are each methyl or each H and $R^{10}$ is H, then at least one of $R^1$, $R^2$, $R^3$, $R^4$, and $R^5$ is other than H.

Paragraph 13. The method of paragraph 12, wherein the PC-TP inhibitor is selected from:

2,4-dichloro-N-(4-(N-(4,6-dimethylpyrimidin-2-yl)sulfamoyl)phenylcarbamoyl)-benzamide (LDN-193,188);

2-chloro-N-(4-(N-(4,6-dimethylpyrimidin-2-yl)sulfamoyl)phenylcarbamoyl)benzamide;

2,4-dichloro-N-(4-(N-(4,6-dimethylpyridin-2-yl)sulfamoyl)phenylcarbamoyl)benzamide;

2,3-dichloro-N-(4-(N-(4,6-dimethylpyrimidin-2-yl)sulfamoyl)phenylcarbamoyl)-benzamide;

3,4-dichloro-N-(4-(N-(4,6-dimethylpyrimidin-2-yl)sulfamoyl)phenylcarbamoyl)-benzamide;

2,4-dichloro-N-(4-(N-(4,6-dimethylpyrimidin-2-yl)sulfamoyl)phenyl)(methyl)carba-moyl)benzamide;

2,4-dichloro-N-(4-(N-(4,6-dimethylpyrimidin-2-yl)-N-methylsulfamoyl)phenyl-carbamoyl)benzamide;

2,4-dichloro-N-(4-(N-(2,6-dimethylpyrimidin-4-yl)sulfamoyl)phenylcarbamoyl)-benzamide;

2,4-dichloro-N-(4-(N-(3,5-dimethylphenyl)sulfamoyl)phenylcarbamoyl)benzamide;

and 2,4-dichloro-N-(4-(N-(4,6-dimethylpyrimidin-2-yl)sulfa-moyl)phenylcarbamoyl)-N-methylbenzamide;

or a pharmaceutically acceptable salt thereof.

Paragraph 14. The method of paragraph 13, wherein the PC-TP inhibitor is 2,4-dichloro-N-(4-(N-(4,6-dimethylpyrimidin-2-yl)sulfamoyl)phenylcarbamoyl)-benzamide (LDN-193,188), or a pharmaceutically acceptable salt thereof.

Paragraph 15. The method of any of paragraphs 10 to 14, wherein said contacting is in vitro.

Paragraph 16. The method of any of paragraphs 10 to 14, wherein said contacting is in vivo.

Paragraph 17. The method of paragraph 16, wherein said in vivo contacting is in a subject in need of prevention or treatment for pathologic thrombosis, or treatment for a disorder treatable by a PAR4 inhibitor.

Paragraph 18. The method of paragraph 17, wherein the disorder treatable by a PAR4 inhibitor is selected from hepatitis, primary sclerosing cholangitis, sarcoidosis, inflammatory bowel disease, pancreatitis, thyroiditis, and fetal development disorders caused by placental dysfunction.

Paragraph 19. The method of paragraph 17 or 18, wherein said subject is a mammal.

Paragraph 20. The method of paragraph 19, wherein said mammal is a human.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used herein, the term "pharmaceutically-acceptable salts" refers to the conventional nontoxic salts or quaternary ammonium salts of therapeutic agents, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like.

The terms "disease", "disorder", and "condition" are used interchangeably herein, and refer to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, affectation.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased morbidity or mortality. The term "treatment" of a disease also includes providing relief from the symptoms or side-effects of the disease (including palliative treatment).

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection. The administration can be systemic or local.

The terms "decrease", "reduced", "reduction", or "inhibit" are all used herein to mean a decrease by a statistically significant amount. In some embodiments, the terms "reduced", "reduction", "decrease", or "inhibit" can mean a decrease by at least 10% as compared to a reference level, for example a decrease by at least about 20%, or at least about 30%, or at least about 40%, or at least about 50%, or at least about 60%, or at least about 70%, or at least about 80%, or up to between about 90-95% or 90-99% decrease or any decrease of at least 10%-95% or 10-99% as compared to a reference level.

The term "statistically significant" or "significantly" refers to statistical significance and generally means a two standard deviation (2SD) or greater difference.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

As used herein, a "subject" means a human or animal. Usually the animal is a vertebrate such as, but not limited to a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. A subject can be male or female. Additionally, a subject can be an infant or a child.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with thrombosis. In addition, the methods and compositions described herein can be used for domesticated animals and/or pets. A human subject can be of any age, gender, race or ethnic group, e.g., Caucasian (white), Asian, African, black, African American, African European, Hispanic, Mideastern, etc. . . . . In some embodiments, the subject can be a patient or other subject in a clinical setting. In some embodiments, the subject can already be undergoing treatment.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9). Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

As used herein, the phrase "optionally substituted" means unsubstituted or substituted. As used herein, the term "substituted" means that a hydrogen atom is removed and replaced by a substitutent. It is understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, or 1 to 4 carbon atoms. Examples of alkyl moieties include, but are not limited to, chemical groups such as methyl, ethyl, n-propyl, isopropyl, n-butyl, tert-butyl, isobutyl, sec-butyl, 2-methyl-1-butyl, n-pentyl, 3-pentyl, n-hexyl, 1,2,2-trimethylpropyl, n-heptyl, n-octyl, and the like.

As used herein, "$C_{n-m}$ alkenyl", employed alone or in combination with other terms, refers to an alkyl group having one or more double carbon-carbon bonds and n to m carbon atoms. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl", employed alone or in combination with other terms, refers to an alkyl group having one or more triple carbon-carbon bonds, which may also optionally have one or more double carbon-carbon bonds, and having n to m carbon atoms. In some embodiments, the alkynyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, the term "$C_{n-m}$ alkoxy", employed alone or in combination with other terms, refers to an group of formula —O-alkyl, having n to m carbon atoms. Example alkoxy groups include methoxy, ethoxy, propoxy (e.g., n-propoxy or isopropoxy), t-butoxy, and the like.

As used herein, the term "amino", employed alone or in combination with other terms, refers to a group of formula —$NH_2$.

As used herein, the term "$C_{n-m}$ alkylamino", employed alone or in combination with other terms, refers to a group of formula —NH(alkyl), wherein the alkyl group has n to m carbon atoms. In some embodiments, the alkyl group has 1 to 6, 1 to 4, or 1 to 3 carbon atoms.

As used herein, the term "di-$C_{n-m}$ alkylamino", employed alone or in combination with other terms, refers to a group of formula —N(alkyl)$_2$, wherein each alkyl group independently has n to m carbon atoms. In some embodiments, each alkyl group has 1 to 6, 1 to 4, or 1 to 3 carbon atoms.

As used herein, the term "$C_{n-m}$ alkoxycarbonyl", employed alone or in combination with other terms, refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl", employed alone or in combination with other terms, refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylthio", employed alone or in combination with other terms, refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl", employed alone or in combination with other terms, refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl", employed alone or in combination with other terms, refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbamyl", employed alone or in combination with other terms, refers to a group of formula —C(O)NH-alkyl, wherein the alkyl group has n to m carbon atoms. In some embodiments, the alkyl group has 1 to 6, 1 to 4, or 1 to 3 carbon atoms.

As used herein, the term "di-$C_{n-m}$ alkylcarbamyl", employed alone or in combination with other terms, refers to a group of formula —C(O)N(alkyl)$_2$, wherein each alkyl group independently has n to m carbon atoms. In some embodiments, each alkyl group has 1 to 6, 1 to 4, or 1 to 3 carbon atoms. As used herein, the term "$C_{n-m}$ alkylcarbonylamine", employed alone or in combination with other terms, refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "di-$C_{n-m}$ alkylcarbonylamine", employed alone or in combination with other terms, refers to a group of formula —N(alkyl)C(O)-alkyl, wherein each alkyl group independently has n to m carbon atoms. In some embodiments, each alkyl group has 1 to 6, 1 to 4, or 1 to 3 carbon atoms.

As used herein, the term "carbamyl", employed alone or in combination with other terms, refers to a —C(O)NH$_2$ group.

As used herein, the term "carbonyl", employed alone or in combination with other terms, refers to a —C(O)— group.

As used herein, the term "carboxy", employed alone or in combination with other terms, refers to a group of formula —C(O)OH.

As used herein, the term "cyano", employed alone or in combination with other terms, refers to a group of formula —CN.

As used herein, the terms "halo" and "halogen", employed alone or in combination with other terms, refer to fluoro, chloro, bromo, and iodo. In some embodiments, halogen is fluoro.

As used herein, the term "$C_{n-m}$ haloalkyl", employed alone or in combination with other terms, refers to an alkyl group having from n to m carbon atoms and one halogen atom to 2x+1 halogen atoms which may be the same or different, where "x" is the number of carbon atoms in the alkyl group. In some embodiments, the halogen atoms are fluoro atoms. In some embodiments, the alkyl group has 1 to 6 or 1 to 4 carbon atoms. An example of a haloalkyl group is —CF$_3$.

As used herein, "$C_{n-m}$ haloalkoxy", employed alone or in combination with other terms, refers to a group of formula —O-haloalkyl, wherein the haloalkyl group has n to m carbon atoms. In some embodiments, the alkyl group has 1 to 6 or 1 to 4 carbon atoms. An example haloalkoxy group is —OCF$_3$.

As used herein, the term "$C_{n-m}$ cycloalkyl", employed alone or in combination with other terms, refers to a non-aromatic cyclic hydrocarbon moiety, which may optionally contain one or more alkenylene or alkynylene groups as part of the ring structure, and which has n to m ring member carbon atoms. Cycloalkyl groups can include mono- or polycyclic (e.g., having 2, 3, or 4 fused, bridged, or spiro rings) ring systems. The term "cycloalkyl" also includes bridgehead cycloalkyl groups and spirocycloalkyl groups. As used herein, "bridgehead cycloalkyl groups" refers to non-aromatic cyclic hydrocarbon moieties containing at least one bridgehead carbon, such as admantan-1-yl. As used herein, "spirocycloalkyl groups" refers to non-aromatic hydrocarbon moieties containing at least two rings fused at a single carbon atom, such as spiro[2.5]octane and the like. In some embodiments, the cycloalkyl group has 3 to 14 ring members, 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. One or more ring-forming carbon atoms of a cycloalkyl group can be oxidized to form carbonyl linkages. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is admanatan-1-yl.

As used herein, the term "$C_{n-m}$ cycloalkylene" refers to a divalent cycloalkyl group having n to m carbon atoms.

As used herein, the term "$C_{n-m}$ cycloalkyl-Co-p alkyl", employed alone or in combination with other terms, refers to a group of formula -alkylene-cycloalkyl, wherein the cycloalkyl portion has n to m carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the cycloalkyl portion has 3 to 14 ring members, 3 to 10 ring members, or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "x-membered cycloalkyl ring" refers to a monocyclic cycloalkyl ring having x ring members.

As used herein, the term "$C_{n-m}$ heterocycloalkyl", "$C_{n-m}$ heterocycloalkyl ring", or "$C_{n-m}$ heterocycloalkyl group", employed alone or in combination with other terms, refers to non-aromatic ring or ring system, which may optionally contain one or more alkenylene or alkynylene groups as part of the ring structure, which has at least one heteroatom ring member independently selected from nitrogen, sulfur and oxygen, and which has n to m ring member carbon atoms. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 hetereoatoms independently selected from nitrogen, sulfur and oxygen. Also included in the definition of heterocycloalkyl are moieties that have one or more aromatic rings (e.g., heteroaryl or aryl rings) fused (e.g., having a bond in common with) to the non-aromatic ring, for example, 1,2,3,4-tetrahydro-quinoline and the like. Heterocycloalkyl groups can also include bridgehead heterocycloalkyl groups and spiroheterocycloalkyl groups. As used herein, "bridgehead heterocycloalkyl group" refers to a heterocycloalkyl moiety containing at least one bridgehead atom, such as azaadmantan-1-yl and the like. As used herein, "spiroheterocycloalkyl group" refers to a heterocycloalkyl moiety containing at least two rings fused at a single atom, such as [1,4-dioxa-8-aza-spiro[4.5]decan-N-yl] and the like. In some embodiments, the heterocycloalkyl group has 3 to 20 ring-forming atoms, 3 to 10 ring-forming atoms, or about 3 to 8 ring forming atoms. The carbon atoms or hetereoatoms in the ring(s) of the heterocycloalkyl group can be oxidized to form a carbonyl, or sulfonyl group (or other oxidized linkage) or a nitrogen atom can be quaternized. In some embodiments, the heterocycloalkyl portion is a $C_{2-7}$ monocyclic heterocycloalkyl group.

As used herein, the term "x-membered heterocycloalkyl ring" refers to a monocyclic heterocycloalkyl ring having x ring members.

As used herein, the term "$C_{n-m}$ heterocycloalkyl-Ca alkyl", employed alone or in combination with other terms, refers to a group of formula -alkylene-heterocycloalkyl, wherein the heterocycloalkyl portion has n to m carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the heterocycloalkyl portion has 3 to 14 ring members, 3 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "$C_{n-m}$ aryl", employed alone or in combination with other terms, refers to a monocyclic or polycyclic (e.g., having 2, 3 or 4 fused rings) aromatic hydrocarbon moiety having n to m ring member carbon atoms, such as, but not limited to, phenyl, 1-naphthyl, 2-naphthyl, anthracenyl, phenanthrenyl, and the like. Also included in the definition of aryl are moieties that have one or more cycloalkyl or heterocycloalkyl rings fused (i.e., having a bond in common with) to the aryl ring. In some embodiments, aryl groups have from 6 to 14 carbon atoms, about 6 to 10 carbon atoms, or about 6 carbons atoms. In some embodiments, the aryl group is a monocyclic or bicyclic group.

As used herein, the term "$C_{n-m}$ aryl-Co-p-alkyl", employed alone or in combination with other terms, refers to a group of formula -alkylene-aryl, wherein the aryl portion has n to m ring member carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the aryl portion is phenyl. In some embodiments, the aryl group is a monocyclic or bicyclic group. In some embodiments, the arylalkyl group is benzyl.

As used herein, the term "$C_{n-m}$ heteroaryl", "$C_{n-m}$ heteroaryl ring", or "$C_{n-m}$ heteroaryl group", employed alone or in combination with other terms, refers to a monocyclic or polycyclic (e.g., having 2, 3 or 4 fused rings) aromatic hydrocarbon moiety, having one or more heteroatom ring members independently selected from nitrogen, sulfur and oxygen and having n to m ring member carbon atoms. Also included in the definition of heteroaryl are moieties that have one or more cycloalkyl or heterocycloalkyl rings fused (i.e., having a bond in common with) to the aryl ring. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyrrolyl, azolyl, oxazolyl, thiazolyl, imidazolyl, furyl, thienyl, quinolinyl, isoquinolinyl, indolyl, benzothienyl, benzofuranyl, benzisoxazolyl, imidazo[1,2-b]thiazolyl or the like. The carbon atoms or hetereoatoms in the ring(s) of the heteroaryl group can be oxidized to form a carbonyl, or sulfonyl group (or other oxidized linkage) or a nitrogen atom can be quaternized, provided the aromatic nature of the ring is preserved for at least one ring of the heteroaryl moiety. In some embodiments, the heteroaryl group has 5 to 10 carbon atoms.

As used herein, the term "x-membered heteroaryl ring" refers to a monocyclic heteroaryl ring having x ring members.

As used herein, the term "$C_{n-m}$ heteroaryl-Co-p-alkyl", employed alone or in combination with other terms, refers to a group of formula -alkylene-heteroaryl, wherein the heteroaryl portion has n to m ring member carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the heteroaryl portion is a monocyclic or bicyclic group having 1, 2, 3, or 4 hetereoatoms independently selected from nitrogen, sulfur and oxygen. In some embodiments, the heteroaryl portion has 5 to 10 carbon atoms.

As used herein, the term "oxo" refers to a group of formula "=O".

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1: Racial Difference in Human Platelet PAR4 Reactivity Reflects Expression of PC-TP and miR-376c Methods Subjects.

Platelet RNA And eXpression-1 (PRAX1) study was approved by the Institutional Review Boards of Thomas Jefferson University and Baylor College of Medicine, and informed consent was obtained from all volunteers. Only healthy, non-diabetic subjects who self-identified their race as white or black, using no anti-platelet medications were eligible for this study. Black and white subjects were recruited randomly throughout the duration of the study. Donors were recruited from 2010-2011 in Houston, Tex., and in 2013 in Philadelphia, Pa., and blood was collected as previously described (Yee et al., Blood 2005, 106, 2723-2729).

Platelet Function Assessment.

(1) Houston studies. A complete blood count and mean platelet volume were obtained using an ABX Micros 60 CS (Horiba ABX, Irvine, Calif., USA). Using light transmission aggregometry, maximal percent aggregation and slope of aggregation at 10 min in platelet rich plasma (PRP) treated with: 0.5 mg/ml arachidonic acid, 4 µM ADP, 1 µM and 2 µM PAR1 activating peptide (PAR1-AP), and 50 µM and 75 µM PAR4 activating peptide (PAR4-AP) were measured. (2) Philadelphia studies. Light transmission aggregometry of washed platelets was used to assess thrombin-induced platelet aggregation without or with a 2 min pre-incubation with 20 µM BMS-200261 (BMS, PAR1-specific antagonist) (Quinton et al., J. Biol. Chem. 2004, 279, 18434-18439). A difference in the efficacy of the PAR1 inhibitor was observed between the pilot and replicate studies, but validation of inhibitor activity was confirmed for both studies (FIG. 1B inset and FIG. 7E). For assessment of calcium mobilization, platelets were re-calcified to a final concentration of 1 mM followed by pre-incubation with Fluo-4 AM for 10 min. The platelets were then stimulated with PAR4-AP and calcium mobilization was measured using the Accuri C6 flow cytometer (Yeung et al., Mol. Pharmacol. 2012, 81, 420-430). In both Houston and Philadelphia, technical variation was minimized by use of the same highly-trained technicians, same lots of reagents and same instruments throughout the duration of the study. Because multiple concentrations were used to activate PAR1 and PAR4 to induce platelet aggregation, an integrated score was developed that combined these values to determine a single index that represented each individual's agonist response. This score correlated strongly with standard assessment of maximal percent aggregation, but inclusion of slope (which was a minor contributor to the overall score, and highly related to maximal aggregation) allowed distinction among platelets with the same maximal aggregation value. This score was highly reproducible in 10 subjects studied weekly for three or four weeks.

Plasma Assays.

Plasma fibrinogen level and von Willebrand factor activity were measured on an ACL TOP 500 (Instrumentation Laboratories, Bedford, Mass.) as per manufacturer's instructions.

Cell Lines.

Meg-01 and HEL cells were obtained from ATCC (Manassas, Va.) where they are authenticated before distribution. HCT116-Dicer KO 2 cells were authenticated for Dicer deficiency. Cell lines were not tested for *mycoplasma*.

Measurement of $Ca^{2+}$ Mobilization.

Twenty-four hours before transfection, Meg-01 cells (ATCC, Manassas, Va.) were plated at $1 \times 10^6$ cells/well in 6-wells plates with RPMI 1640 media supplemented with 10% FBS without antibiotics. Cells were transfected with either human PC-TP siRNA-SMART pool or non-targeting siRNA control (ThermoFisher Scientific, Waltham, Mass.) by using Lipofectamine RNAiMAX (Invitrogen) according to the manufacturer's instructions. Cells were harvested 48 h after transfection and western-blot, qRT-PCR, and flow cytometry assays were performed. To monitoring $Ca^{2+}$ mobilization under agonist stimulation, cells were washed, pre-incubated with Fluo-4-AM (Invitrogen), recalcified and stimulated with 250 µM PAR4-AP or 50 µM PAR1-AP (Yeung et al., Mol. Pharmacol. 2012, 81, 420-430). Changes in Meg-01 $Ca^{2+}$ concentration over time were monitored using an Accuri C6 flow cytometer.

Platelet mRNA Profiling.

Leukocyte depleted platelets (LDP) RNA were prepared by density centrifugation and immune-depletion of CD45+ cells as previously described, yielding less than 1 leukocyte per 5 million platelets (Nagalla et al., Blood 2011, 117, 5189-5197). RNA was extract with TRIzol® (Life Technologies, Carlsbad, Calif.). Technical variation was minimized by use of the same highly-trained technicians, same lots of reagents and same instruments throughout the duration of the study. All RNA samples were subject to quality control screening using an Agilent Bioanalyzer. 300 ng of LDP total RNA was labeled and hybridized to the Human Gene 1.0 ST Array (Affymetrix, Santa Clara, Calif.). For mRNA data pre-processing, "apt-probeset-summarize" from the Affymetrix Power Tools was used for background subtraction, normalization and summarizing probeset values from Affymetrix Gene array. The background adjustment was done with the Robust-Multi-array average technique. The raw intensity values were background corrected, log 2 transformed and then quantile normalized (the command line option was "-a rma-sketch") similar to prior analysis (Fryer et al., Science 2011, 334, 690-693). Data deposited into NCBI GeneExpressionOmnibus.

Platelet miRNA Profiling.

Digital miRNA profiling from 100 ng of LDP total RNA was performed using the nCounter human miRNA assay kit v1 (Nanostring Technologies, Seattle, Wash.) that counts miRNAs without amplification and produces high sensitivity and specificity allowing accurate comparisons of individual miRNA species within and between samples. In brief, a color-coded reporter probe and a capture probe are hybridized, in solution to target molecules. The captured molecules are then attached to a streptavidin-coated slide and then elongated and aligned via electrophoresis. Finally, the color-coded reporter probes are counted. This technology has the advantage over standard microarray hybridization profiling of avoiding the biasing effects of RNA amplification and of direct measurement of the number of molecules detected and demonstrates linearity over 2.5 logs of concentration (Geiss et al., Nat. Biotechnol. 2008, 26, 317-325). Total RNA is hybridized in solution to reporter probes labeled with fluorescent bar codes. Via capture probes, the hybridized miRNAs adhere to a solid surface and the number of bar codes was counted. Expression levels of well characterized and validated human (n=654) and human-associated viral miRNAs (n=80) were determined. To control for technical differences, the data was normalized using spike-in positive controls. To account for loading differences in miRNA content, the data was further normalized to total number of miRNA counts in each sample. Background detection threshold was set as the average plus two standard deviations of eight negative control probes. Notably, the values obtained in the data fell within the linearity of the Nanostring assay. Data deposited into NCBI GeneExpressionOmnibus.

Validation of RNA Expression, and miRNA Knockdown.

HCT-116-Dicer-KO cell line was grown in McCoy's 5A medium (Life Technologies, Carlsbad, Calif.); Meg-01 and HEL cells were grown in RPMI medium (Life Technologies) adjusted to contain 10% (v/v) fetal bovine serum. Cells were seeded 24 hours before transfection in 6-well plates without antibiotics. To validate miR-376c knock down of PC-TP, HCT115-Dicer-KO cells were transfected with 20-80 nM of pre-miR-376c or scrambled control (Life Technologies). Meg-01 and HEL cell lines were transfected with 100 nM of pre-miR-376c or scrambled control (Life Technologies), as well as hsa-miR-376c miRCURY LNA™ microRNA inhibitor or miRCURY LNA™ microRNA Inhibitor Negative Control (Exiqon, Denmark) using Lipofectamine LTX (Life Technologies) transfection agent following the manufacturer's protocol. After 6 hours the media was replaced. HCT-116-Dicer-KO cells were harvested 6 h, 24 h and 48 hours after transfection. Meg-01 and HEL cell lines were harvested 48 hours after transfection. Total RNA was isolated using Trizol® Reagent (Ambion). To validate relative expression levels of miRNAs and mRNAs, qRT-PCR of PC-TP transcripts was performed via Power SYBR Green PCR master mix (Life Technologies, Carlsbad, Calif.), using the following primers 5'-AGAATGCAACGGAGAGACT-GTGGT-3' (SEQ ID NO: 1), 5'-TCACATGGATCTTCCTC-CCTTCCA-3' (SEQ ID NO: 2) and normalized to β-actin. Mature hsa-miR-376c, hsa-miR-376b, hsa-miR-410, hsa-miR-495 and let-7b levels were quantified using TaqMan® MicroRNA Reverse Transcription Kit, TaqMan® MicroRNA assays together with TaqMan® Universal PCR Master Mix, No AmpErase® UNG (Applied Biosystems). RNU6B expression was used to normalize miRNA expression. Real time PCR reaction and analyses were carried out in 384-well optical reaction plates using the 7900HT instrument (Applied Biosystems).

Western Blotting and Antibodies.

Leukocyte-depleted platelets were lysed and homogenized in 8 M urea buffer (8 M urea in 10 mM Tris, pH 6.8, 1% SDS, 5 mM DTT in the presence of a 1× protein inhibitor mix (Roche, Indianapolis, Ind.)). Extracts were separated by 12% SDS-PAGE and transferred onto PVDF membranes. Membranes were immunostained with goat anti-human PC-TP (N-20) polyclonal antibody sc-23672 and mouse anti-human GAPDH (FL-335) monoclonal antibody sc-25778 (Santa Cruz Biotechnology, Dallas, Tex.). Detection and densitometric analysis was performed with Odyssey Infrared Imaging System (Li-Cor, Lincoln, Nebr.).

Hematopoietic Stem Cell (HSC) Isolation and Differentiation to Megakaryocytes.

Cord blood was obtained from the New York Blood Center and diluted 1:2 with PBS and layered over His-topaque® (Sigma, St. Louis, Mo.). After 30 minutes centrifugation at 400×g the buffy coat was carefully collected. CD34+ cells were isolated using magnetic immunoselection (Miltenyi Biotec, Auburn, Calif.) following the manufacture's protocol. Cells were then cultured at $4\times10^5$ cells/well in a 24 well plate, with StemSpan™ media (StemCell Technologies, Vancouver, Canada) supplemented with 25 ng/mL SCF and 20 ng/mL thrombopoietin (TPO; Peprotech, Rocky Hill, N.J.). After day 6 the cultures were supplemented with 50 ng/mL TPO only. Every 3 days, the cells were harvested, counted and re-plated at $4\times10^5$ cells/well in a 24 well plate with fresh media. Megakaryocytic differentiation was monitored by flow cytometry, testing for CD34, CD41 and CD42. At day 16, cells were seeded onto a fibrinogen coated coverslip. Cells were stained with phalloidin-alexa-533 (Life Technologies), rabbit anti-human tubulin (Patel et al., J. Clin. Invest. 2005, 115, 3348-3354) and mouse anti-rabbit alexa-488 (Life Technologies). The coverslips were mounted on slides using ProLong® Gold Antifade Reagent with DAPI (Life Technologies). Images were captured using a Zeiss LSM 510 Meta Confocal Laser Scanning Microscope.

Statistical Analysis.

Before performing the study, sample size calculations using a linear model framework with Gaussian errors were performed using effect sizes and variance estimates based on previous work where genome wide expression profiling with purified platelet samples was performed (Nagalla et al., Blood 2011, 117, 5189-5197; Kondkar et al., J. Thromb. Haemost, 2010, 8, 369-378). This effort indicated 150 subjects would provide greater than 85% power to detect modeled associations between platelet agonist phenotypes and RNA expression levels. For continuous phenotype (response) data in this study, qq-plots were used to evaluate normality of errors about linear model fits. For binary count data, binomial sampling models were employed, and Fisher's Exact tests were used to evaluate associations, such as when testing the cross tabulation of those genes associated with PAR4 reactivity vs. those associated with self-identified race. Variance of PAR4 reactivity within each race was not found to be significantly different by an F-test of the variances (F=1.4, 95% CI: 0.87-2.15, P=0.2). Statistical analyses were performed using the open source statistical programming environment R (Gentleman et al., J. of Computational and Statistical Graphics 1996, 5, 299-314). Association analyses between platelet phenotype PAR4 and gene expression were performed using linear models. Multiple testing considerations were made using the False Discovery Rate (FDR) methodology, and q-values were estimated using the Benjamini-Hochberg method (Hochberg et al., Statistics in Medicine 1990, 9, 811-818) as made available through the R function p.adjust.

Principle Components Analysis (PCA).

PCA is a commonly used mathematical approach that allows an unbiased examination of population structure in large scale genotype data. PCA transforms high dimensional multimarker genotypes encoded as reference allele counts from many subjects into simple, low dimensional representations through projection to additive combinations of allele counts where the weights are the PCA loadings. This analysis permits identification of "structure" such as race in the data. This unbiased method was applied to the samples. DNA was extracted from buffy coat preparations from all PRAX subjects using the Gentra Puregene Blood Kit (Qiagen, Netherlands). DNA was hybridized to the HumanOmni5 array (Illumnia Inc., San Diego, Calif.) at the Laboratory for Translational Genomics at the Baylor College of Medicine. The Eigenstrat software package (Price et al., Nat. Genet. 2006, 38, 904-909) was used to compute the PCA transformation excluding the ethnicity information from the analysis.

Filters for Detected and Background Probes.

Eight subjects were excluded for presumed anti-platelet medication use (defined as arachidonic acid aggregation of <30%) and one subject was excluded because of abnormal hematological parameters, leaving 154 samples for all subsequent analyses. In both the miRNA and mRNA data, a two-step filter was used to determine which probes to consider as expressed in the samples for the purposes of downstream analyses. The distribution of mean values for each probe across subjects was first used to determine a cutoff that differentiated those features with background intensity from others. The number of individual subjects with values that exceeded this background cutoff was then counted. The count distribution for the number of subjects exceeding the background cutoff was bimodal, indicating that most probes are either almost always expressed or not in the cohort. To be considered commonly expressed, it was therefore required that at least 100 subjects express the miRNA above background and 115 subjects express the mRNA above background. For the mRNAs, it was also required that the probeset was of category 'main', as classified in HuGene-1_0-st-v1.na33.2.hg19.transcript.csv file (available from www.affymetrix.com/support/technical/annotationfilesmain.affx). A sensitivity analysis showed very little variation in the selected data based on small variations in the cut-point for expressed RNAs, and the method was also robust to small variations in the percentage cutoff for the number of people expressing each RNA.

Exploratory Analyses.

Exploratory cluster analyses were performed on the miRNA platelet expression data. Normalized log 2 transformed values of the 178 miRNAs above cutoff were centered and hierarchically clustered using Cluster 3.0 (original software by Michael Eisen (Eisen et al., PNAS 1998, 95, 14863-14868), updated by Michiel de Hoon (University of Tokyo, http://bonsai.hgc.jp/~mdehoon/software/cluster/software.htm)). A corresponding heatmap was created using Java Treeview. Pearson correlation coefficients were calculated for all 178 miRNAs above cutoff pairwise using the R statistical package.

Model Based Analyses.

In addition to cluster analyses, a series of correlative analyses was performed to examine the association between RNA expression and subject demographics, platelet agonist-induced aggregation and other hematologic parameters. These analyses included simple and multiple linear regressions, performed in R using analysis of variance (aov) tools that permit evaluation of multiple explanatory variables. In the analysis of the PAR4 phenotype, PAR4 reactivity was treated as the dependent variable and included the demographic covariates and RNA expression data as explanatory. A False Discovery approach was taken to account for possible false positives in the mRNA expression analysis, and the Benjamini-Hochberg linear step down method was used to control the FDR (Benjamini et al., J. R. Statist. Soc. 1995, 57, 289-300).

Network Analysis.

A network of miRNA-mRNA pairs was constructed using target predictions and allowing an edge only if miRNA and mRNA levels met the following criteria across the 154 subjects: 1) both the miRNA and mRNA are differentially expressed by race, 2) both the mRNA and miRNA correlate with PAR4-mediated platelet reactivity, 3) the miRNA is predicted to target the mRNA, 4) the RNA levels are inversely correlated with one another, and 5) the miRNAs reside in the DLK1-DIO3 region. The miRNA-mRNA pairs were then visualized using the Cytoscape software package.

Analysis of Racial SNV Allele Frequency and RNA Expression Probes.

To investigate the possibility that RNA expression differences observed between races could be mediated by SNV variation in the probes in the two expression assays used—Affymetrix Gene ST 1.0 and Nanostring—additional analyses of the expression data was performed using information from the 1000 Genomes project Genomes Project Consortium (A map of human genome variation from population-scale sequencing. Nature. 2010; 467: 1061-73.) as a reference. Data were obtained from the 1000 genomes website ftp://ftp.1000genomes.ebi.ac.uk/vol1/ftp/release/20100804/supporting/, in particular the files:

AFR.2of4intersection allele freq.20100804.genotypes.vcf.gz
AFR.2of4intersection allele freq.20100804.genotypes.vcf.gz.tbi,
EUR.2of4intersection allele freq.20100804.genotypes.vcf.gz
EUR.2of4intersection allele freq.20100804.genotypes.vcf.gz.tbi All 1 million+ probe sequence locations were then identified for probesets on the Affy GeneST 1.0 array and the miRNAs comprising the Nanostring assay. The locations of all SNVs (SNPs) in the thousand genomes data were identified that showed a significant difference in allele frequency between races (EUR and AFR) based on Fisher's exact test of allele frequency and a Fisher's Test p-value cutoff of 0.01, and all those expression probes that harbored a racially dimorphic SNP as defined by the Fisher's test criteria were identified. Analyses were then performed to consider their effect on the gene-level expression and miRNA expression results.

Results

Platelets from Black Subjects Demonstrate Enhanced Aggregation Through PAR4.

Ex vivo platelet aggregation testing was performed on 163 young, non-diabetic and generally healthy subjects. After exclusion due to use of anti-platelet medication or abnormal hematological parameters, 154 subjects were included for RNA profiling and analyses (Table 1). When comparing platelet function from the 70 blacks and 84 whites, no racial difference was observed in the average platelet maximal aggregation response to arachidonic acid, ADP, anti-CD9 antibody, collagen-related peptide or the PAR1 activation peptide (PAR1-AP), which activate platelets through the thromboxane, P2Y1/P2Y12, FcγRIIa, glycoprotein VI and PAR1 signaling receptors, respectively (FIG. 1A). However, aggregation in response to PAR4-AP, which activates platelets through the PAR4 thrombin receptor, was higher in platelets from blacks compared to white subjects (3.8-fold higher at 50 μM PAR4-AP [P<0.0001] and 1.4-fold higher at 75 μM PAR4-AP [P<0.0001]) (FIG. 1A; Table 2). Using an agonist response score (ARS) that allowed precise differentiation among subjects with the same maximal aggregation (defined in Methods), the racial difference in PAR4-mediated platelet aggregation was even stronger ($p=6.76 \times 10^{-9}$). Race was the dominant determinant of the PAR4 ARS when the racial differences in age, gender, body mass index (BMI) and platelet count (Table 1) were considered in a multiple linear regression analysis that controlled for these covariates in considering the contribution of race ($p=5.15\times10^{-8}$).

TABLE 1

Demographics and platelet parameters by race

| Characteristic | Black (n = 70) | White (n = 84) | P-Value |
|---|---|---|---|
| Age, years | 29.7 ± 7.2 | 27.7 ± 5.8 | 0.05 |
| % Female | 55.7 | 46.4 | 0.40 |
| Body mass index, kg/m$^2$ | 26.24 ± 5.9 | 24.53 ± 3.96 | 0.03 |
| % with hypertension | 3 | 1 | 0.61 |
| % Current Smokers | 7 | 14 | 0.18 |
| Platelet count, (10$^4$/μl) | 222 ± 74.3 | 198 ± 49.5 | 0.03 |
| Mean platelet fL | 7.27 ± 0.77 | 7.26 ± 0.70 | 0.92 |
| Fibrinogen (mg/dL) | 250 ± 52.9 | 251 ± 55.1 | 0.94 |
| VWF activity (%) | 108 ± 45.3 | 99 ± 35.6 | 0.17 |

Data are expressed as mean ± SD or percentages. Statistical tests were T-test for numerical variables and χ2 for nominal parameters.

TABLE 2

Summary of light transmission aggregometry statistics in PARX1

| | Black | | White | | Fold difference | p Value |
|---|---|---|---|---|---|---|
| Agonist | Mean* | SEM | Mean* | SEM | (Black/White) | (Mann Whitney) |
| 500 μg/ml AA | 86.57 | 1.35 | 87.21 | 1.28 | 0.99 | 0.52 |
| 4 μM ADP | 40.89 | 3.32 | 45.04 | 3.21 | 0.91 | 0.38 |
| 10 ng/ml CRP | 70.90 | 4.03 | 74.39 | 3.70 | 0.95 | 0.26 |
| 20 ng/ml CRP | 91.94 | 1.91 | 88.50 | 2.68 | 1.04 | 0.73 |
| 500 ng/ml anti-CD9 | 36.66 | 4.09 | 40.50 | 4.09 | 0.91 | 0.66 |
| 750 ng/ml anti-CD9 | 55.16 | 4.79 | 58.12 | 4.48 | 0.95 | 0.83 |
| 2000 ng/ml anti-CD9 | 70.76 | 4.57 | 62.36 | 4.59 | 1.13 | 0.30 |
| 1 μM PAR1-AP | 14.96 | 3.33 | 17.05 | 3.20 | 0.88 | 0.95 |
| 2 μM PAR1-AP | 76.91 | 3.07 | 79.89 | 2.11 | 0.96 | 0.95 |
| 50 μM PAR4-AP | 40.77 | 4.91 | 10.68 | 2.82 | 3.82 | 0.00 |
| 75 μM PAR4-AP | 79.04 | 3.38 | 55.63 | 4.21 | 1.42 | 0.00 |

*percent maximal aggregation

Figure 7A:
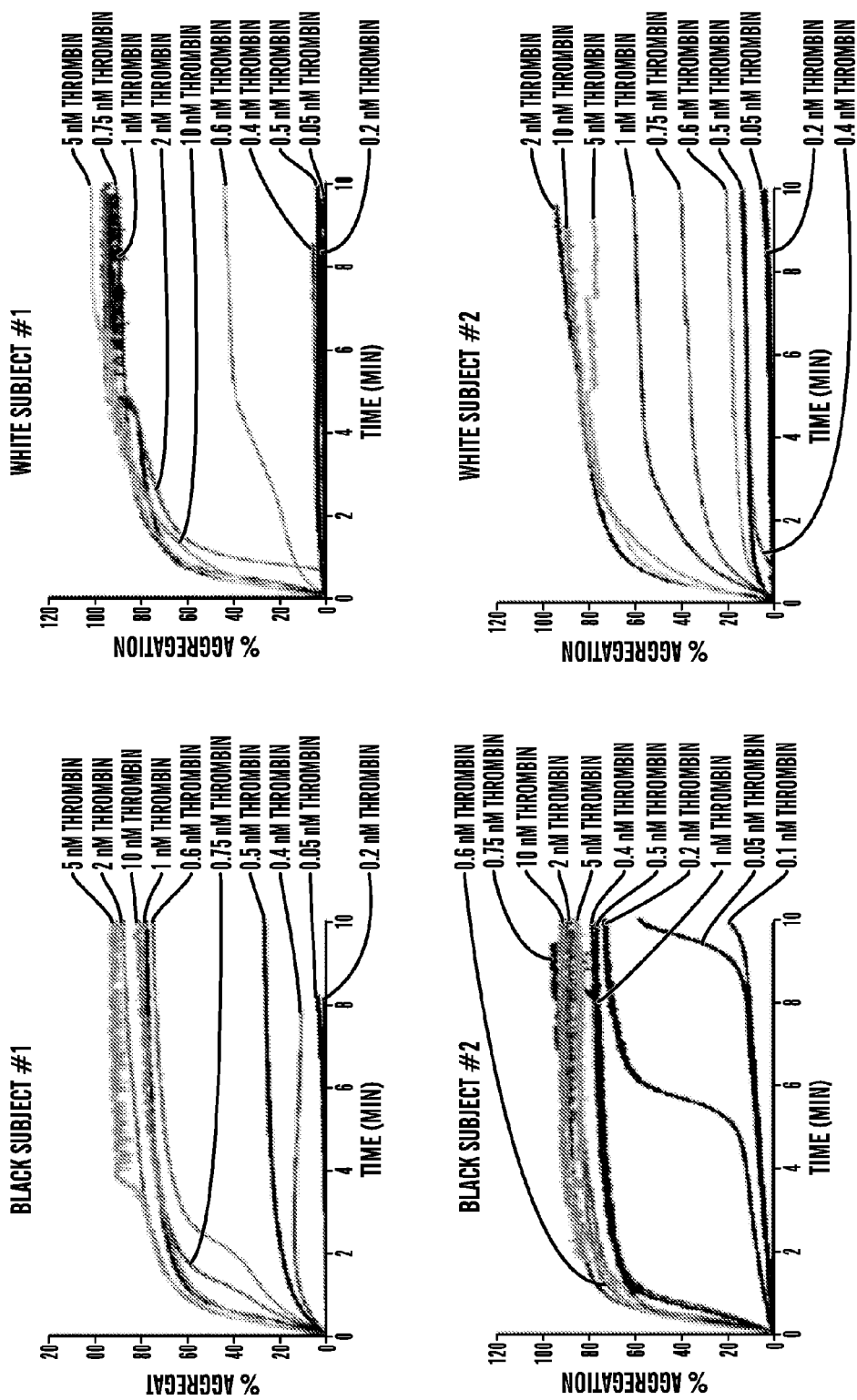
FIGS. 7A-7E show racial differences in platelet response to thrombin. LTA was measured in washed platelets following addition of multiple concentrations of thrombin in the absence (FIG. 7A) or presence (FIG. 7B) of 20 µM BMS-200261 (BMS, PAR1-specific antagonist) for 4 black subjects and 3 white subjects.
Figure 7A:
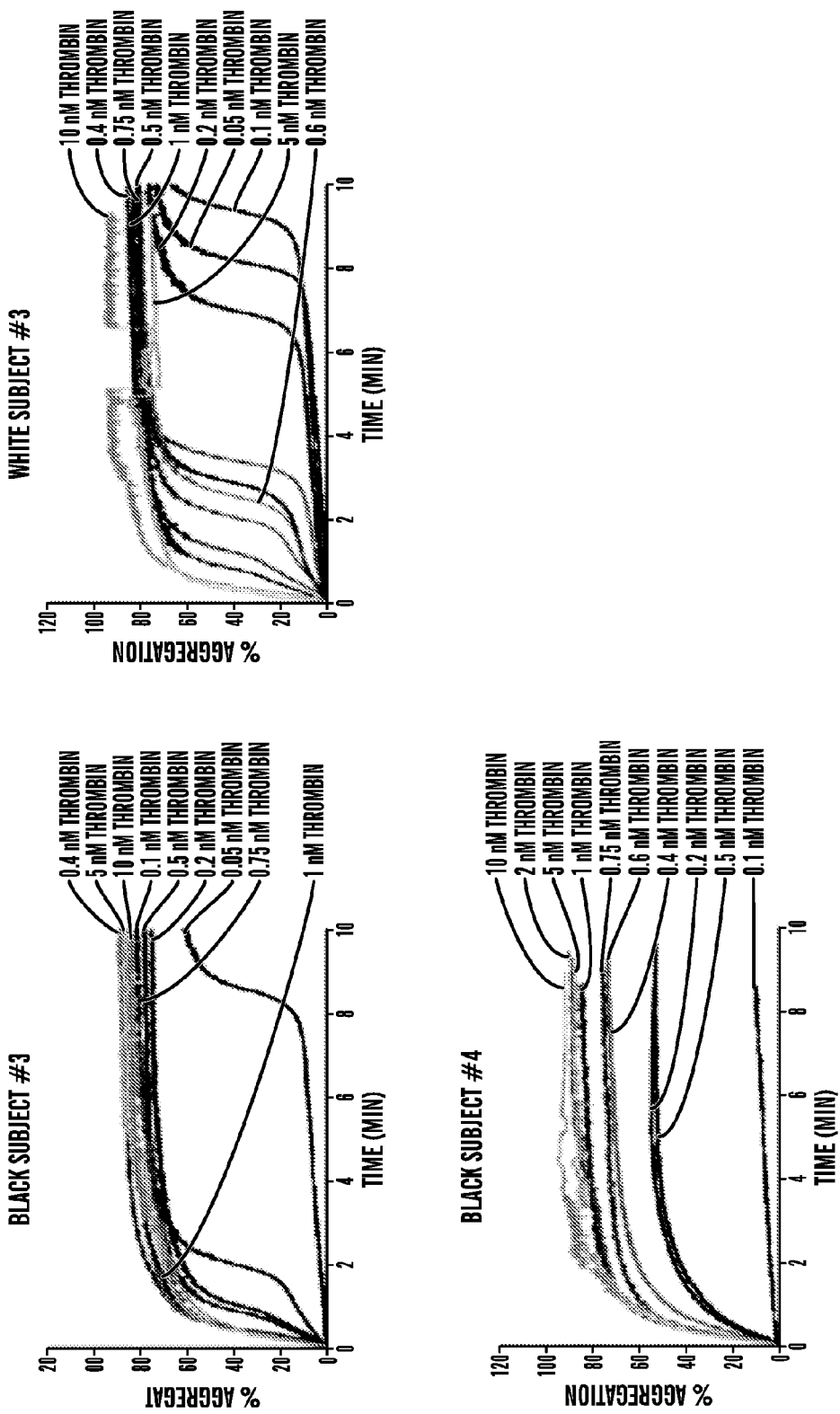
Figure 7B:
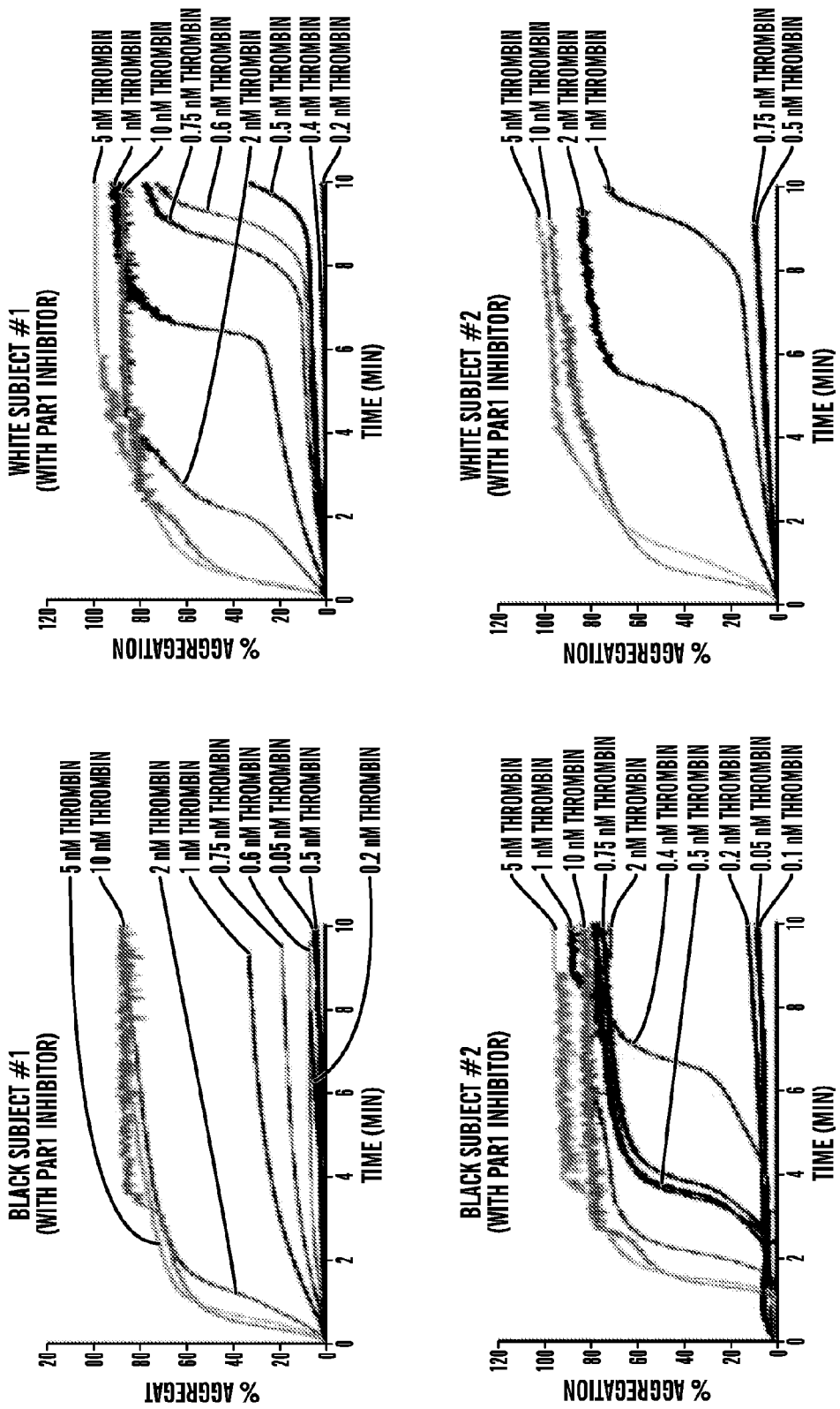
Figure 7B:
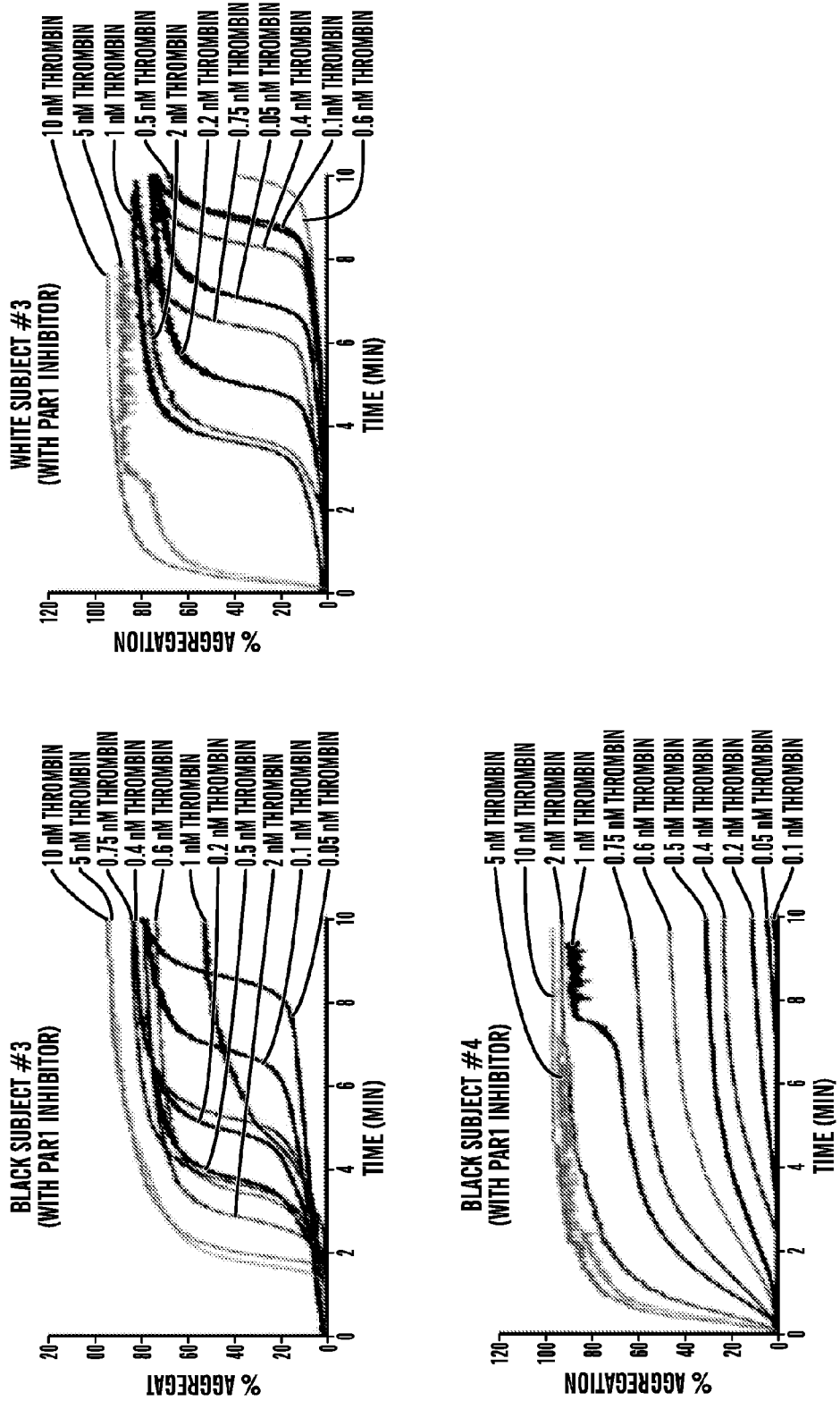
Figure 7C:
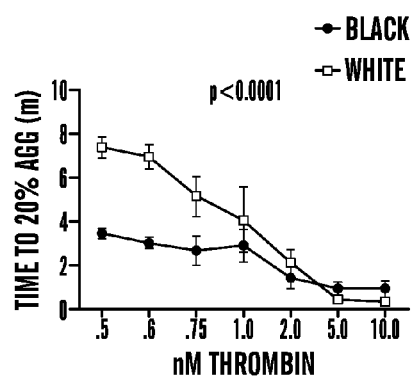
Figure 7D:
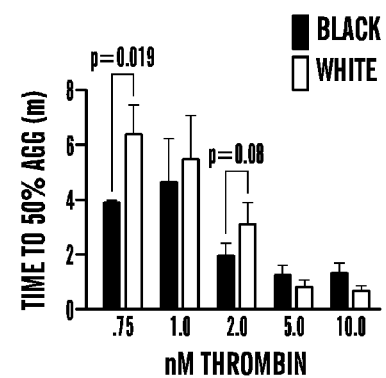
Figure 7E:
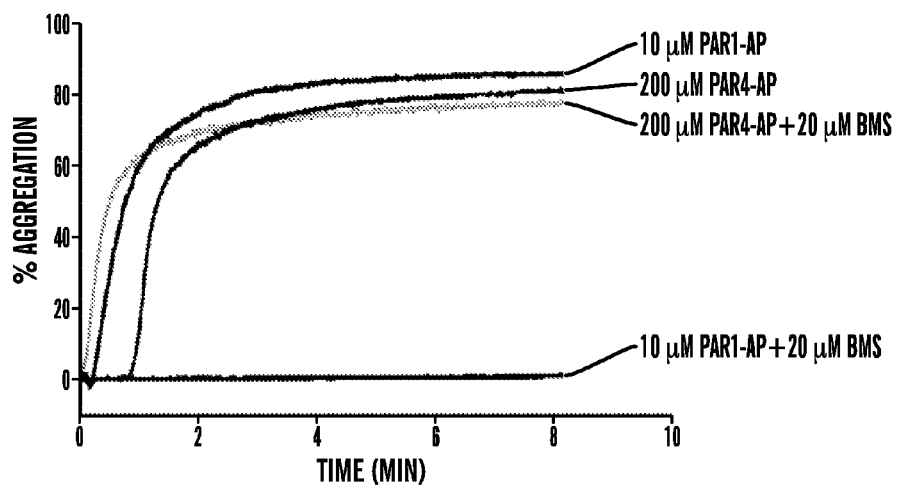

To address the possibility that PAR4-AP did not reflect the true thrombin response, a detailed dose-response study (4 blacks and 3 whites) was performed for racial differences in the platelet aggregation response to thrombin, the physiologic agonist of PAR4 and PAR1 (FIG. 7A). When thrombin signaling was restricted to PAR4 by inhibiting PAR1 with BMS-200261 (Quinton et al., J. Biol. Chem. 2004, 279, 18434-18439), platelets from black subjects aggregated faster than platelets from white subjects at low concentrations of thrombin (FIGS. 7B-7D). FIG. 7E demonstrates the absence of PAR1-AP-induced aggregation in the presence of BMS-200261. No racial difference in maximal percent aggregation to high concentrations of thrombin through PAR4 was observed (FIGS. 7A-7D). Guided by results of the detailed thrombin dose-response study, a replicate study with an additional 5 black and 5 white subjects was performed. At low doses of thrombin (0.6 nM-1 nM) platelets from black subjects again aggregated faster than white subjects in the absence of PAR1 signaling ($p=3.56\times10^{-5}$) (FIG. 1B).

Principal components analysis applied to the PRAX1 data set revealed 2 distinct and non-overlapping groups that accounted for the largest variance in the genotype data. Superimposition of the self-identified race information onto the PCA results (FIG. 1C) indicated a 100% concordance. Taken together, these data indicate a racial difference specific to PAR4 signaling in human platelets.

Platelet Protein Coding Transcripts Differentially Expressed (DE) by PAR4 Reactivity and Race.

Figure 8B:
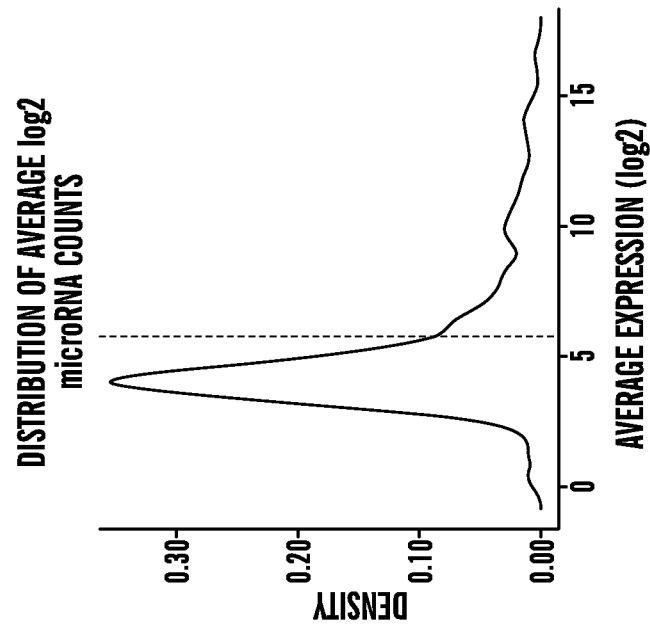
FIGS. 8A-8B present probability density plots of all mRNAs and miRNAs. Probability density plots of all mRNAs (FIG. 8A) and all miRNAs (FIG. 8B) plotted by the average log 2 expression. The vertical dash line indicates the arbitrary threshold for the most abundantly expressed RNAs based on the shape of the curve. The term "most commonly expressed" RNAs is defined as those mRNAs expressed above 1.5 in at least 75% (115/154) of subjects and miRNAs expressed above 5.8 in at least 65% (100/154) of subjects.
Figure 8A:
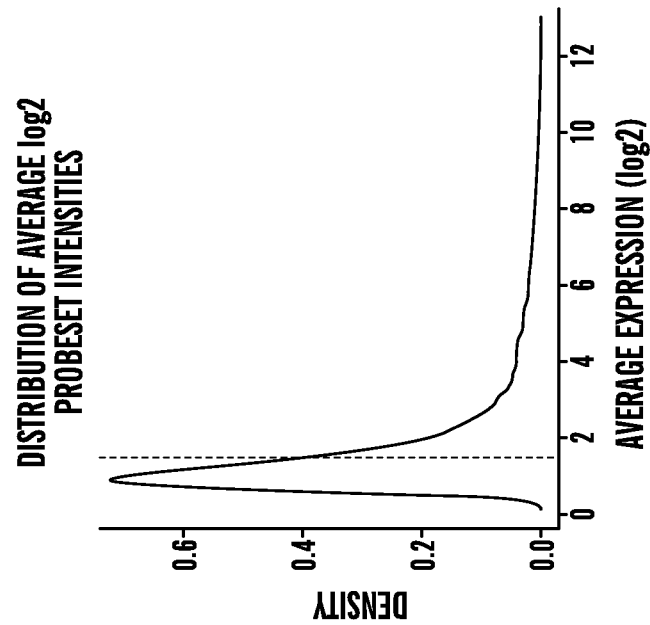
Figure 9A:
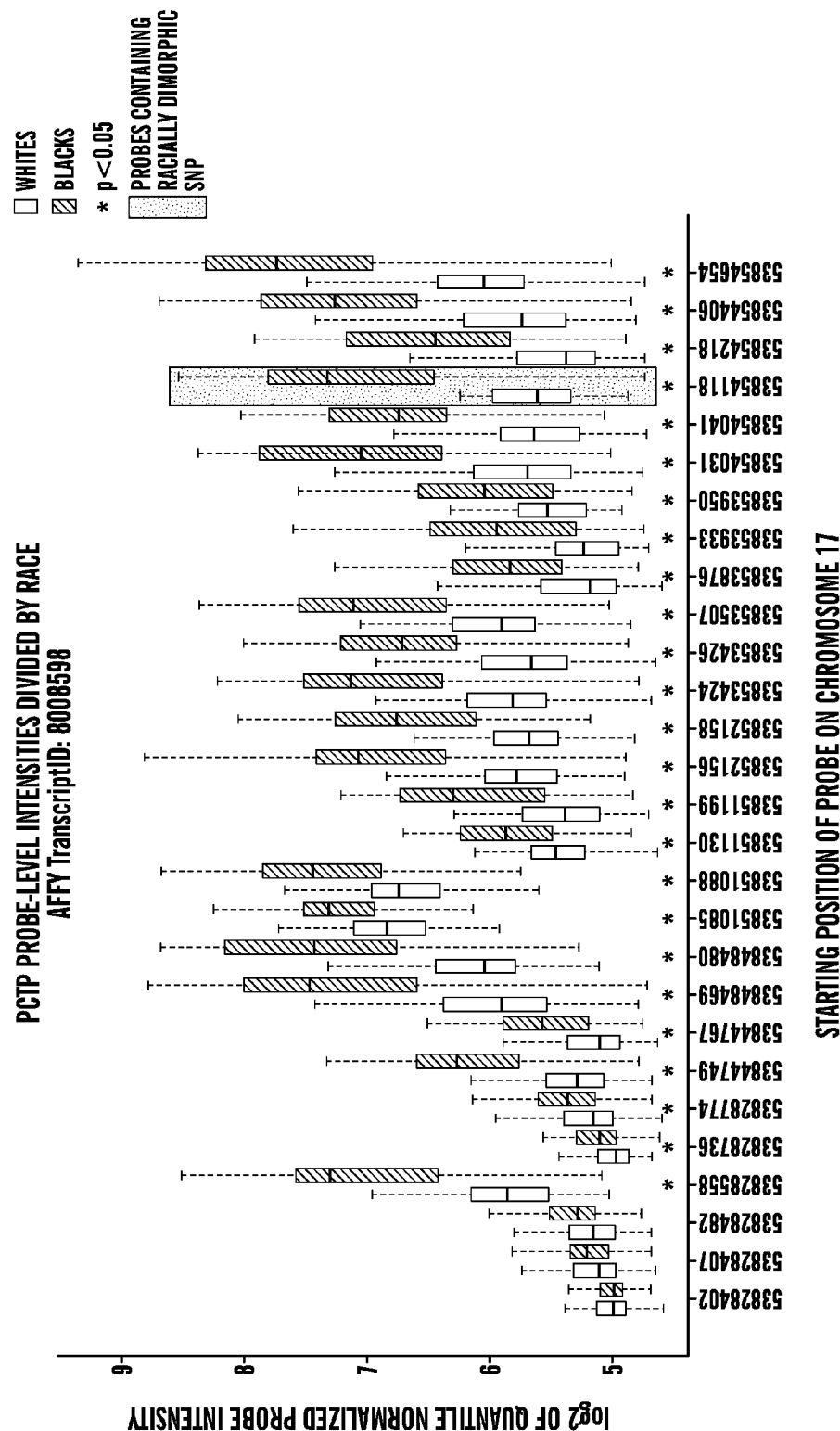
FIGS. 9A-9B show Affy Gene ST 1.0 array oligonucleotide probe level data by race.
Figure 9B:
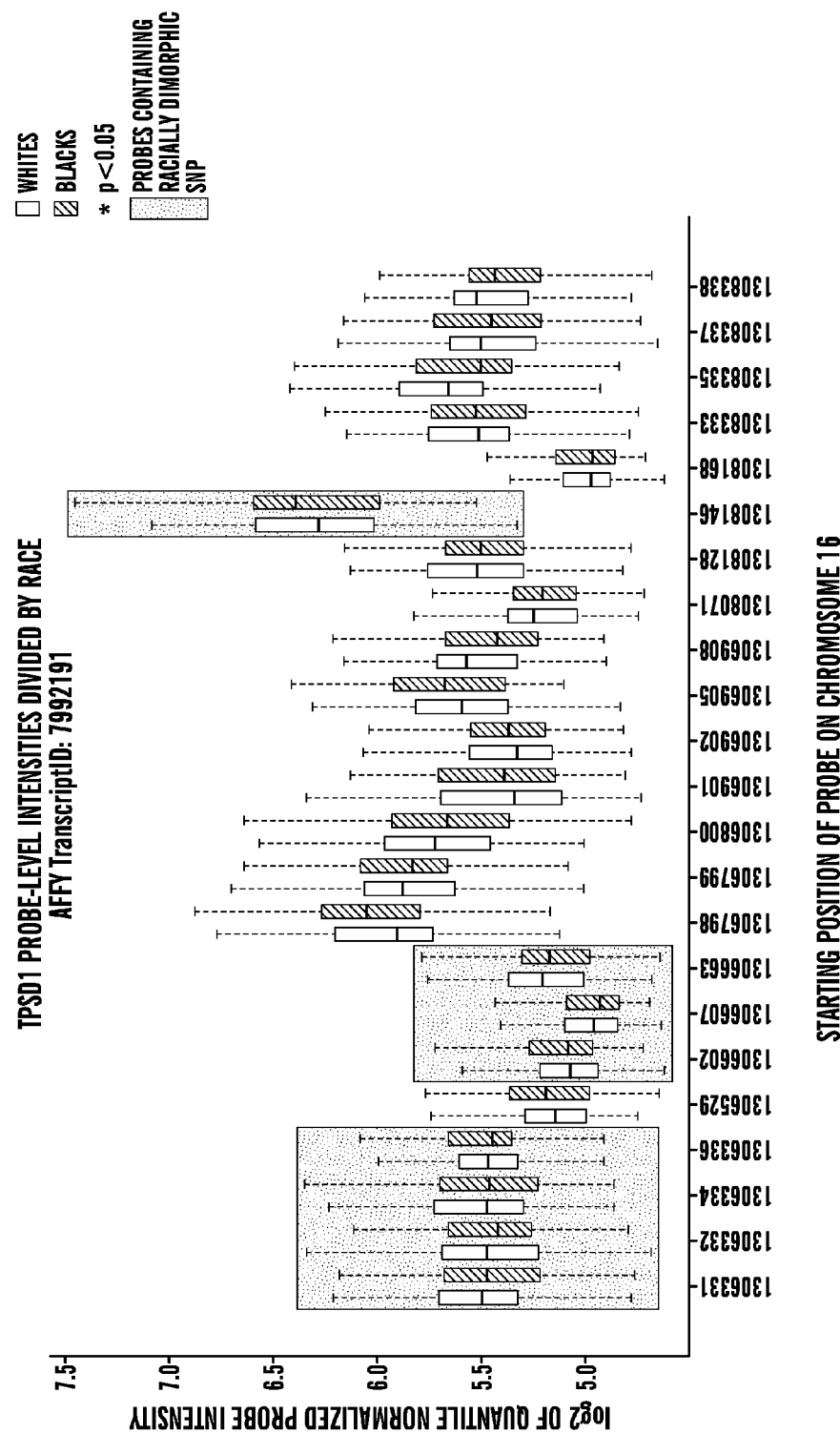

Highly purified, leukocyte-depleted platelets (LDPs) were prepared from the PRAX1 study subjects by density centrifugation of citrated whole blood followed by immunodepletion of CD45+ leukocytes (Nagalla et al., Blood 2011, 117, 5189-5197). LDP mRNA was profiled by the Human Gene 1.0 ST Array (Affymetrix). Based on a probability density plot, a threshold for expression was selected (FIG. 8A). Among expressed transcripts reflecting more than 9000 commonly expressed annotated human genes, 113 were identified as DE by PAR4 reactivity, of which 93 were positively correlated (Table 3a) and 20 were negatively correlated (Table 3b), using a False Discovery Rate (FDR) q-value cutoff of 0.25 (Benjamini et al., J. R. Statist. Soc. 1995, 57, 289-300). It was found that 97 of 113 (86%) of the PAR4 correlated transcripts were also DE between races, a much higher fraction than would be expected from the background rate of 30% DE by race among all platelet expressed transcripts (OR=14.08, 95% CI.8.23-25.65, $p=2.58\times10^{-34}$), or the 36% DE by race found by Zhang et al (Am. J. Hum. Genet. 2008, 82, 631-640). Analyses were performed to ensure that racially divergent SNVs occurring in the probe sequences on the Affymetrix Human Gene 1.0 ST Array did not drive the observed probe-set level (transcript/gene) correlations (FIGS. 9A and 9B).

Using a simple linear regression at FDR q<0.25; this FDR cutoff corresponds to a maximum p-value of 0.00345. Table 3a shows 119 mRNAs in the same order as in the heatmap in FIG. 3A. Symbols were determined integrating Affymetrix information tables with Bioconductor annotations. The p-value for race describes the T-test of black vs white. The coefficient and p-value for PAR4 describe the correlation between the PAR4 agonist score and mRNA expression across 154 individuals. The q-values represent the p-value accounting for multiple testing using Benjamini & Hochberg False Discovery Rate (1995).

TABLE 3a mRNAs positively correlated with PAR4-mediated platelet reactivity.

| | Affymetrix Transcript Cluster ID | Symbol | Mean | Race p-value | Race q-value | PAR4 Coefficient | PAR4 p-value | PAR4 q-value | Significant by race |
|---|---|---|---|---|---|---|---|---|---|
| 1 | 8008598 | PCTP | 4.87 | 1.00E−23 | 1.15E−19 | 0.31 | 3.49E−08 | 4.00E−04 | yes |
| 2 | 8172035 | DYNLT3 | 6.62 | 2.19E−13 | 5.02E−10 | 0.35 | 1.13E−07 | 6.45E−04 | yes |
| 3 | 8116859 | TMEM14C | 2.82 | 1.01E−10 | 5.24E−08 | 0.57 | 3.78E−06 | 1.44E−02 | yes |
| 4 | 8104693 | PDZD2 | 1.60 | 2.40E−04 | 6.26E−08 | 1.06 | 1.13E−05 | 2.47E−02 | yes |
| 5 | 8051464 | HEATR5B | 2.77 | 1.16E−03 | 1.83E−02 | 1.01 | 1.41E−05 | 2.47E−02 | yes |
| 6 | 8124307 | CMAHP | 4.08 | 3.88E−09 | 1.27E−06 | 0.63 | 1.65E−05 | 2.47E−02 | yes |
| 7 | 8084173 | ATP11B | 5.08 | 4.86E−12 | 5.07E−09 | 0.45 | 1.72E−05 | 2.47E−02 | yes |
| 8 | 8045860 | PKP4 | 3.14 | 3.33E−08 | 6.94E−06 | 0.58 | 2.75E−05 | 3.50E−02 | yes |
| 9 | 8019954 | FLJ35776 | 3.59 | 1.28E−06 | 1.35E−04 | 0.59 | 4.05E−05 | 4.33E−02 | yes |
| 10 | 7978970 | CDKL1 | 2.33 | 2.05E−02 | 1.19E−01 | 1.09 | 4.87E−05 | 4.33E−02 | yes |
| 11 | 7875863 | C14orf118 | 4.21 | 3.35E−03 | 3.75E−02 | 1.03 | 4.91E−05 | 4.33E−02 | yes |
| 12 | 8046238 | MYO38 | 1.38 | 1.76E−17 | 1.01E−13 | 0.70 | 5.90E−05 | 4.84E−02 | yes |
| 13 | 8068593 | ETS2 | 3.11 | 1.00E−10 | 5.24E−08 | 0.51 | 6.46E−35 | 4.94E−02 | yes |
| 14 | 8066402 | C20orf111 | 2.18 | 1.32E−04 | 4.12E−03 | 0.87 | 6.94E−05 | 4.97E−02 | yes |
| 15 | 8053551 | REEP1 | 2.64 | 2.30E−11 | 1.76E−08 | 0.38 | 8.70E−05 | 5.87E−02 | yes |
| 16 | 7924526 | TP53BP2 | 2.64 | 2.12E−06 | 1.95E−04 | 0.64 | 9.52E−05 | 5.07E−02 | yes |
| 17 | 7948656 | FTH1 | 9.44 | 5.74E−06 | 4.04E−04 | 1.65 | 1.14E−04 | 5.86E−02 | yes |
| 18 | 8065710 | E2F1 | 3.53 | 1.98E−06 | 1.86E−04 | 0.48 | 1.22E−04 | 6.99E−02 | yes |
| 19 | 7937378 | PTDSS2 | 1.89 | 4.72E−06 | 9.67E−03 | 1.24 | 1.43E−04 | 7.79E−02 | yes |
| 20 | 7978538 | ARHGAP5-AS1 | 2.57 | 5.15E−06 | 3.64E−04 | 0.56 | 1.71E−04 | 8.66E−02 | yes |
| 21 | 8139057 | ELMO1 | 5.63 | 2.13E−06 | 1.95E−04 | 0.54 | 1.74E−04 | 8.66E−02 | yes |
| 22 | 8067011 | ADNP | 3.85 | 1.04E−03 | 1.69E−02 | 0.76 | 2.53E−04 | 1.09E−01 | yes |
| 23 | 8001876 | NAE1 | 4.05 | 1.62E−01 | 4.12E−01 | 0.52 | 2.61E−04 | 1.09E−01 | no |
| 24 | 8154563 | ACER2 | 4.36 | 3.28E−05 | 1.48E−03 | 0.60 | 2.63E−04 | 1.09E−01 | yes |
| 25 | 8026193 | C19orf53 | 4.59 | 3.37E−03 | 3.76E−02 | 0.85 | 2.77E−04 | 1.09E−01 | yes |
| 26 | 7905519 | LCE1E | 3.01 | 1.09E−02 | 7.89E−02 | 0.88 | 2.77E−04 | 1.09E−01 | yes |
| 27 | 8110589 | CNOT6 | 2.86 | 1.92E−02 | 1.14E−01 | 0.87 | 2.94E−04 | 1.12E−01 | yes |
| 28 | 7900609 | ERMAP | 1.74 | 9.12E−03 | 6.95E−02 | 1.22 | 3.38E−04 | 1.13E−01 | yes |
| 29 | 8171481 | AP1S2 | 4.63 | 1.27E−02 | 8.71E−02 | 0.82 | 3.59E−04 | 1.13E−01 | yes |
| 30 | 8117608 | HIST1H2AL | 3.22 | 1.41E−07 | 2.34E−05 | 0.67 | 3.77E−04 | 1.13E−01 | yes |
| 31 | 7979691 | LOC100128233 | 3.17 | 3.28E−09 | 1.14E−06 | 0.18 | 3.81E−04 | 1.13E−01 | yes |
| 32 | 8123644 | TUBB2A | 3.30 | 7.64E−11 | 4.66E−08 | 0.17 | 3.84E−04 | 1.13E−01 | yes |
| 33 | 7975747 | DLST | 4.29 | 2.93E−04 | 7.05E−08 | 0.55 | 3.88E−04 | 1.13E−01 | yes |
| 34 | 8123678 | PXDC1 | 2.72 | 2.76E−05 | 1.29E−03 | 0.39 | 3.92E−04 | 1.13E−01 | yes |
| 35 | 8117580 | HIST1H2AI | 4.95 | 2.78E−06 | 2.32E−04 | 0.44 | 3.95E−04 | 1.13E−01 | yes |
| 36 | 8088803 | EIF4E3 | 4.85 | 7.72E−11 | 4.66E−08 | 0.27 | 4.08E−04 | 1.14E−01 | yes |
| 37 | 8095360 | GCOM2 | 1.86 | 6.45E−05 | 2.47E−03 | 0.76 | 4.31E−04 | 1.18E−01 | yes |
| 38 | 8166500 | ZFX | 1.72 | 8.64E−02 | 2.88E−01 | 0.79 | 4.77E−04 | 1.27E−01 | no |
| 39 | 8168843 | RPL35A | 4.38 | 3.22E−12 | 3.70E−09 | 0.31 | 5.19E−04 | 1.35E−01 | yes |
| 40 | 7920100 | THEM5 | 2.70 | 2.68E−08 | 5.79E−06 | 0.73 | 5.64E−04 | 1.44E−01 | yes |
| 41 | 8006239 | NF1 | 1.78 | 8.15E−07 | 9.64E−05 | 0.76 | 5.97E−04 | 1.45E−01 | yes |
| 42 | 8146687 | ADHFE1 | 1.51 | 1.34E−06 | 1.38E−04 | 0.96 | 6.28E−04 | 1.45E−01 | yes |
| 43 | 7897561 | KIF1B | 3.01 | 3.67E−06 | 2.84E−04 | 0.47 | 6.32E−04 | 1.45E−01 | yes |
| 44 | 7958346 | C12orf23 | 3.06 | 9.44E−03 | 7.11E−02 | 0.73 | 6.33E−04 | 1.45E−01 | yes |
| 45 | 8083282 | HPS3 | 1.53 | 1.36E−02 | 9.03E−02 | 0.88 | 6.72E−04 | 1.45E−01 | yes |
| 46 | 8002975 | CDYL2 | 2.20 | 6.90E−09 | 1.93E−06 | 0.48 | 6.75E−04 | 1.48E−01 | yes |
| 47 | 7983228 | MAP1A | 4.77 | 4.19E−04 | 8.89E−03 | 0.42 | 6.99E−04 | 1.48E−01 | yes |
| 48 | 7999478 | TXNDC11 | 2.11 | 4.26E−03 | 4.32E−02 | 1.28 | 7.09E−04 | 1.48E−01 | yes |
| 49 | 8056217 | MXRA7 | 1.64 | 2.22E−03 | 2.79E−02 | 0.52 | 7.28E−04 | 1.48E−01 | yes |
| 50 | 8000791 | YPEL3 | 5.57 | 9.14E−09 | 2.44E−06 | 0.66 | 7.62E−04 | 1.48E−01 | yes |
| 51 | 8164428 | TRUB2 | 2.94 | 8.32E−10 | 3.82E−10 | 0.57 | 7.65E−04 | 1.48E−01 | yes |
| 52 | 7961198 | KLRAP1 | 1.56 | 1.20E−07 | 2.08E−05 | 0.50 | 8.04E−04 | 1.48E−01 | yes |
| 53 | 8116651 | ENST00000408316 | 4.52 | 1.98E−12 | 2.52E−09 | 0.26 | 8.15E−04 | 1.48E−01 | yes |
| 54 | 8106660 | RASGRF2 | 3.09 | 6.34E−09 | 1.82E−06 | 0.49 | 8.35E−04 | 1.50E−01 | yes |
| 55 | 7946807 | RPL36A | 5.65 | 1.65E−12 | 2.37E−09 | 0.29 | 8.52E−04 | 1.50E−01 | yes |
| 56 | 7955441 | METTL7A | 2.60 | 1.33E−08 | 3.18E−06 | 0.37 | 9.34E−04 | 1.60E−01 | yes |
| 57 | 8014825 | FBXL20 | 2.97 | 3.12E−04 | 7.31E−03 | 0.74 | 9.42E−04 | 1.60E−01 | yes |
| 58 | 7936968 | ADAM12 | 1.66 | 1.32E−05 | 7.87E−04 | 0.79 | 9.58E−04 | 1.60E−01 | yes |
| 59 | 8116653 | TUBB2A | 5.24 | 1.30E−12 | 2.14E−09 | 0.13 | 1.00E−03 | 1.60E−01 | yes |
| 60 | 8116649 | TUBB2A | 5.24 | 1.30E−12 | 2.14E−09 | 0.13 | 1.00E−03 | 1.60E−01 | yes |
| 61 | 7971620 | KPNA3 | 5.22 | 4.36E−01 | 6.85E−01 | 0.81 | 1.09E−03 | 1.64E−01 | no |
| 62 | 8000706 | CDIPT | 3.77 | 1.97E−03 | 2.60E−02 | 0.57 | 1.12E−03 | 1.64E−01 | yes |
| 63 | 8139712 | VOPP1 | 3.31 | 1.31E−03 | 1.98E−02 | 0.77 | 1.13E−03 | 1.64E−01 | yes |
| 64 | 7897172 | TPRG1L | 4.71 | 4.11E−07 | 5.42E−05 | 0.61 | 1.13E−03 | 1.64E−01 | yes |
| 65 | 7924499 | TLR5 | 2.84 | 4.60E−10 | 2.20E−07 | 0.65 | 1.22E−03 | 1.71E−01 | yes |
| 66 | 8066051 | NORG3 | 4.16 | 5.33E−03 | 4.96E−02 | 0.44 | 1.24E−03 | 1.71E−01 | yes |
| 67 | 8156199 | DAPK1 | 2.03 | 1.19E−04 | 3.80E−03 | 0.73 | 1.24E−03 | 1.71E−01 | yes |
| 68 | 8088813 | PROK2 | 5.60 | 9.80E−15 | 3.75E−11 | 0.20 | 1.24E−03 | 1.71E−01 | yes |
| 69 | 8121578 | NT5DC1 | 2.28 | 2.29E−11 | 1.14E−08 | 0.59 | 1.28E−03 | 1.73E−01 | yes |
| 70 | 8138361 | RPL36A | 3.76 | 1.93E−11 | 1.60E−08 | 0.26 | 1.32E−03 | 1.75E−01 | Yes |
| 71 | 7994981 | ORAI3 | 3.52 | 2.76E−07 | 3.91E−05 | 0.78 | 1.36E−03 | 1.76E−01 | yes |
| 72 | 8113483 | TMEM232 | 1.69 | 1.53E−06 | 1.50E−04 | 0.46 | 1.38E−03 | 1.76E−01 | yes |
| 73 | 7925531 | AKT3 | 7.21 | 2.77E−04 | 6.78E−03 | 0.74 | 1.41E−03 | 1.77E−01 | yes |
| 74 | 8076465 | POLDIP3 | 2.68 | 1.83E−02 | 1.11E−01 | 0.78 | 1.46E−03 | 1.78E−01 | yes |

TABLE 3a-continued mRNAs positively correlated with PAR4-mediated platelet reactivity.

| | Affymetrix Transcript Cluster ID | Symbol | Mean | Race p-value | Race q-value | PAR4 Coefficient | PAR4 p-value | PAR4 q-value | Significant by race |
|---|---|---|---|---|---|---|---|---|---|
| 75 | 8169044 | TCEAL3 | 2.22 | 3.52E-02 | 1.67E-01 | 0.49 | 1.66E-03 | 1.98E-01 | yes |
| 76 | 7943760 | SIK2 | 2.30 | 5.36E-05 | 2.13E-03 | 0.87 | 1.70E-03 | 1.98E-01 | yes |
| 77 | 7905700 | UBAP2L | 3.22 | 2.75E-02 | 1.43E-01 | 0.90 | 1.72E-03 | 1.98E-01 | yes |
| 78 | 8141016 | TFPI2 | 2.25 | 1.30E-04 | 4.07E-03 | 0.52 | 1.72E-03 | 1.98E-01 | yes |
| 79 | 8124388 | HIST1H3B | 6.52 | 3.43E-09 | 1.16E-06 | 0.35 | 1.82E-03 | 2.05E-01 | yes |
| 80 | 8117382 | HIST1H2BD | 7.40 | 2.06E-05 | 1.07E-03 | 0.39 | 1.92E-03 | 2.09E-01 | yes |
| 81 | 8011713 | CXCL16 | 4.19 | 2.49E-06 | 2.12E-04 | 0.33 | 1.93E-03 | 2.09E-01 | yes |
| 82 | 8145977 | PLEKHA2 | 2.30 | 2.32E-06 | 2.03E-04 | 0.45 | 1.97E-03 | 2.09E-01 | yes |
| 83 | 8119067 | KCTD20 | 6.73 | 4.20E-02 | 1.87E-01 | 0.70 | 2.07E-03 | 2.10E-01 | yes |
| 84 | 7974229 | KLHDC2 | 2.89 | 3.98E-03 | 4.17E-02 | 0.58 | 2.08E-03 | 2.10E-01 | yes |
| 85 | 7977584 | TMEM55B | 1.95 | 2.64E-01 | 5.31E-01 | 0.85 | 2.08E-03 | 2.10E-01 | no |
| 86 | 8063211 | NCOA3 | 5.83 | 2.18E-04 | 5.88E-03 | 0.55 | 2.09E-03 | 2.10E-01 | yes |
| 87 | 8137464 | PSPH | 1.47 | 6.01E-07 | 7.26E-05 | 0.30 | 2.13E-03 | 2.12E-01 | yes |
| 88 | 8052149 | PSME4 | 3.71 | 1.78E-02 | 1.08E-01 | 0.59 | 2.20E-03 | 2.13E-01 | yes |
| 89 | 7918657 | PTPN22 | 2.96 | 1.55E-01 | 4.01E-01 | 0.77 | 2.21E-03 | 2.13E-01 | no |
| 90 | 8082350 | MCM2 | 1.72 | 3.67E-03 | 3.97E-02 | 0.97 | 2.25E-03 | 2.15E-01 | yes |
| 91 | 7970546 | EFHA1 | 2.19 | 9.48E-02 | 3.03E-01 | 0.60 | 2.32E-03 | 2.18E-01 | no |
| 92 | 7924773 | CDC42BPA | 3.19 | 1.16E-01 | 3.39E-01 | 0.65 | 2.40E-03 | 2.20E-01 | no |
| 93 | 8130474 | SERAC1 | 2.28 | 3.24E-01 | 5.90E-01 | 0.70 | 2.41E-03 | 2.20E-01 | no |
| 94 | 8156263 | SPIN1 | 2.93 | 3.96E-03 | 4.16E-02 | 0.62 | 2.45E-03 | 2.20E-01 | yes |
| 95 | 7919305 | PRKAB2 | 4.23 | 8.49E-03 | 6.65E-02 | 0.36 | 2.45E-03 | 2.20E-01 | yes |
| 96 | 7997197 | DHX38 | 1.46 | 2.03E-03 | 2.65E-02 | 0.75 | 2.47E-03 | 2.20E-01 | yes |
| 97 | 8117535 | HIST1H2AG | 8.21 | 1.11E-05 | 6.85E-04 | 0.51 | 2.48E-03 | 2.20E-01 | yes |
| 98 | 8139917 | WBSCR17 | 1.51 | 3.49E-02 | 1.66E-01 | 0.83 | 2.52E-03 | 2.20E-01 | yes |
| 99 | 8011747 | SLC25A11 | 1.77 | 1.37E-02 | 9.10E-02 | 0.70 | 2.55E-03 | 2.20E-01 | yes |
| 100 | 8170326 | FMR1 | 2.90 | 2.67E-02 | 1.41E-01 | 0.74 | 2.56E-03 | 2.20E-01 | yes |
| 101 | 7939676 | ATG13 | 2.56 | 5.14E-02 | 2.11E-01 | 0.62 | 2.56E-03 | 2.20E-01 | yes |
| 102 | 8155234 | ZCCHC7 | 2.90 | 1.84E-03 | 2.46E-02 | 0.80 | 2.57E-03 | 2.20E-01 | yes |
| 103 | 7920912 | UBQLN4 | 2.25 | 8.27E-03 | 6.53E-02 | 1.14 | 2.74E-03 | 2.28E-01 | yes |
| 104 | 8175393 | ARHGEF6 | 2.68 | 1.65E-01 | 4.14E-01 | 0.55 | 2.75E-03 | 2.28E-01 | no |
| 105 | 8015946 | C17orf65 | 3.01 | 3.28E-06 | 2.59E-04 | 0.54 | 2.82E-03 | 2.33E-01 | yes |
| 106 | 8135532 | C7orf53 | 1.69 | 1.55E-05 | 8.76E-04 | 0.61 | 2.85E-03 | 2.33E-01 | yes |
| 107 | 8087731 | C3orf18 | 2.15 | 1.22E-01 | 3.50E-01 | 0.97 | 2.91E-03 | 2.36E-01 | no |
| 108 | 8008547 | TOM1L1 | 4.76 | 5.89E-02 | 2.27E-01 | 0.65 | 2.97E-03 | 2.40E-01 | yes |
| 109 | 8043413 | RPIA | 2.11 | 1.95E-11 | 1.60E-08 | 0.47 | 3.02E-03 | 2.41E-01 | yes |
| 110 | 8176163 | GAB3 | 2.65 | 6.67E-02 | 2.48E-01 | 0.72 | 3.08E-03 | 2.41E-01 | yes |
| 111 | 8168357 | RPS26 | 5.03 | 6.01E-04 | 1.15E-02 | 0.37 | 3.10E-03 | 2.41E-01 | yes |
| 112 | 7974257 | ATP5S | 2.44 | 1.01E-01 | 3.13E-01 | 0.81 | 3.10E-03 | 2.41E-01 | no |
| 113 | 8108472 | PURA | 4.63 | 4.01E-03 | 4.18E-02 | 0.70 | 3.15E-03 | 2.41E-01 | yes |
| 114 | 8116867 | TMEM14B | 3.28 | 7.64E-04 | 1.35E-02 | 0.41 | 3.16E-03 | 2.41E-01 | yes |
| 115 | 8054377 | FHL2 | 3.02 | 1.47E-03 | 2.10E-02 | 0.46 | 3.21E-03 | 2.41E-01 | yes |
| 116 | 7986675 | NIPA1 | 3.22 | 9.62E-07 | 1.08E-04 | 0.32 | 3.22E-03 | 2.41E-01 | yes |
| 117 | 8171182 | PRKX | 1.83 | 5.22E-03 | 4.91E-02 | 0.77 | 3.34E-03 | 2.46E-01 | yes |
| 118 | 8019842 | TYMS | 1.37 | 2.16E-03 | 2.74E-02 | 0.75 | 3.44E-03 | 2.49E-01 | yes |
| 119 | 8088247 | ARHGEF3 | 3.95 | 6.69E-06 | 4.54E-04 | 0.48 | 3.45E-03 | 2.49E-01 | yes |

TABLE 3b

Set of mRNAs negatively correlated with PAR4-mediated platelet reactivity

| | Affymetrix Transcript Cluster ID | Symbol | Mean | Race p-value | Race q-value | PAR4 Coefficient | PAR4 p-value | PAR q-value | Significant by race |
|---|---|---|---|---|---|---|---|---|---|
| 1 | 8147132 | CA2 | 10.26 | 1.77E-10 | 8.80E-08 | -0.60 | 6.77E-06 | 1.94E-02 | yes |
| 2 | 8037222 | CEACAMB | 1.35 | 3.02E-01 | 5.68E-01 | -0.79 | 4.69E-05 | 4.33E-02 | no |
| 3 | 8042503 | MXD1 | 6.19 | 3.02E-06 | 2.46E-04 | -0.48 | 2.20E-04 | 1.05E-01 | yes |
| 4 | 8135319 | NA | 1.89 | 2.39E-01 | 5.05E-01 | -1.13 | 3.30E-04 | 1.13E-01 | no |
| 5 | 7958202 | CH5T11 | 3.08 | 7.40E-01 | 8.79E-01 | -0.54 | 3.41E-04 | 1.13E-01 | no |
| 6 | 8000184 | IGSF6 | 2.07 | 4.87E-01 | 7.25E-01 | -0.42 | 6.17E-04 | 1.45E-01 | no |
| 7 | 8136662 | MGAM | 1.07 | 2.12E-01 | 4.75E-01 | -0.47 | 6.88E-04 | 1.48E-01 | no |
| 8 | 8149137 | DEFA3 | 4.56 | 3.23E-02 | 1.59E-01 | -0.13 | 7.92E-04 | 1.48E-01 | yes |
| 9 | 8149126 | DEFA3 | 4.56 | 3.23E-02 | 1.59E-01 | -0.13 | 7.92E-04 | 1.48E-01 | yes |
| 10 | 8149116 | DEFA3 | 4.56 | 3.23E-02 | 1.59E-01 | -0.13 | 7.92E-04 | 1.48E-01 | yes |
| 11 | 8097468 | — | 1.37 | 2.65E-02 | 1.40E-01 | -0.82 | 9.75E-04 | 1.60E-01 | yes |
| 12 | 7922219 | SELL | 2.91 | 3.08E-01 | 5.74E-01 | -0.25 | 1.00E-03 | 1.60E-01 | no |
| 13 | 7912252 | RN5S40 | 1.83 | 1.35E-11 | 1.29E-08 | -0.65 | 1.02E-03 | 1.60E-01 | yes |
| 14 | 7967210 | LOC338799 | 1.80 | 1.77E-07 | 2.78E-05 | -0.52 | 1.06E-03 | 1.64E-01 | yes |
| 15 | 8127072 | GSTA1 | 3.05 | 1.87E-13 | 5.02E-10 | -0.19 | 1.10E-03 | 1.64E-01 | yes |
| 16 | 7957570 | PLXNC1 | 1.44 | 9.65E-02 | 3.06E-01 | -0.53 | 1.25E-03 | 1.71E-01 | no |

TABLE 3b-continued

Set of mRNAs negatively correlated with PAR4-mediated platelet reactivity

| | Affymetrix Transcript Cluster ID | Symbol | Mean | Race p-value | Race q-value | PAR4 Coefficient | PAR4 p-value | PAR q-value | Significant by race |
|---|---|---|---|---|---|---|---|---|---|
| 17 | 7927215 | ALOX5 | 1.86 | 7.97E−01 | 9.10E−01 | −0.42 | 1.32E−03 | 1.75E−01 | no |
| 18 | 7917532 | GBP2 | 1.11 | 4.45E−01 | 6.91E−01 | −0.51 | 1.37E−03 | 1.76E−01 | no |
| 19 | 8018305 | HN1 | 1.74 | 6.71E−01 | 8.41E−01 | −0.90 | 1.45E−03 | 1.78E−01 | no |
| 20 | 8097903 | TLR2 | 1.43 | 2.32E−01 | 4.98E−01 | −0.52 | 1.45E−03 | 1.78E−01 | no |
| 21 | 7961693 | LDH8 | 6.18 | 5.15E−04 | 1.03E−02 | −0.40 | 1.58E−03 | 1.91E−01 | yes |
| 22 | 7992811 | MMP25 | 1.91 | 1.46E−01 | 3.87E−01 | −0.74 | 1.73E−03 | 1.98E−01 | no |
| 23 | 8103975 | 5LED1 | 1.55 | 4.07E−01 | 6.50E−01 | −0.52 | 1.83E−03 | 2.05E−01 | no |
| 24 | 8171203 | — | 1.91 | 1.12E−03 | 1.78E−02 | −0.57 | 1.19E−03 | 2.09E−01 | yes |
| 25 | 8128394 | PNI5R | 1.77 | 2.76E−01 | 5.43E−01 | −0.68 | 1.95E−03 | 2.09E−01 | no |
| 26 | 7973371 | C14orf119 | 4.38 | 1.16E−08 | 2.97E−06 | −0.45 | 1.97E−03 | 2.09E−01 | yes |
| 27 | 7923547 | CHI3L1 | 1.29 | 1.31E−01 | 3.65E−01 | −0.55 | 2.02E−03 | 2.10E−01 | no |
| 28 | 7961390 | HEBP1 | 3.83 | 1.76E−05 | 9.64E−04 | −0.28 | 2.05E−03 | 2.10E−01 | yes |
| 29 | 8043478 | IGKV1D-8 | 1.43 | 7.43E−03 | 6.09E−02 | −0.61 | 2.18E−03 | 2.13E−01 | yes |
| 30 | 8070912 | SLC19A1 | 1.83 | 2.04E−01 | 4.67E−01 | −1.04 | 2.19E−03 | 2.13E−01 | no |
| 31 | 8091269 | TNFSPF10 | 1.28 | 1.90E−01 | 4.49E−01 | −0.29 | 2.31E−03 | 2.18E−01 | no |
| 32 | 8123181 | IGF2R | 1.63 | 3.91E−01 | 6.48E−01 | −0.46 | 2.50E−03 | 2.20E−01 | no |
| 33 | 7934906 | ACTA2 | 1.97 | 3.86E−02 | 1.78E−01 | −0.69 | 2.69E−03 | 2.28E−01 | yes |
| 34 | 8068697 | MX2 | 1.45 | 3.77E−01 | 6.38E−01 | −0.38 | 2.71E−03 | 2.28E−01 | no |
| 35 | 8163775 | MEGF9 | 2.45 | 2.77E−01 | 5.45E−01 | −0.40 | 3.01E−03 | 2.41E−01 | no |
| 36 | 8031213 | LILRA1 | 1.45 | 8.07E−01 | 9.15E−01 | −0.58 | 3.12E−03 | 2.41E−01 | no |
| 37 | 7983910 | AQP9 | 1.80 | 5.30E−01 | 7.56E−01 | −0.21 | 3.20E−03 | 2.41E−01 | no |
| 38 | 8126394 | MRP510 | 3.37 | 2.88E−07 | 4.02E−05 | −0.34 | 3.24E−03 | 2.41E−01 | yes |
| 39 | 8034199 | TSPAN16 | 1.76 | 6.89E−02 | 2.52E−01 | −0.53 | 3.35E−03 | 2.46E−01 | no |
| 40 | 7912194 | BCO29383 | 1.49 | 1.67E−01 | 4.17E−01 | −0.53 | 3.38E−03 | 2.47E−01 | no |
| 41 | 7976542 | ERVH-4 | 3.01 | 1.69E−02 | 1.05E−01 | −0.38 | 3.47E−03 | 2.49E−01 | yes |

In Table 3b, symbols were determined integrating Affymetrix information tables with Bioconductor annotations. The set of 41 mRNAs negatively correlated with PAR4-mediated platelet reactivity using a simple linear regression at FDR q<0.25; this FDR cutoff corresponds to a maximum p-value of 0.00345. The p-value for race describes the T-test of black vs white. The coefficient and p-value describe the correlation between the PAR4 agonist score and mRNA expression across 154 individuals. The q-value represents the p-value adjusted for multiple testing using the Benjamini & Hochberg False Discovery Rate (1995).

Phosphatidylcholine Transfer Protein (PC-TP) and Human Platelet PAR4 Reactivity.

Figure 2A:
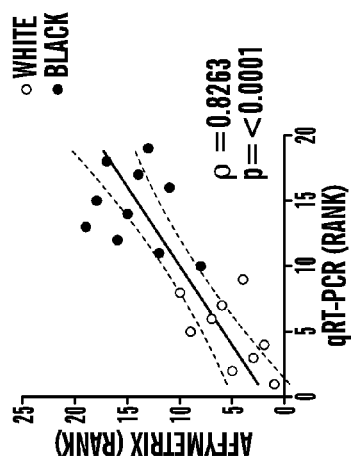
FIGS. 2A-2L show racial differences in human platelet PC-TP expression and function.
Figure 2B:
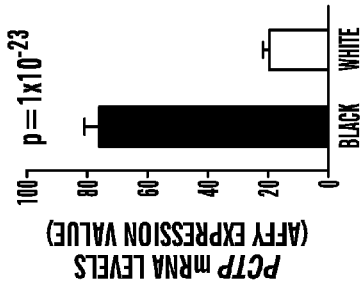
Figure 2C:
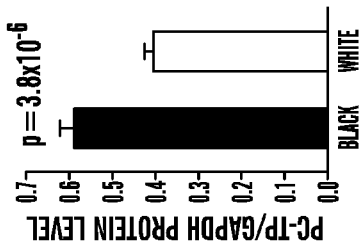
Figure 2D:
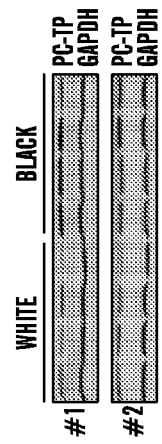

Since some of the 97 transcripts that were DE by race and PAR4 reactivity would be expected to be false positives, Gene Ontology (GO) analysis utilizing the Database for Annotation Visualization and Integrated Discovery (DAVID) (http://david.abcc.ncifcrf.gov/home.jsp) as a guide was performed for considering the most plausible true associations. Using default settings and all assayed mRNAs as the reference, mRNAs DE by PAR4 reactivity were found to be positively enriched in genes with phospholipid transporter activity (p=8.0×10$^{-3}$), serine/threonine kinases (p=4.4×10$^{-2}$) and proteins with pleckstrin homology (p=2.9×10$^{-3}$). All of these functional categories are known to be relevant to platelet physiology. The gene encoding PC-TP (also called StARD2) (Kang et al., Trends Endocrinol. Metab. 2010, 21, 449-456), PC-TP, showed the strongest correlation with race (p=10$^{-23}$; q=10$^{-20}$) and with PAR4 reactivity (p=3.4×10$^{-8}$; q=3.5×10$^{-4}$) (Table 3a). This was intriguing because lipid regulation is important for platelet function, and PC-TP is highly specific for binding phosphatidylcholine (PC) and catalyzes its transfer between membranes in vitro) (Kang et al., Trends Endocrinol. Metab. 2010, 21, 449-456). PC-TP mRNA was expressed approximately 4-fold higher in blacks than in whites (FIG. 2A), and this was confirmed by qRT-PCR (FIG. 2B) using samples selected to represent the extremes of the distribution as well as intermediate levels. The Spearman Rank correlation coefficient between the microarray and PCR data was 0.8263, and is within the normal validation range when comparing microarray and qRT-PCR data (Emanueli et al., PLoS One 2011, 6, e26905). This racial difference was also validated by western immunoblotting of platelet lysates from all 70 black and 84 white subjects (FIGS. 2C & 2D). Finally, a significant correlation between the normalized PC-TP protein levels and reactivity to PAR4-AP among the PRAX samples (r=0.249, p=0.002, Pearson correlation) was found.

Figure 2E:
Figure 2H:
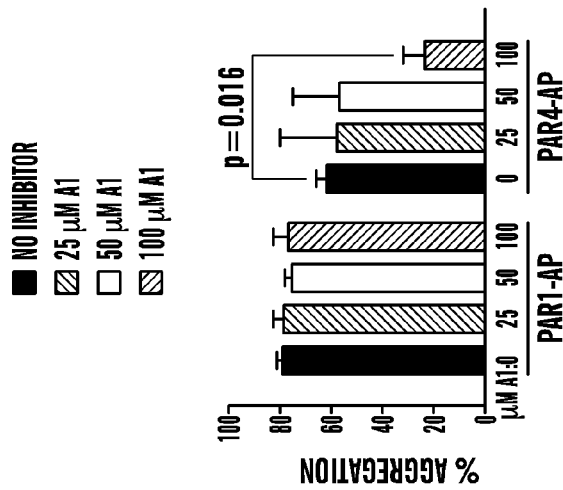
Figure 2G:
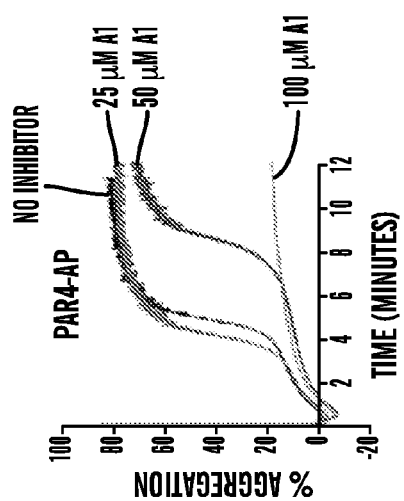
Figure 2F:
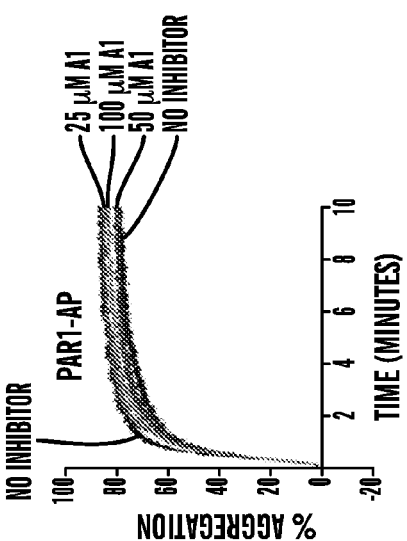
Figure 2J:
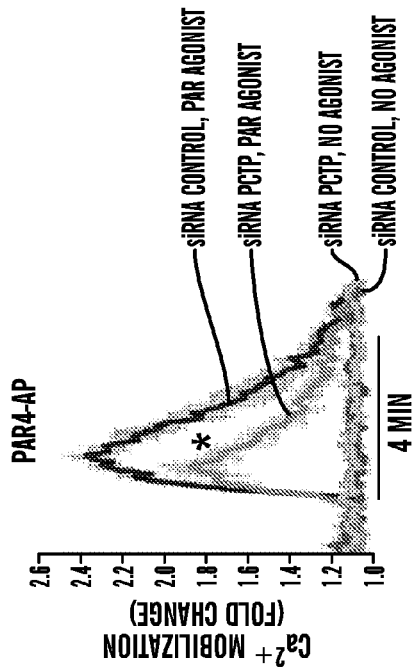
Figure 2I:
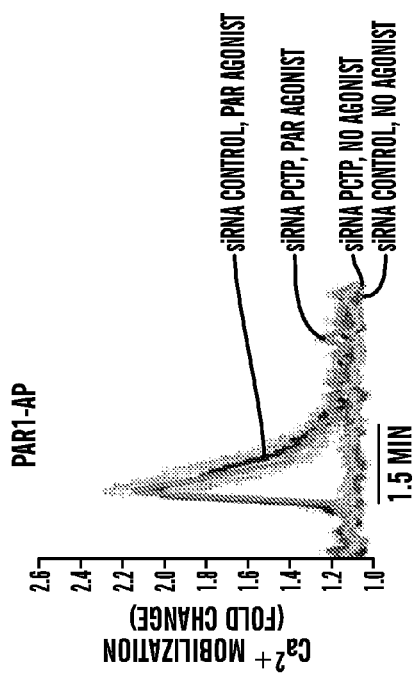
Figure 2L:
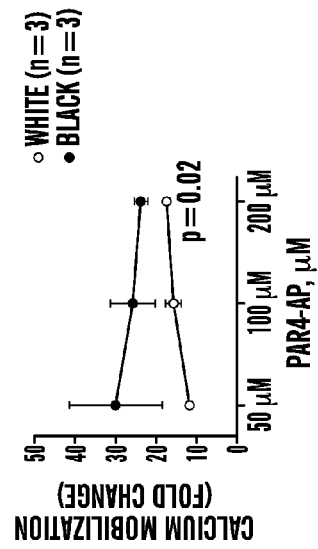
Figure 2K:
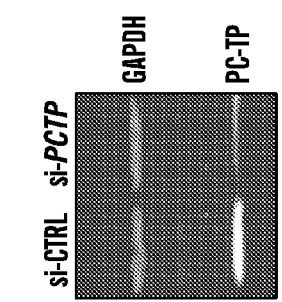

PC-TP has been knocked out in mice (van Helvoort et al., PNAS 1999, 96, 11501-11506), but it was found that wild type mouse platelets express little or no PC-TP protein (FIG. 2E), consistent with mouse platelet RNA data from Rowley et al (Blood 2011, 118, e101-111). Thus, other approaches were needed to test its function in human platelets. LDN-193,188, which has been identified as a small molecule inhibitor of the phoshatidycholine transfer activity of PC-TP (Wagel et al., Anal. Biochem. 2008, 383, 85-92), displaces phosphatidylcholine from the lipid binding pocket and increases the thermal stability of the protein (Shishova et al., Hepatology 2011, 54, 664-674). Incubation of human platelets with this specific PC-TP inhibitor prevented aggregation in response to PAR4-AP but not PAR1-AP (FIGS. 2F-2H). Calcium mobilization is a critical signaling event upon platelet activation through PAR4. The megakaryocytic cell line, Meg-01 mobilizes calcium in response to thrombin (Ozaki et al., Biochem Biophys Res Commun 1992, 183, 864-871), and similar to platelets, it was observed that the PAR4-mediated intracellular calcium concentration was more sustained than was the PAR1 response. Knockdown of PC-TP using siRNA blunted calcium release in response to PAR4-AP but not PAR1-AP (FIGS. 2I-2K). In addition, compared to platelets from white subjects, platelets from black subjects showed greater calcium mobilization in response to PAR4-AP (FIG. 2L). These data demonstrate a role for PC-TP in PAR4-mediated calcium flux in platelets and are consistent with PC-TP mediated racial differences in platelet aggregation.

The Gene for Phosphatidylcholine-Transfer Protein is Targeted by miR-376c.

MicroRNA (miRNA)-mediated mRNA degradation represents a potential mechanism for altering mRNA levels (Bartel, Cell 2004, 116, 281-297; Guo et al., Nature 2010, 466, 835-840). Prior efforts at platelet miRNA profiling have been rather small and lacked phenotype data relevant for PAR-mediated platelet activation (Nagalla et al., Blood 2011, 117, 5189-5197; Kondkar et al., J. Thromb. Haemost, 2010, 8, 369-378; Goodall et al., Blood 2010, 116, 4646-4656). The 154 PRAX1 platelet samples were profiled for miRNA levels and 178 miRNAs were identified as commonly expressed in human platelets using threshold criteria similar to the approach used for mRNA (FIGS. 8A and 8B). The common platelet miRNAs that were DE by race and were predicted to target mRNAs DE by race and PAR4 reactivity was considered. FIG. 3A concisely presents the patterns observed in the data: (i) PAR4 response is higher in blacks than whites (FIG. 3A, upper heatmap), (ii) corresponding elevation in blacks of those mRNAs that positively correlate with the PAR4 response (FIG. 3A, middle heatmap shows more yellow in left half) and (iii) miRNAs negatively associated with PAR4 reactivity that show lower expression in blacks (FIG. 3A, visualized as more blue in lower left heatmap). FIG. 3B illustrates a focused network of miRNA-mRNA pairs in which 1) both the miRNA and mRNA are differentially expressed by race, 2) both the mRNA and miRNA correlate with PAR4-mediated platelet reactivity, 3) the miRNA is predicted to target the mRNA, and 4) the miRNA and mRNA levels are inversely correlated.

Figure 4E:
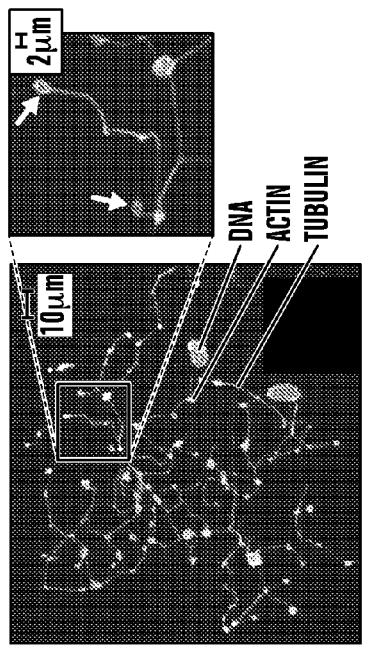
Figure 4G:
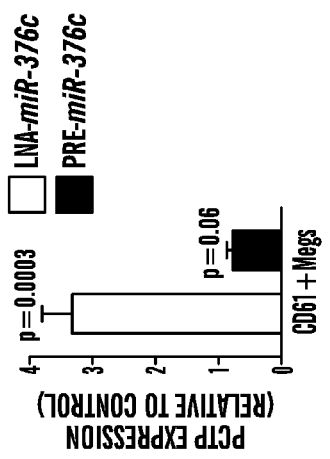
Figure 4F:
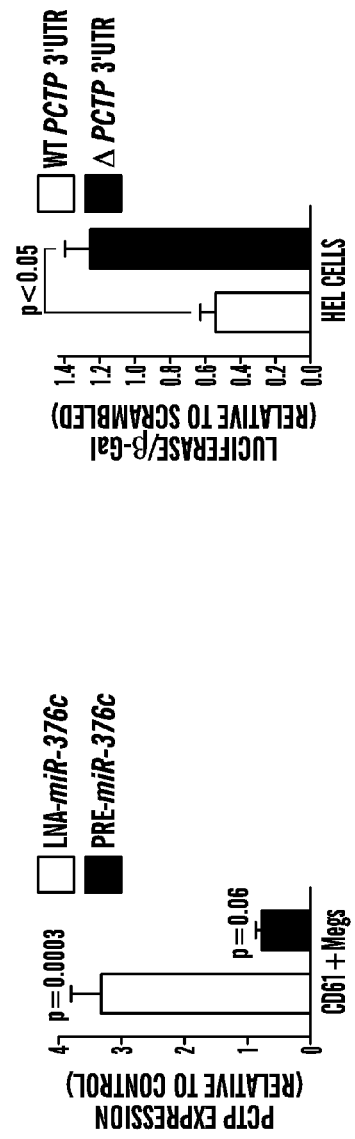
Figure 10:
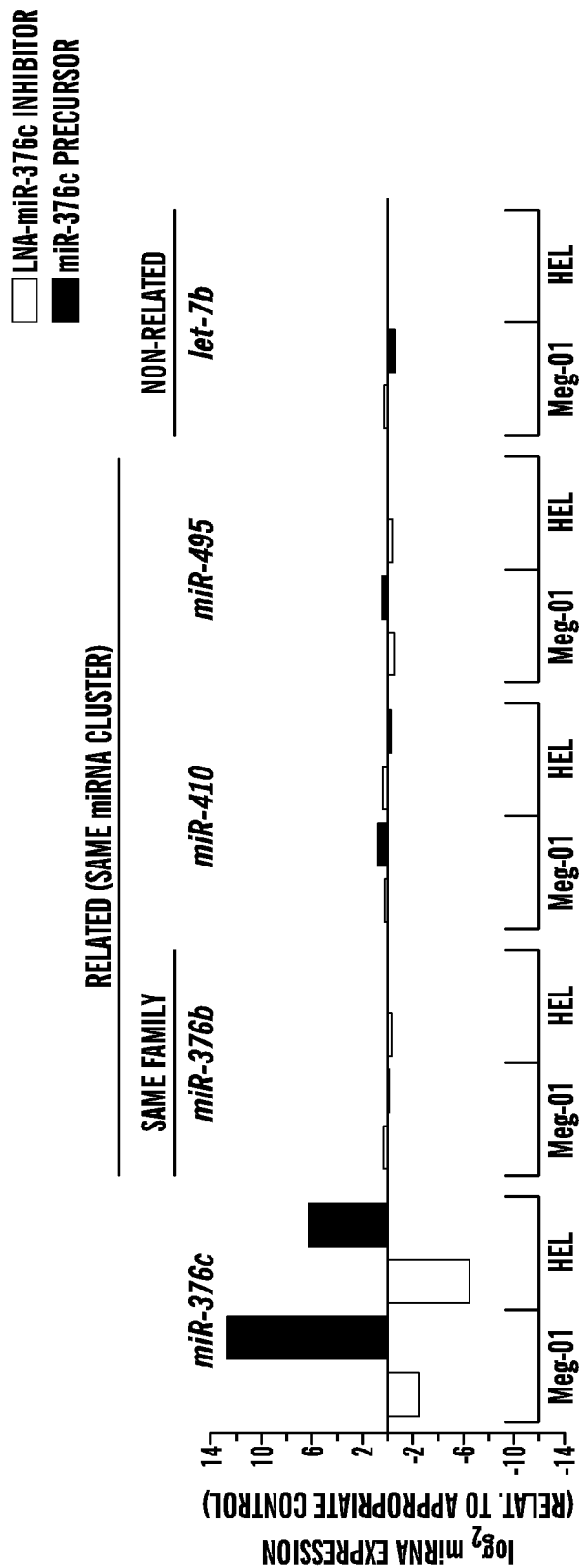
FIG. 10 shows effect of miR-376c transfection on related miRNAs. Transfection of miR-376c precursor or LNA inhibitor resulted in the expected alterations in miR-376c levels while not affecting the level of miRNAs in the same family (miR-376b), genetic locus (miR-410 and miR-495), or other unrelated miRNAs (let-7b).

PC-TP was predicted to be targeted by miR-376c (FIG. 3B), and miR-376c levels significantly inversely correlated with PC-TP mRNA levels, PC-TP protein levels, and PAR4 reactivity in the PRAX cohort (FIG. 3C). Over-expression of miR-376c reduced PC-TP protein expression in HCT cells (FIG. 4A) as well as the Meg-01 megakaryocytic cell line (FIG. 4B), and reduced PC-TP mRNA levels in Meg-01 cells and the HEL megakaryocyte cell line (FIG. 4C). Additionally, inhibition of miR-376c caused PC-TP mRNA levels to rise (FIG. 4c). CD34+ hematopoietic stem cells were isolated from human cord blood and differentiated into megakaryocytes and proplatelets (FIGS. 4D-4E). Transfection of miR-376c LNA inhibitor into CD34+-derived CD61+ megakaryocytes increased PC-TP mRNA levels by more than 3-fold, while overexpression of the miR-376c precursor decreased PC-TP mRNA by 22% (FIG. 4F). The extent of miR-376c knockdown by the anti-miR-376c LNA inhibitor and overexpression by the precursor is shown in FIG. 10. Transfection with the LNA inhibitor had no effect on the expression level of a different miR-376 family member, miR-376b or on other miRNAs located within the same cluster, miR-410 and miR-495 (FIG. 10). Finally, reporter gene assays demonstrated the direct action of miR-376c on the wild type PC-TP 3'UTR but not a mutant PC-TP 3'UTR construct with a deleted miR-376c binding site (FIG. 4G).

A Large Cluster of Platelet miRNAs in the DLK1-DIO3 Region are Expressed Higher in White Subjects.

Figure 5A:
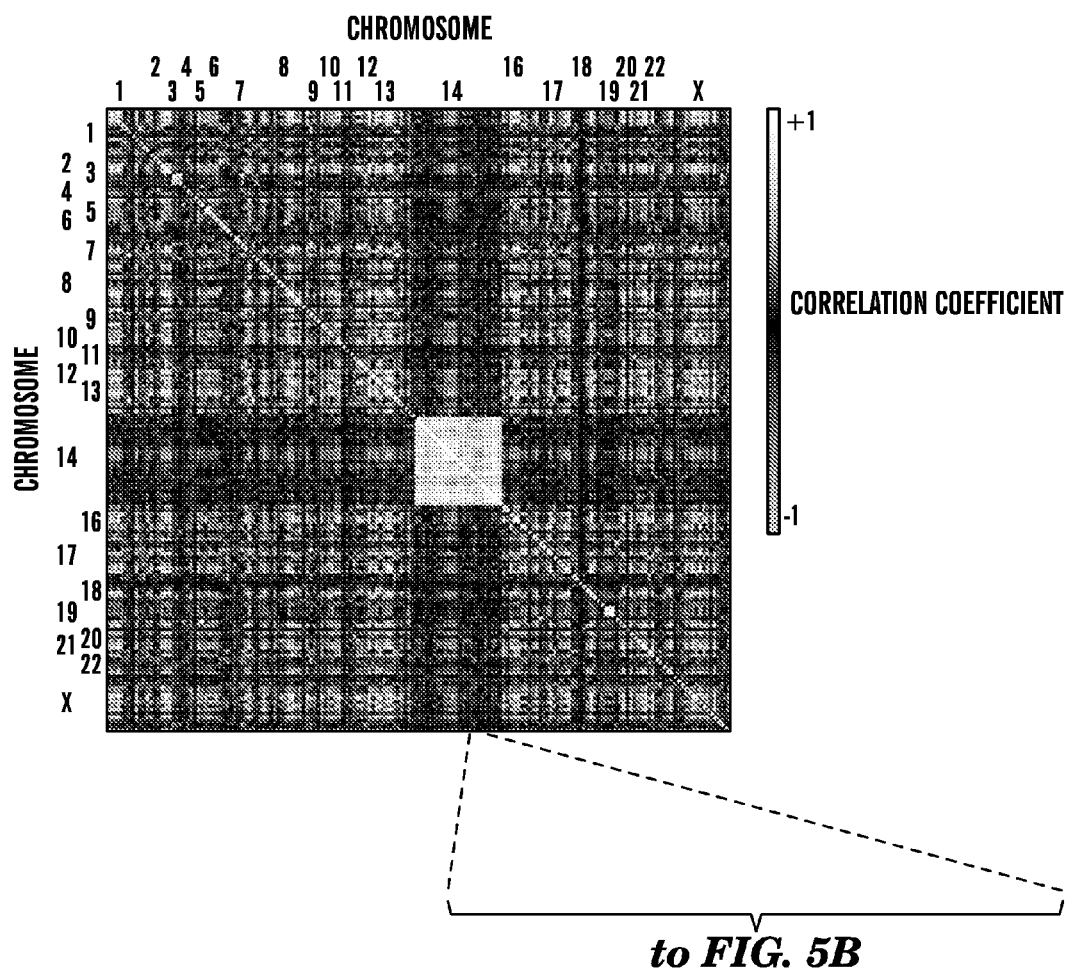
FIGS. 5A-5C show that a large miRNA cluster in the DLK1-DIO3 region is differentially expressed by race.
Figure 5B:
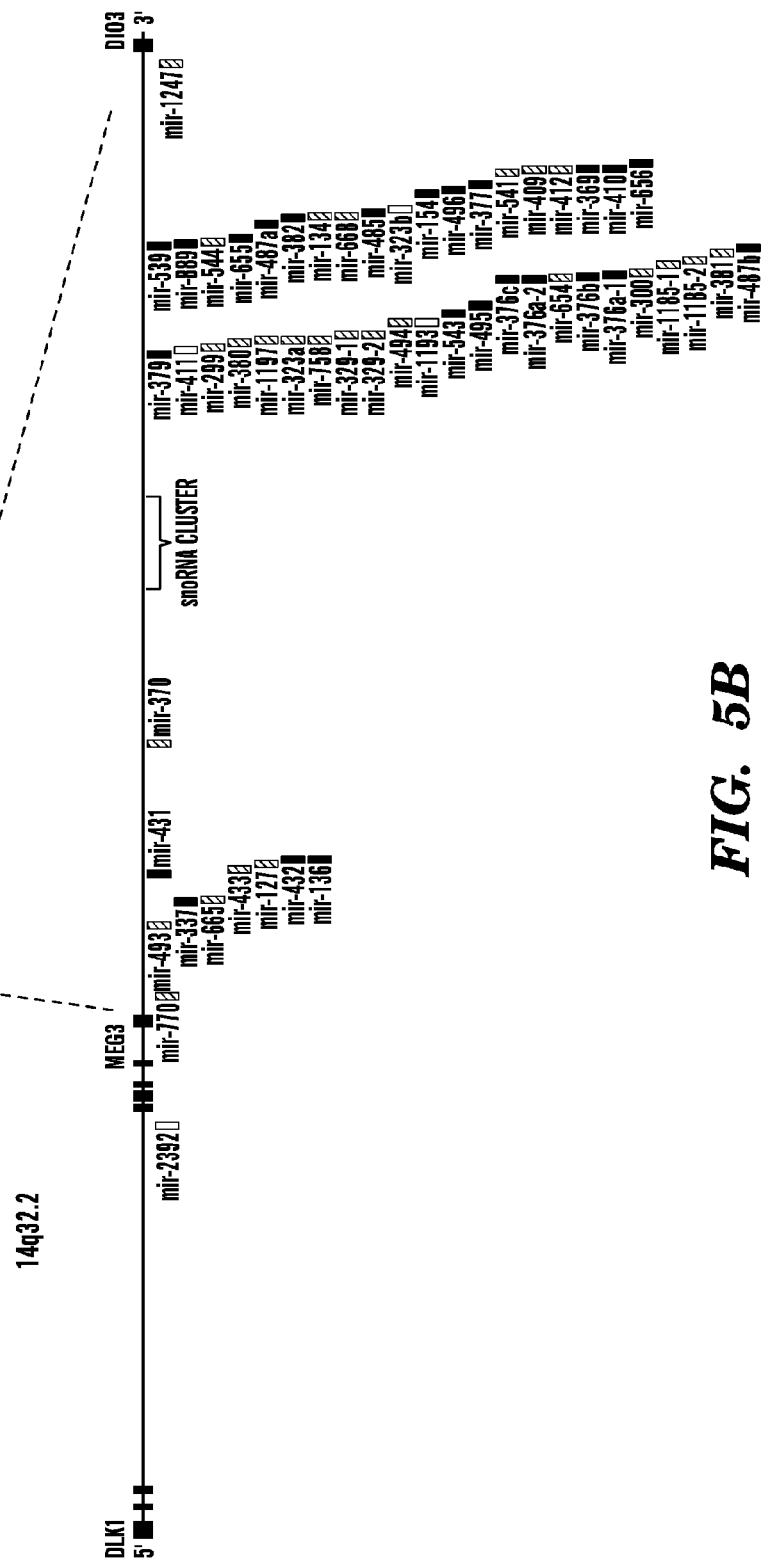
Figure 5C:
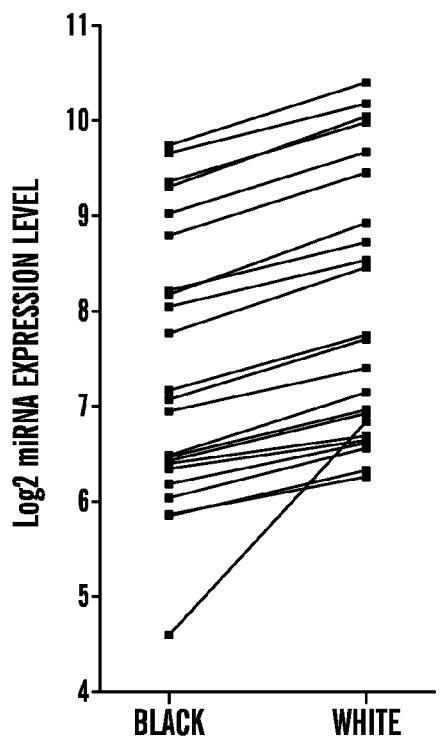
Figure 11:
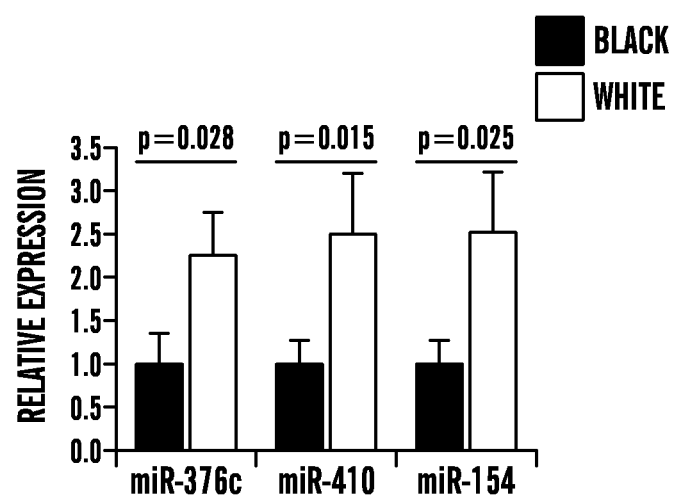
FIG. 11 shows RT-PCR validation of miRNAs differentially expressed by race and identified by Nanostring technology. Y-axis shows expression relative to platelet RNA from black subjects. P-values calculated by t-test.

MiR-376c is one of a set of miRNAs DE by race that appeared to be positively correlated with one another (FIG. 3A, visualized as vertical blue and yellow swatches in the miRNA heatmap; highlighted by the vertical bar next to the miRNA heatmap). Indeed, expression analysis revealed a significant correlation among 24 of the 178 common platelet miRNAs, and all 24 mapped to chromosome 14q32.2 (FIG. 5A). This locus is most commonly called the DLK1-DIO3 genomic region and contains a large cluster of miRNA genes (FIG. 5B). When a composite expression score for the miRNAs from this locus was generated for each of the 154 subjects, race showed a strong association with expression (black vs. white p=$1.09 \times 10^{-5}$). When age, gender, BMI and platelet count were included in a multiple linear regression analysis, race remained the dominant determinant of the DLK1-DIO3 region miRNA expression (p=0.000166, partial F statistic). As shown in FIG. 5C, all commonly expressed DLK1-DIO3 region mature miRNAs (n=24) were higher in whites than blacks. Table 4 lists the commonly expressed miRNAs DE by race and Table 5 lists the DLK1-DIO3 region miRNAs with mean values, variance and p-values by race. Racial differences in miRNA expression were confirmed by qRT-PCR (FIG. 11).

TABLE 4

List of miRNAs differentially expressed by race

| Probe* | DLK1-DIO3 locus | White Mean | Range | StDev | Black Mean | Range | StDev | Race p-value[†] | Race q-value[‡] |
|---|---|---|---|---|---|---|---|---|---|
| hsa-miR-431 | Yes | 8.94 | 7-10.4 | 0.81 | 8.18 | 4.67-9.94 | 1.14 | 4.16E−06 | 2.94E−04 |
| hsa-miR-410 | Yes | 7.71 | 6.12-9.3 | 0.76 | 7.08 | 4.23-8.82 | 0.93 | 6.72E−06 | 2.94E−04 |
| hsa-miR-487a | Yes | 7.15 | 5.26-9.1 | 0.84 | 6.49 | 3.93-8.4 | 0.92 | 7.32E−06 | 2.94E−04 |
| hsa-miR-337-3p | Yes | 8.47 | 6.35-10.05 | 0.8 | 7.77 | 4.74-9.34 | 1.08 | 7.73E−06 | 2.94E−04 |
| hsa-miR-495 | Yes | 9.68 | 7.9-11.15 | 0.76 | 9.04 | 6.32-10.55 | 0.97 | 8.39E−06 | 2.94E−04 |
| hsa-miR-377 | Yes | 10.41 | 8.19-11.95 | 0.79 | 9.75 | 6.69-11.38 | 1 | 9.91E−06 | 2.94E−04 |
| hsa-miR-99a | No | 6.3 | 5.49-7.41 | 0.41 | 5.96 | 4.4-6.71 | 0.54 | 1.65E−05 | 3.38E−04 |
| hsa-miR-485-3p | Yes | 6.85 | 0.01-11.4 | 2.88 | 4.5 | 0.03-8.83 | 3.43 | 1.78E−05 | 3.38E−04 |
| hsa-miR-450a | No | 7.12 | 5.3-8.08 | 0.52 | 6.69 | 5.22-8.46 | 0.69 | 2.00E−05 | 3.38E−04 |
| hsa-miR-655 | Yes | 6.69 | 5.73-7.75 | 0.45 | 6.41 | 5.6-7.23 | 0.36 | 2.25E−05 | 3.38E−04 |

TABLE 4-continued

List of miRNAs differentially expressed by race

| Probe* | DLK1-DIO3 locus | White Mean | White Range | White StDev | Black Mean | Black Range | Black StDev | Race p-value† | Race q-value‡ |
|---|---|---|---|---|---|---|---|---|---|
| hsa-miR-154 | Yes | 8.73 | 6.54-10.71 | 0.75 | 8.22 | 6.52-9.38 | 0.68 | 2.26E-05 | 3.38E-04 |
| hsa-miR-29a | No | 11.48 | 10.72-12.39 | 0.36 | 11.21 | 10.21-12.13 | 0.4 | 2.28E-05 | 3.38E-04 |
| hsa-miR-543 | Yes | 7.75 | 6.08-9.15 | 0.79 | 7.18 | 5.43-8.89 | 0.87 | 3.37E-05 | 4.55E-04 |
| hsa-miR-136 | Yes | 10.06 | 7.77-12.03 | 1 | 9.31 | 5.97-11.43 | 1.17 | 3.68E-05 | 4.55E-04 |
| hsa-miR-496 | Yes | 6.93 | 5.49-8.39 | 0.68 | 6.44 | 4.71-7.75 | 0.76 | 3.84E-05 | 4.55E-04 |
| hsa-miR-369-3p | Yes | 9.46 | 7.34-10.98 | 0.85 | 8.8 | 6.02-10.64 | 1.09 | 4.67E-05 | 5.20E-04 |
| hsa-miR-150 | No | 6.18 | 5.1-7.48 | 0.43 | 6.5 | 5.61-8.56 | 0.55 | 9.14E-05 | 9.57E-04 |
| hsa-miR-574-5p | No | 6.29 | 5.34-7.2 | 0.38 | 6.56 | 5.35-7.59 | 0.47 | 1.39E-04 | 1.38E-03 |
| hsa-miR-376c | Yes | 10 | 7.69-11.67 | 0.87 | 9.37 | 6.19-11.11 | 1.12 | 1.47E-04 | 1.38E-03 |
| hsa-miR-539 | Yes | 6.26 | 4.35-7.9 | 0.64 | 5.85 | 4.23-6.86 | 0.65 | 1.61E-04 | 1.43E-03 |
| hsa-miR-379 | Yes | 7.4 | 5.6-8.82 | 0.7 | 6.96 | 5.15-8.35 | 0.75 | 1.84E-04 | 1.56E-03 |
| hsa-miR-625 | No | 5.93 | 5-7.41 | 0.53 | 6.25 | 4.95-7.67 | 0.54 | 2.63E-04 | 2.13E-03 |
| hsa-miR-656 | Yes | 6.34 | 4.58-7.68 | 0.75 | 5.86 | 3.9-7.33 | 0.83 | 2.84E-04 | 2.20E-03 |
| hsa-miR-337-5p | Yes | 6.97 | 3.35-8.63 | 0.84 | 6.47 | 4.74-7.87 | 0.82 | 3.04E-04 | 2.26E-03 |
| hsa-miR-23b | No | 10.04 | 9.58-10.55 | 0.28 | 10.24 | 9.05-11.03 | 0.39 | 3.26E-04 | 2.32E-03 |
| hsa-miR-223 | No | 16.93 | 16.54-17.36 | 0.16 | 16.84 | 16.48-17.27 | 0.16 | 9.48E-04 | 6.49E-03 |
| hsa-miR-382 | Yes | 6.56 | 4.42-8.71 | 0.92 | 6.04 | 3.93-8.29 | 1.02 | 1.06E-03 | 6.98E-03 |
| hsa-miR-125b | No | 8.21 | 6.1-9.63 | 0.61 | 7.88 | 6.22-8.88 | 0.64 | 1.26E-03 | 7.98E-03 |
| hsa-miR-21 | No | 14.8 | 14.07-15.44 | 0.3 | 14.96 | 13.93-15.47 | 0.32 | 1.33E-03 | 8.15E-03 |
| hsa-miR-432 | Yes | 6.27 | 4.35-7.64 | 0.7 | 5.87 | 4.05-7.51 | 0.83 | 1.40E-03 | 8.31E-03 |
| hsa-miR-487b | Yes | 8.55 | 6.5-10.29 | 0.87 | 8.05 | 5.34-9.58 | 1.04 | 2.02E-03 | 1.16E-02 |
| hsa-miR-145 | No | 9.64 | 7.71-11.55 | 0.86 | 10.07 | 8.23-11.98 | 0.84 | 2.30E-03 | 1.28E-02 |
| hsa-miR-199b-5p | No | 6.29 | 5.6-7.04 | 0.3 | 6.14 | 5.44-6.75 | 0.3 | 2.71E-03 | 1.46E-02 |
| hsa-miR-376b | Yes | 6.62 | 3.97-8.8 | 0.9 | 6.19 | 4.3-7.53 | 0.85 | 2.88E-03 | 1.51E-02 |
| hsa-miR-590-5p | No | 10.55 | 8.58-11.55 | 0.47 | 10.24 | 6.1-11.59 | 0.82 | 4.24E-03 | 2.16E-02 |
| hsa-miR-376a | Yes | 10.19 | 7.75-12.47 | 1 | 9.67 | 6.14-11.72 | 1.23 | 4.61E-03 | 2.28E-02 |
| hsa-miR-221 | No | 13.39 | 12.4-14.23 | 0.3 | 13.26 | 12.16-13.89 | 0.27 | 5.25E-03 | 2.53E-02 |
| hsa-miR-889 | Yes | 6.65 | 5.32-8.09 | 0.64 | 6.35 | 4.83-7.92 | 0.7 | 5.50E-03 | 2.57E-02 |
| hsa-miR-301a | No | 9.94 | 8.92-10.38 | 0.22 | 10.03 | 9.53-10.48 | 0.19 | 5.79E-03 | 2.64E-02 |
| hsa-miR-101 | No | 11.38 | 9.32-12.36 | 0.61 | 11.53 | 10.16-12.58 | 0.5 | 5.98E-03 | 2.65E-02 |
| hsa-miR-143 | No | 8.21 | 6.32-10.04 | 0.86 | 8.6 | 6.48-10.33 | 0.88 | 6.10E-03 | 2.65E-02 |
| hsa-let-7c | No | 7.42 | 6.64-8.17 | 0.38 | 7.25 | 6.25-8.2 | 0.45 | 8.49E-03 | 3.60E-02 |
| hsa-miR-574-3p | No | 7.9 | 5.78-9.59 | 0.76 | 8.25 | 5.84-9.75 | 0.86 | 8.87E-03 | 3.67E-02 |
| hsa-miR-590-3p | No | 7.17 | 5.86-7.89 | 0.4 | 6.95 | 4.32-7.96 | 0.63 | 1.04E-02 | 4.20E-02 |
| hsa-miR-362-5p | No | 5.97 | 5.38-6.53 | 0.23 | 6.08 | 5.23-6.82 | 0.32 | 1.25E-02 | 4.95E-02 |
| hsa-miR-1308 | No | 7.92 | 6.67-8.97 | 0.43 | 7.76 | 6.57-8.43 | 0.37 | 1.49E-02 | 5.77E-02 |

TABLE 4-continued

List of miRNAs differentially expressed by race

| Probe* | DLK1-DIO3 locus | White | | | Black | | | Race p-value† | Race q-value‡ |
|---|---|---|---|---|---|---|---|---|---|
| | | Mean | Range | StDev | Mean | Range | StDev | | |
| hsa-miR-1908 | No | 6.38 | 5.28-7.11 | 0.33 | 6.25 | 5.09-6.86 | 0.31 | 1.67E-02 | 6.33E-02 |
| hsa-miR-363 | No | 7.46 | 6.68-7.96 | 0.26 | 7.36 | 6.81-7.92 | 0.27 | 1.78E-02 | 6.62E-02 |
| hsa-miR-107 | No | 10.9 | 9.37-12.15 | 0.58 | 11.11 | 9.77-12.38 | 0.64 | 3.15E-02 | 1.14E-01 |
| hsa-miR-486-3p | No | 6.79 | 6.34-7.47 | 0.24 | 6.71 | 6.06-7.26 | 0.27 | 3.45E-02 | 1.23E-01 |
| hsa-miR-660 | No | 6.4 | 5.5-7.24 | 0.39 | 6.52 | 5.71-7.19 | 0.34 | 3.83E-02 | 1.34E-01 |
| hsa-miR-424 | No | 6.58 | 4.98-8.47 | 0.68 | 6.32 | 4.32-9.12 | 0.92 | 3.90E-02 | 1.34E-01 |
| hsa-miR-362-3p | No | 6.66 | 5.51-7.48 | 0.35 | 6.77 | 5.35-7.3 | 0.32 | 4.55E-02 | 1.53E-01 |

*Annotation provided by Nanostring Technologies.
†P-value is calculated using T-test.
‡The q-value represents the p-value adjusted for multiple testing using the Benjamini & Hochberg False Discovery Rate (1995).

TABLE 5

List of miRNAs located in DLK1-DIO3

| Probe* | White | | | Black | | | Race p-value† | Race q-value‡ |
|---|---|---|---|---|---|---|---|---|
| | Mean | Range | StDev | Mean | Range | StDev | | |
| hsa-miR-431 | 8.94 | 7-10.4 | 0.81 | 8.18 | 4.67-9.94 | 1.14 | 4.16E-06 | 2.94E-04 |
| hsa-miR-410 | 7.71 | 6.12-9.3 | 0.76 | 7.08 | 4.23-8.82 | 0.93 | 6.72E-06 | 2.94E-04 |
| hsa-miR-487a | 7.15 | 5.26-9.1 | 0.84 | 6.49 | 3.93-8.4 | 0.92 | 7.32E-06 | 2.94E-04 |
| hsa-miR-337-3p | 8.47 | 6.35-10.05 | 0.8 | 7.77 | 4.74-9.34 | 1.08 | 7.73E-06 | 2.94E-04 |
| hsa-miR-495 | 9.68 | 7.9-11.15 | 0.76 | 9.04 | 6.32-10.55 | 0.97 | 8.39E-06 | 2.94E-04 |
| hsa-miR-377 | 10.41 | 8.19-11.95 | 0.79 | 9.75 | 6.69-11.38 | 1 | 9.91E-06 | 2.94E-04 |
| hsa-miR-485-3p | 6.85 | 0.01-11.4 | 2.88 | 4.6 | 0.03-8.83 | 3.43 | 1.78E-05 | 3.38E-04 |
| hsa-miR-655 | 6.69 | 5.73-7.75 | 0.45 | 6.41 | 5.6-7.23 | 0.36 | 2.25E-05 | 3.38E-04 |
| hsa-miR-154 | 8.73 | 6.54-10.71 | 0.75 | 8.22 | 6.52-9.38 | 0.68 | 2.26E-05 | 3.38E-04 |
| hsa-miR-543 | 7.75 | 6.08-9.15 | 0.79 | 7.18 | 5.43-8.89 | 0.87 | 3.37E-05 | 4.55E-04 |
| hsa-miR-136 | 10.06 | 7.77-12.03 | 1 | 9.31 | 5.97-11.43 | 1.17 | 3.68E-05 | 4.55E-04 |
| hsa-miR-496 | 6.93 | 5.49-8.39 | 0.68 | 6.44 | 4.71-7.75 | 0.76 | 3.84E-05 | 4.55E-04 |
| hsa-miR-369-3p | 9.46 | 7.34-10.98 | 0.85 | 8.8 | 6.02-10.64 | 1.09 | 4.67E-05 | 5.20E-04 |
| hsa-miR-376c | 10 | 7.69-11.67 | 0.87 | 9.37 | 6.19-11.11 | 1.12 | 1.47E-04 | 1.38E-03 |
| hsa-miR-539 | 6.26 | 4.55-7.9 | 0.64 | 5.85 | 4.23-6.86 | 0.65 | 1.61E-04 | 1.43E-03 |
| hsa-miR-379 | 7.4 | 5.6-8.82 | 0.7 | 6.96 | 5.15-8.35 | 0.75 | 1.84E-04 | 1.56E-03 |
| hsa-miR-656 | 6.34 | 4.58-7.68 | 0.75 | 5.86 | 3.9-7.33 | 0.83 | 2.84E-04 | 2.20E-03 |
| hsa-miR-337-5p | 6.97 | 3.35-8.63 | 0.84 | 6.47 | 4.74-7.87 | 0.82 | 3.04E-04 | 2.26E-03 |
| hsa-miR-382 | 6.56 | 4.42-8.71 | 0.92 | 6.04 | 3.93-8.29 | 1.02 | 1.06E-03 | 6.98E-03 |
| hsa-miR-432 | 6.27 | 4.35-7.64 | 0.7 | 5.87 | 4.05-7.51 | 0.83 | 1.40E-03 | 8.31E-03 |
| hsa-miR-487b | 8.55 | 6.5-10.29 | 0.87 | 8.06 | 5.34-9.58 | 1.04 | 2.02E-03 | 1.16E-02 |
| hsa-miR-376b | 6.62 | 3.97-8.8 | 0.9 | 6.19 | 4.3-7.53 | 0.85 | 2.88E-03 | 1.51E-02 |

TABLE 5-continued

List of miRNAs located in DLK1-DIO3

| Probe* | White | | | Black | | | Race p-value[†] | Race q-value[‡] |
|---|---|---|---|---|---|---|---|---|
| | Mean | Range | StDev | Mean | Range | StDev | | |
| hsa-miR-376a | 10.19 | 7.75-12.47 | 1 | 9.67 | 6.14-11.72 | 1.23 | 4.61E−03 | 2.28E−02 |
| hsa-miR-889 | 6.65 | 5.32-8.09 | 0.64 | 6.35 | 4.83-7.92 | 0.7 | 5.50E−03 | 2.57E−02 |

*Annotation provided by Nanostring Technologies
[†]P-value is calculated using T-test.
[‡]The q-value represents the p-value adjusted for multiple testing using the Benjamini & Hochberg False Discovery Rate (1995).

Discussion

The goal of this study was to characterize racial differences in platelet function and the RNAs that might contribute to these differences. Platelet aggregation in 70 black and 84 white healthy subjects was assessed, and mRNA and miRNA from highly purified blood platelets was profiled. The richness of this data set provided unique opportunities to establish miRNA-mRNA-physiology relationships that led to a number of novel and unexpected results. Several major findings emerged. First, compared to platelets form whites, platelets from blacks showed greater platelet reactivity in response to activation through the PAR4 thrombin receptor. Since PAR4 is expressed in tissues other than platelets (e.g., heart, brain, liver), these findings could be relevant for non-thrombotic diseases believed to show racial differences. Second, the novel platelet protein, PC-TP, mediates PAR4-dependent calcium mobilization and aggregation. Compared to platelets from whites, platelets from blacks expressed higher levels of PC-TP and greater PAR4-dependent calcium mobilization and aggregation through PC-TP. Third, miR-376c regulated expression of PC-TP in both megakaryocytes and megakaryocytic cell lines. It was also discovered a genomic module of miRNAs and target mRNAs that strongly correlate with this racial difference in PAR4-mediated platelet aggregation. Many of these miRNAs were clustered in the DLK1-DIO3 region and were expressed at higher levels in platelets from whites than blacks. These findings should be considered in clinical trials involving anti-platelet therapies and on-going drug development of inhibitors of protease activated receptors.

There is a paucity of literature considering racial differences in platelet function. A single small study has reported that calcium mobilization varied by race in patients with hypertension (Cho et al., Hypertension 1995, 25, 377-383), but it was unclear if this difference was due to race or disease (hypertension) and the responsible molecular mechanism was not considered. It was found that platelets from blacks demonstrated significantly greater activation to PAR4-AP than platelets from whites. Compared to thrombin, PAR activating peptides have the advantage of discriminating between PAR1 and PAR4 and are amenable to the relatively high-throughput screening needed in the PRAX1 study. Nevertheless, to address the possibility that there could be an unusual interaction between race and PAR4-AP but not between race and thrombin (i.e., that PAR4-AP in this study does not reflect the true thrombin response), two additional studies with different subjects were performed to assess thrombin-induced platelet aggregation after PAR1 inhibition. Both the thrombin-dose-response study (FIGS. 7A-7E) and replicate study (FIG. 1B) showed racial differences mediated by thrombin-activated PAR4. These data suggest the racial difference in PAR4 reactivity may be primarily kinetic, since the greater aggregation in platelets from blacks was apparent only at the earliest time points and lowest thrombin concentrations. Additional studies are needed to determine whether there is a racial difference in the kinetics of the response to thrombin when both PAR1 and PAR4 are functional. The data using thrombin also indicate 1) there is not an unknown plasma "cofactor" that differs by race affecting PAR4-mediated platelet activation and 2) the results in FIG. 1A are not due to racial differences in an undiscovered protease that activates PAR4 and not PAR1. The fact that no racial difference was observed for other agonists strongly supports a relationship between race and PAR4-mediated platelet aggregation, and not the effects of other crucial variables of the read-out such as integrin $\alpha IIb\beta 3$ levels or a plasma protein. Furthermore, plasma fibrinogen and VWF activity were measured and neither differed by race (Table 1). Moreover, this racial difference in PAR4-AP induced platelet aggregation was observed in separate cohorts from different cities (Houston and Philadelphia) with independent reagents, instrumentation, and personnel.

A fundamental aspect of the conclusion pertains to race. Black and white subjects were recruited randomly throughout the duration of the study and there was no sequential recruitment bias by race. Although self-identified race and ethnicity (SIRE) has been shown to strongly correlate with selected genomic markers and ancient geographical ancestry (Tang et al., Am. J. Hum. Genet. 2005, 76, 268-275; Rosenberg et al., Science 2002, 298, 2381-2385; Mountain et al., Am. J. Hum. Genet. 1997, 61, 705-718; Risch et al., Genome Biol. 2002, 3, comment 2007), the use of SIRE in PRAX1 was validated using PCA, which provided an unbiased examination of structure in the genotype data. American blacks are an admixed group (Tishkoff et al., Science 2009, 324, 1035-1044) and African lineages have greater diversity; these facts are reflected in the greater spread within that PCA-defined group. Although this strong relationship between self-identified race and genetic markers supported conclusions regarding a genetic effect on platelet function, it does not preclude a contribution of socioeconomic or environmental factors to variation in PAR4 reactivity.

Genome-wide gene expression analysis showed more DE transcripts were positively associated with PAR4 reactivity than were negatively associated. Such asymmetry has been noted in other studies (Chahrour et al, Science 2008, 320, 1224-1229). Perhaps the human platelet response through PAR4 evolved in such a way as to promote blood clotting after trauma, thus providing a survival advantage; other explanations by evolution or genetic drift are possible. One hundred thirteen mRNAs (out of >9000 expressed transcript) were DE by both race and PAR4 reactivity. PC-TP was pursued because of its strong statistical associations and because of its biologic plausibility. PC-TP belongs to the steroidogenic acute regulatory transfer protein-related transfer (START) domain superfamily, which constitutes a functionally diverse group of proteins that share a unique START domain for binding lipids (Schrick et al., Genome Biol. 2004, 5, R41). PC-TP has been presumed to be expressed primarily in the liver, kidneys, and testis. PC-TP protein was not known to be present or function in platelets (Geijtenbeek et al., Biochem. J. 1996, 316 Pt 1, 49-55). Besides PC transfer in vitro, PC-TP also regulates both insulin and glucose metabolism in mice and human cell lines (Kang et al., Trends Endocrinol. Metab. 2010, 21, 449-456; Baez, et al., Biochem. J. 2005, 388, 57-63; Lev, Nat. Rev. Mol. Cell Biol. 2010, 11, 739-750), but the human in vivo function of PC-TP remains unclear. PC comprises a major fraction of platelet phospholipids and multiple subcellular locations of PC may exist (Mahadevappa et al., J. Biol. Chem. 1984, 259, 9369-9373). PC is the classic substrate for phospholipase D, generating phosphatidic acid that can be converted to the second messenger DAG (Exton, J. Biol. Chem. 1990, 265, 1-4). PC can also be hydrolyzed by phospholipase C to generate PIP2 with subsequent release of calcium from intracellular stores. The PC-TP inhibitor, LDN-193,188, blocked PAR4- but not PAR1-induced platelet aggregation, supporting of a role for PC-TP in platelet function. Nevertheless, off-target effects of LDN-193,188 cannot be excluded. However, depleting PC-TP in megakaryocytic cells via shRNA interference produced a functional effect on calcium mobilization that was also PAR4- but not PAR1-dependent. These studies in two different experimental systems, in addition to the racial difference seen in PAR4-mediation platelet calcium mobilization (FIG. 2L) support a novel role for PC-TP mediation of intracellular calcium transients and in the racial difference in PAR4-induced platelet activation.

Figure 6:
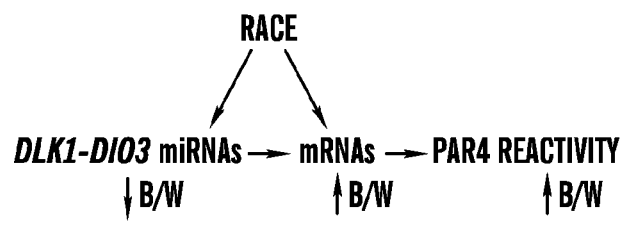
FIG. 6 is schematic summarizing the relationship of race with the expression of the DLK1-DIO3 region miRNAs and target mRNAs and PAR4 reactivity.

The DLK1-DIO3 region at the 14q32.2 locus is evolutionarily conserved, harboring DLK1 and MEG3, antisense RTL1, many small nucleolar RNAs (snoRNAs), long intergenic RNAs (lincRNAs) (including MEG3) and the largest currently known cluster of miRNAs in the human genome (reviewed in Bebetatos et al., Cell Mol Life Sci 2012). The data demonstrate the miRNAs in this region are expressed at higher levels in platelets from white subjects than black subjects, and it will be important to assess other tissues and the other RNAs encoded in this region for this racial difference. MiR-376c, which resides within the DLK1-DIO3 region, was DE by race and PAR4-induced platelet reactivity and was predicted to target the 3'UTR of PC-TP. As might be expected if miR-376c targeted PC-TP and resulted in mRNA degradation, miR-376c levels were inversely correlated with PC-TP mRNA and protein, and weakly correlated with PAR4-induced platelet aggregation (FIG. 3C). Direct perturbation of PC-TP expression by miR-376c was demonstrated by a series of overexpression, inhibition and binding site mutation studies in a variety of cell types, including megakaryocytic cell lines and primary cultured human megakaryocytes. FIG. 6 summarizes the proposed relationships identified in this study, emphasizing the race effect on RNAs, leading to racial differences in platelet PAR4 reactivity. Although the there is a strong correlation between the platelet and megakaryocyte transcriptomes (Edelstein et al., Blood 2011, 117, 5289-5296), racial differences in platelet RNAs cannot be assumed to reflect differences that occurred in the megakaryocytes. Addressing this possibility would require a racially diverse source of progenitor cells. Nevertheless, transcriptomic and bioinformatic analyses of platelet RNA can guide experiments in cells to permit insights into relevant gene regulation in megakaryocytes.

There are clinical consequences to the findings described herein, particularly in an era where personalized medicine has been advanced as a strategy to improve patient outcomes. First, awareness and understanding of differences by which platelets are activated in blacks and whites is expected to aid in our ability to optimally treat these populations following myocardial infarction and stroke. Although the issue of race serving as a proxy for genetics in medical practice and research is controversial (Phimister, N. Engl. J. Med. 2003, 348, 1081-1082), the results suggest SIRE may have value in assessing hemostasis-thrombosis risk in some populations. Anti-platelet therapy is a mainstay of managing coronary heart disease. However, there has been a notable absence or, at best poor representation of blacks in clinical trials of anti-platelet therapies and in genome-wide association studies of atherothrombotic phenotypes. Unfortunately, neither cardiovascular trials with vorapaxar (Morrow et al., N. Eng. J. Med. 2012, 366, 1404-1413; Bonaca et al., Circulation 2013, 127, 1522-1529; Scirica et al., Lancet 2012, 380, 1317-1324) nor trials listed at clinicaltrials.gov allow assessment of racial effects in clinical outcomes, and it is unknown whether the racial difference in platelet reactivity impacts the benefits and risks of these treatments. The PAR1 inhibitor vorapaxar has been used in clinical trials for the prevention of secondary atherothrombotic events (Morrow et al., N. Eng. J. Med. 2012, 366, 1404-1413; Bonaca et al., Circulation 2013, 127, 1522-1529; Scirica et al., Lancet 2012, 380, 1317-1324) and other novel inhibitors of PAR1 and PAR4 are currently in clinical development (Vergnolle, Pharmacol. Ther. 2009, 123, 292-309). In the presence of vorapaxar, PAR4 is the only means by which thrombin can activate platelets. Thus, it is critical to know whether selection and dosing of such agents should be adjusted by race to maximize benefit and avoid toxicity. The findings call for greater access to clinical trial data to address the effect of race on anti-platelet therapies. In addition, the racial differences identified in the DLK1-DIO3 region miRNA expression may be present in other tissues, and more large scale RNA studies can address this question. Lastly, it will be of interest to know whether PC-TP inhibition might prove useful as an anti-thrombotic strategy, especially in disorders of altered glucose and insulin metabolism.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A method of inhibiting platelet activation, the method comprising contacting a platelet with a PC-TP inhibitor 2,4-dichloro-N-(4-(N-(4,6-dimethylpyrimidin-2-yl)sulfamoyl)phenylcarbamoyl)-benzamide (LDN-193,188), or a pharmaceutically acceptable salt thereof, and wherein the PC-TP inhibitor inhibits PAR4 activation.

2. The method of claim 1, wherein said contacting is in vitro.

3. The method of claim 1, wherein said contacting is in vivo.

4. The method of claim 3, wherein said in vivo contacting is in a subject in need of prevention or treatment for pathologic thrombosis, or treatment for a disorder treatable by a PAR4 inhibitor.

5. The method of claim 4, wherein said subject is a mammal.

6. The method of claim 5, wherein said mammal is a human.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
agaatgcaac ggagagactg tggt                24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
tcacatggat cttcctccct tcca                24